(12) United States Patent
Chauhan et al.

(10) Patent No.: US 11,542,239 B2
(45) Date of Patent: Jan. 3, 2023

(54) ELAGOLIX SODIUM COMPOSITIONS AND PROCESSES

(71) Applicant: AbbVie Inc., North Chicago, IL (US)

(72) Inventors: Niharika Chauhan, Chicago, IL (US); Raimundo Ho, Glenview, IL (US); Albert Kruger, Pleasant Prairie, WI (US); Samrat Mukherjee, Grayslake, IL (US); Stephen T. Chau, Vernon Hills, IL (US); Erika Crane, Grayslake, IL (US); Alex Fabian, Wadsworth, IL (US); Sanjay Chemburkar, Gurnee, IL (US); Travis Dunn, Gurnee, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 16/519,443

(22) Filed: Jul. 23, 2019

(65) Prior Publication Data

US 2020/0024239 A1  Jan. 23, 2020

Related U.S. Application Data

(60) Provisional application No. 62/702,135, filed on Jul. 23, 2018.

(51) Int. Cl.
*C07D 239/54* (2006.01)

(52) U.S. Cl.
CPC ........ *C07D 239/54* (2013.01); *C07B 2200/13* (2013.01)

(58) Field of Classification Search
CPC combination set(s) only.
See application file for complete search history.

(56) References Cited

U.S. PATENT DOCUMENTS

| | | | |
|---|---|---|---|
| 6,872,728 B2 | 3/2005 | Zhu et al. | |
| 7,056,927 B2* | 6/2006 | Guo | A61P 5/00 514/274 |
| 7,419,983 B2 | 9/2008 | Guo et al. | |
| 8,765,948 B2* | 7/2014 | Gallagher | A61P 15/00 544/311 |
| 9,382,214 B2 | 7/2016 | Gallagher et al. | |
| 9,868,706 B2 | 1/2018 | Gallagher et al. | |
| 9,949,973 B2 | 4/2018 | Gao et al. | |
| 2006/0122204 A1 | 6/2006 | Huang et al. | |
| 2008/0096918 A1 | 4/2008 | Lindenschmidt et al. | |
| 2015/0018553 A1 | 1/2015 | Gallagher et al. | |
| 2017/0056403 A1 | 3/2017 | Goss et al. | |
| 2017/0057911 A1 | 3/2017 | Yelm et al. | |
| 2017/0129862 A1 | 5/2017 | Duncton et al. | |
| 2017/0320836 A1 | 11/2017 | Gallagher et al. | |

FOREIGN PATENT DOCUMENTS

| | | | | |
|---|---|---|---|---|
| WO | 2005007164 | 1/2015 | | |
| WO | 2017221144 | 12/2017 | | |
| WO | WO-2018198086 A1 * | 11/2018 | ........... | C07D 239/54 |
| WO | WO-2019112968 A1 | 6/2019 | | |
| WO | WO-2021044230 A1 | 3/2021 | | |

OTHER PUBLICATIONS

Chen et al. J. Med. Chem. 2008, 51, 7478-7485 (Year: 2008).*
Foreign Priority document for WO 2018/198086, IN, No. 201721015207 filed Apr. 28, 2017.*
Chen et al. J.Med. Chem. 51, p. 7478-7485 . (Year: 2008).*
Regan et al., "Zwitterionic uracil derivatives as potent GnRH receptor antagonists with improved pharmaceutical properties," Bioorganic & Medicinal Chemistry Letters , 2008, vol. 18, pp. 4503-4507.
Sullivan et al., "Kinetics of nonpeptide antagonist binding to the human gonadotropin-releasing hormone receptor: implications for structure-activity relationships and insurmountable antagonism," Biochemical Pharmacology, 2006, vol. 72, pp. 838-849.
"Process for the preparation of 1-(2-fluoro-6-(trifluoromethyl)benzyl)urea and (2-fluoro-6-(trifluoromethyl)phenyl)methanamine hydrochloride" IP.com No. IPCOM000250923D, IP.com Electronic Publication Date: Sep. 14, 2017, 3 pages.
Extended European Search Report for Application No. EP19841544.0 dated Mar. 3, 2022, 8 pages.
International Search Report and Written Opinion for Application No. PCT/US2019/042950, dated Sep. 18, 2019, 11 Pages.
Polepally A.R., et al., "Assessment of Clinical Drug-Drug Interactions of Elagolix, a Gonadotropin-Releasing Hormone Receptor Antagonist," The Journal of Clinical Pharmacology, 2020, vol. 60(12), pp. 1606-1616.
Pubchem. CID 102043127, pp. 1-6. Retrieved from the Internet < url: < a href="https://pubchem.ncbi.nlm.nlh.govicompound/102043127 > " > https://pubchem.ncbi.nlm.nlh.govicompound/102043127; p. 2, Dec. 24, 2015, formula. </url: < a > .
Pubchem. CID 13125865, pp. 1-5. Retrieved from the Internet < url: < a href="https://pubchem.ncbi.nlm.nih.gov/compound/13125865 > " > https://pubchem.ncbi.nlm.nih.gov/compound/13125865; p. 2, Feb. 8, 2007, formula. </url: < a > .

* cited by examiner

*Primary Examiner* — Erich A Leeser
(74) *Attorney, Agent, or Firm* — Neal, Gerber & Eisenberg LLP

(57) ABSTRACT

The present invention relates to compositions of elagolix sodium, and process and intermediates for the preparation thereof.

22 Claims, 19 Drawing Sheets

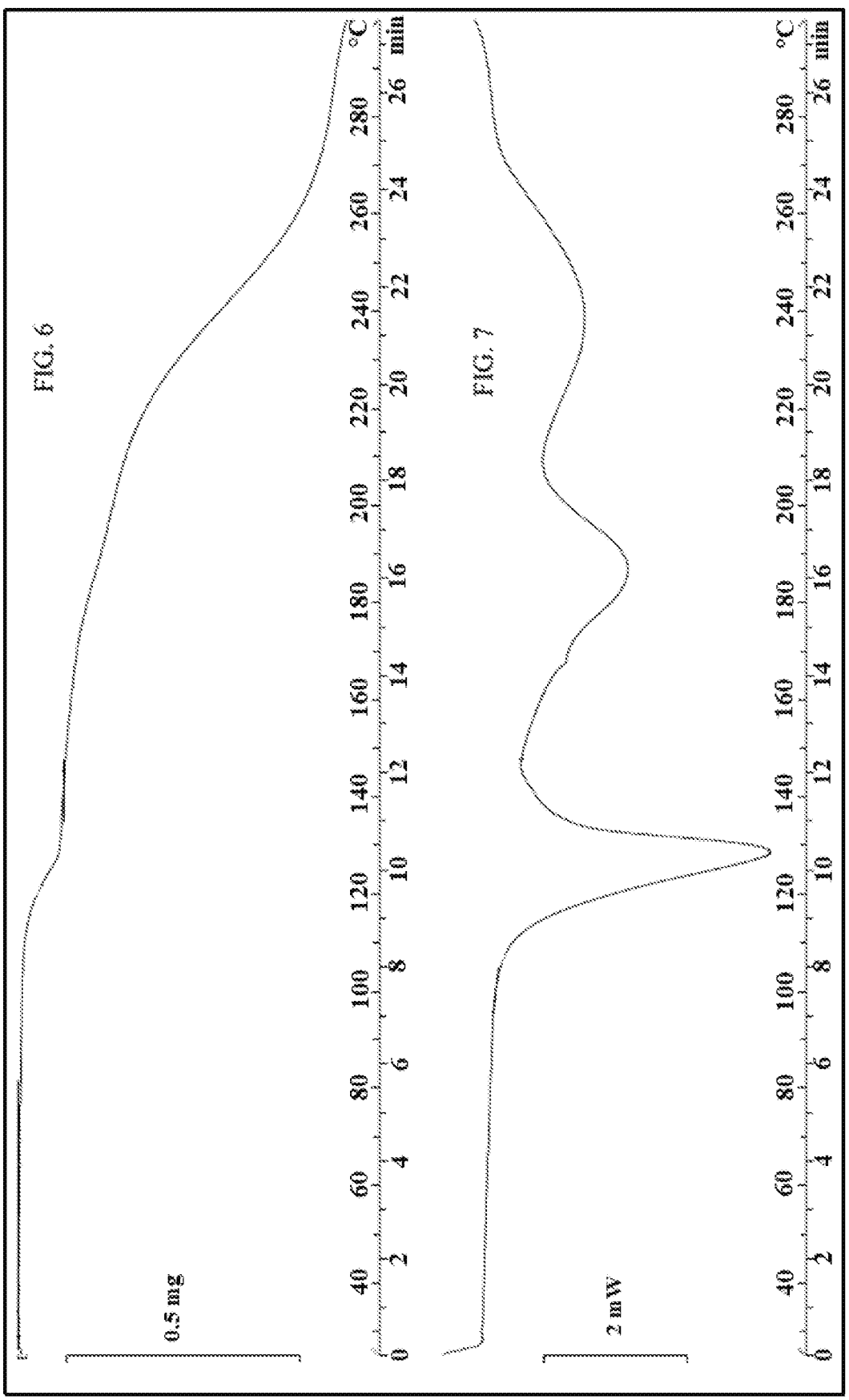

ELAGOLIX SODIUM COMPOSITIONS AND PROCESSES

RELATED APPLICATION

This application claims the benefit of U.S. Provisional Application No. 62/702,135, filed Jul. 23, 2018. The contents of which are incorporated herein by reference.

FIELD OF INVENTION

This invention relates to the active drug substance of elagolix sodium, a GnRH receptor antagonist that may be useful in the treatment of diseases such as endometriosis, uterine fibroids, adenomyosis, or polycystic ovary syndrome (PCOS).

BACKGROUND OF THE INVENTION

Elagolix, a gonadotropin-releasing hormone (GnRH) receptor antagonist, is an orally administered, short-acting molecule that blocks endogenous GnRH signaling by binding competitively to GnRH receptors in the pituitary gland. Administration results in readily reversible, dose-dependent inhibition of luteinizing hormone (LH) and follicle-stimulating hormone (FSH) secretion, leading to reduced ovarian production of the ovarian sex hormones, estradiol and progesterone, while on therapy. Elagolix is currently being investigated in diseases that are mediated by ovarian sex hormones, such as uterine fibroids, adenomyosis, endometriosis, or polycystic ovary syndrome. To date, elagolix has been studied in over 40 clinical trials totaling more than 3,000 subjects. Sodium salt of elagolix has been approved by US Food and Drug Admnistration as ORILISSA™

The process of making elagolix sodium, the active substance, has been described in patents and applications, U.S. Pat. Nos. 8,765,948, and 7,419,983 and International Published Application WO2017221144.

A commercially available active substance should not only have a very low impurity profile that meeting US FDA standards, but it should also be manufactured with the appropriate choice of intermediates and their solid forms in a manner that is reproducible, efficient, cost-effective and safe.

Since elagolix sodium active substance is generally amorphous, its active substance purification may be more complex than another active substance with established polymorphic forms. Therefore, elagolix active substance with improved manufacturability having a substantially pure active substance that is suitable for commercial scale manufacturing is highly desirable. Furthermore, an active substance specification limits having minimal mutagenic impurities, that will meet all regulatory standards is desirable.

BRIEF SUMMARY OF THE INVENTION

In one embodiment, a composition of Compound (I) is provided comprising, Compound (I),

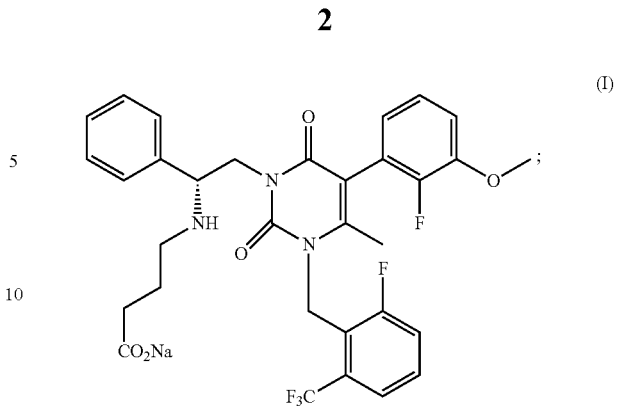

(I)

and one or more impurities, wherein the composition comprises at least about 97 weight percent of Compound (I) and not more than about 3 weight percent of the one or more impurities.

In some aspects, the composition comprises at least about 97 weight percent Compound (I) and not more than about 3 weight percent of one or more impurities selected from the group consisting of:

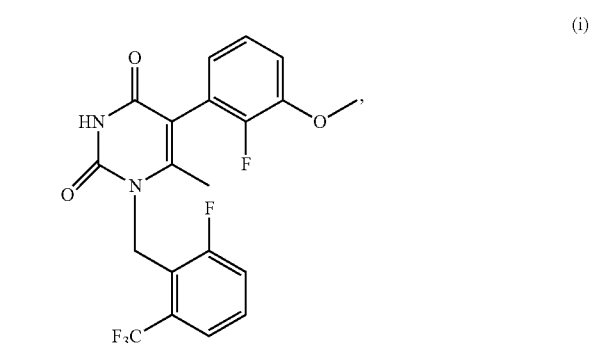

(i)

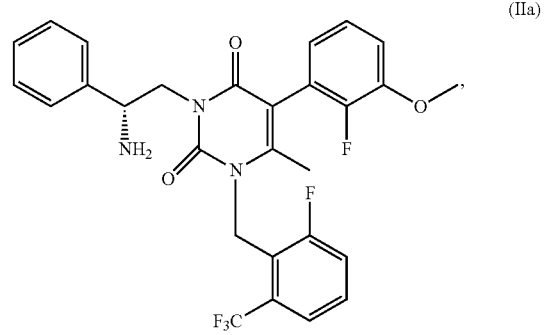

(IIa)

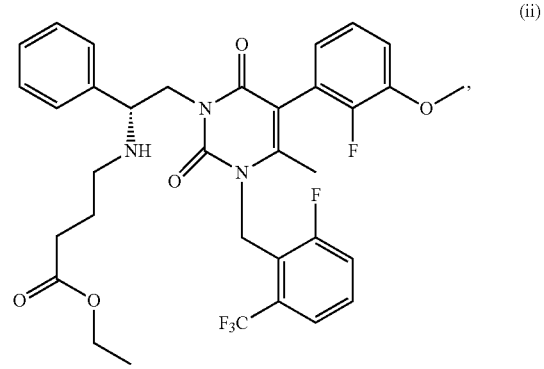

(ii)

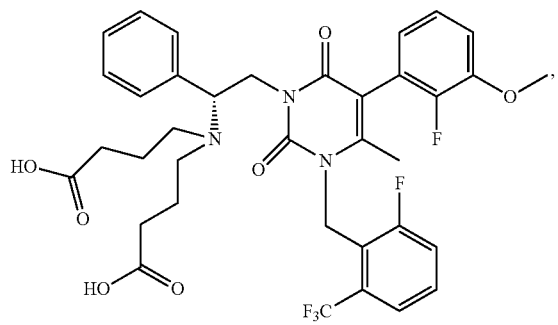
(iii)

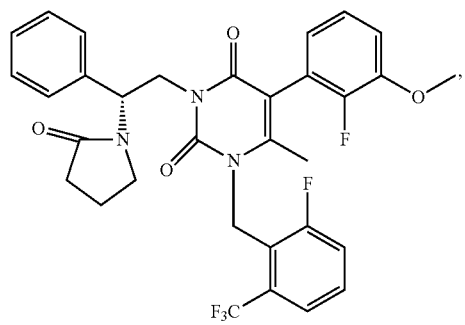
(iv)

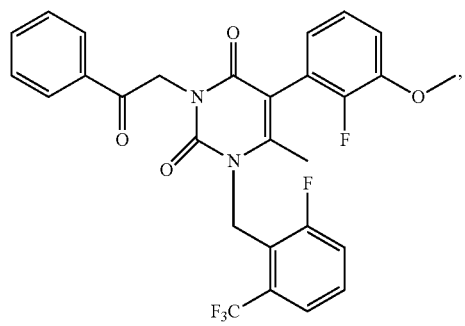
(v)

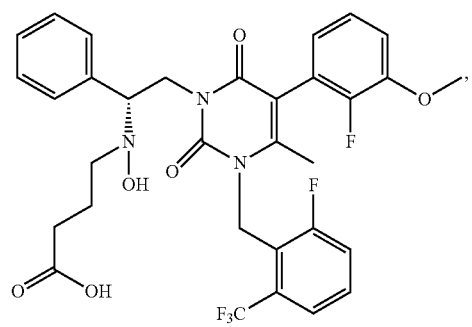
(vi)

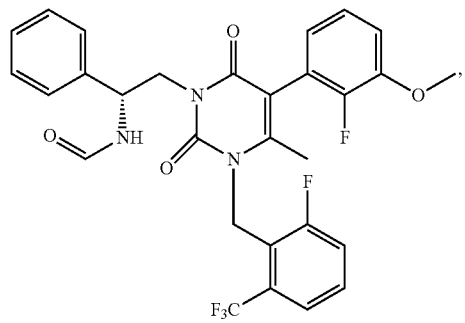
(vii)

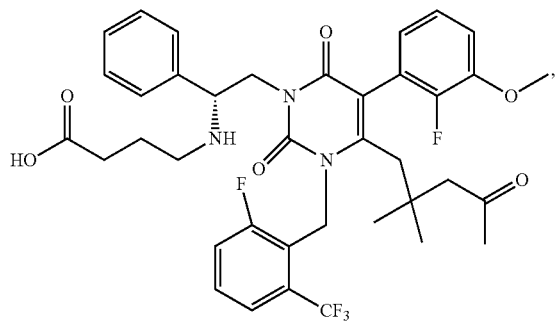
(viii)

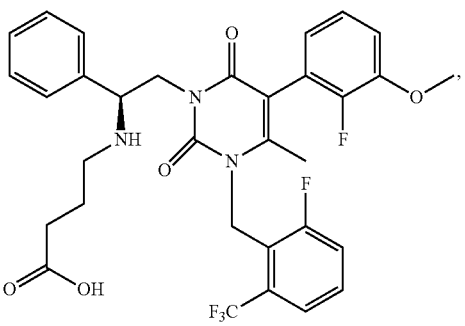
(ix)

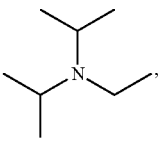
(x)

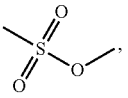
(xv)

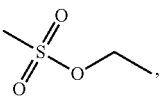
(xvi)

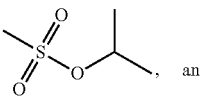
(xvii)

, and

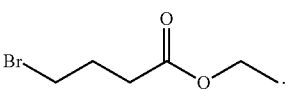
(xviii)

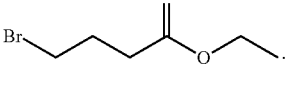
.

In some aspects, a composition of Compound (I) comprising at least about 97 weight percent Compound (I) and not more than about 3 weight percent of one or more impurities selected from the group consisting of Compounds (i, ii, iii, iv, v, vi, vii, viii, ix, x, xv, xvi, xvii, xviii, and IIa) is provided, and Compound (I) is amorphous.

In other aspects, a composition of Compound (I) comprising at least about 98 weight percent Compound (I) and not more than about 2 weight percent of one or more impurities selected from the group consisting of Compounds (i, ii, iii, iv, v, vi, vii, viii, ix, x, xv, xvi, xvii, xviii, and IIa) is provided.

In some aspects, a composition of Compound (I) comprising at least about 97 or 98 weight percent Compound (I) and not more than about 3 weight percent of one or more impurities selected from the group consisting of Compounds (i, ii, iii, iv, v, vi, vii, viii, ix, x, xv, xvi, xvii, xviii, and IIa) is provided, and Compound (I) is amorphous, wherein there two or more impurities.

In some aspects, a composition of Compound (I) comprising at least about 97 or 98 weight percent Compound (I) and not more than about 3 weight percent of one or more impurities selected from the group consisting of Compounds (i, ii, iii, iv, v, vi, vii, viii, ix, x, xv, xvi, xvii, xviii, and IIa) is provided, and Compound (I) is amorphous, wherein there three or more impurities.

In some aspects, a composition of Compound (I) comprising at least about 97 or 98 weight percent Compound (I) and not more than about 3 weight percent of one or more impurities selected from the group consisting of Compounds (i, ii, iii, iv, v, vi, vii, viii, ix, x, xv, xvi, xvii, xviii, and IIa) is provided, and Compound (I) is amorphous, wherein there four or more impurities.

In one embodiment, a process for preparing a substantially pure composition of Compound (I) is provided, comprising using, as an intermediate in the process, Compound (II),

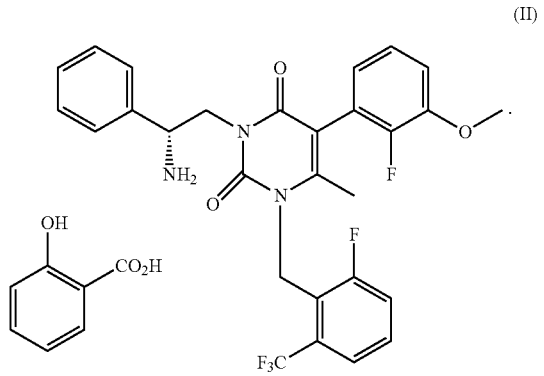 [SMILES: O=C(O)c1ccccc1O ; COc1cccc(-c2c(C)n(Cc3c(F)cccc3C(F)(F)F)c(=O)n(C[C@H](N)c3ccccc3)c2=O)c1F]

(II)

In some aspects, the process for preparing a substantially pure composition of Compound (I) comprises using, as an intermediate in the process, Compound (II); and reacting Compound (IIa),

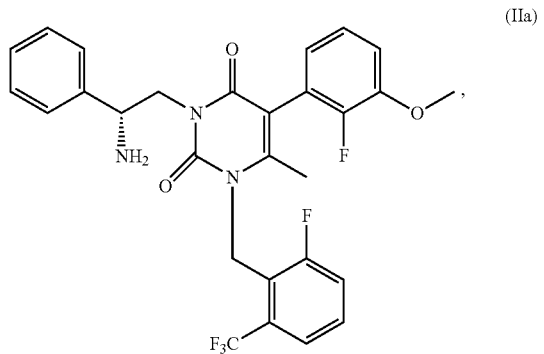 [SMILES: COc1cccc(-c2c(C)n(Cc3c(F)cccc3C(F)(F)F)c(=O)n(C[C@H](N)c3ccccc3)c2=O)c1F]

(IIa)

with salicylic acid to form Compound (II).

In other aspects, the process for preparing a substantially pure composition of Compound (I) comprises using, as an intermediate in the process, Compound (II); reacting Compound (IIa) with salicylic acid to form Compound (II); and isolating Compound (II) to provide an isolated Compound (II); wherein the isolated Compound (II) is in crystalline form.

In yet other aspects, the process for preparing a substantially pure composition of Compound (I) comprises using, as an intermediate in the process, Compound (II); reacting Compound (IIa) with salicylic acid to form Compound (II); reacting Compound (II) with a compound of formula (III),

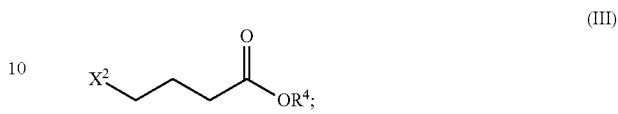

(III)

where $R^4$ is $C_1$-$C_8$ alkyl; $X^2$ is Cl, Br, I, $-OSO_2CH_3$, $-OSO_2C_6H_4CH_3$ or $-OSO_2CF_3$; and forming a compound of formula (IV),

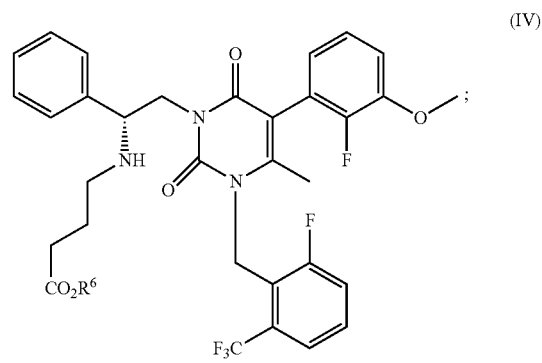

(IV)

where $R^6$ is $C_1$-$C_8$ alkyl.

In other aspects, the process for preparing a substantially pure composition of Compound (I) comprises using, as an intermediate in the process, Compound (II); reacting Compound (IIa) with salicylic acid to form Compound (II); reacting Compound (II) with a compound of formula (III), where $R^4$ is $C_1$-$C_8$ alkyl; $X^2$ is Cl, Br, I, $-OSO_2CH_3$, $-OSO_2C_6H_4CH_3$ or $-OSO_2CF_3$; forming a compound of formula (IV), where $R^6$ is $C_1$-$C_8$ alkyl; and treating a compound of formula (IV) with a sodium base to form Compound (I).

In one embodiment, a polymorphic form of Compound (II) is provided.

In one aspect, the polymorphic form of Compound (II) is crystalline.

In another aspect, the polymorphic form of Compound (II) is a crystalline solid substantially free of amorphous Compound (II).

In one aspect, the polymorphic form of Compound (II) is a solvated crystalline form.

In some aspects, the polymorphic form of Compound (II) is a solvated crystalline form; wherein the solvated crystalline form is solvated with methanol.

In one aspect, the polymorphic form of Compound (II) is a solvated crystalline form; wherein the solvated crystalline form is solvated with methanol; and wherein methanol is present in an amount from about 0.1 to 5.0 weight percent.

In one aspect, the polymorphic form of Compound (II) is a solvated crystalline form; wherein the solvated crystalline form is solvated with methanol; and the molar ratio of methanol to 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione is between about 0.1:1 and 1:1.

In one aspect, the polymorphic form of Compound (II) is a solvated crystalline form; wherein the solvated crystalline form is solvated with methanol; and the polymorphic form has an X-ray powder diffraction pattern comprising one or more peaks at ±0.2 of 7.0, 9.6, 10.7, 10.9, 11.4, 13.1, 13.5, 17.3, 17.5, and 18.2° 2θ, when measured at about 25° C. with Cu—$K_{\alpha 1}$ radiation at 1.5406 Å.

In one aspect, the polymorphic form of Compound (II) is a solvated crystalline form; wherein the solvated crystalline form is solvated with methanol; and the polymorphic form has an X-ray powder diffraction pattern comprising peaks at ±0.2 of 7.0, 9.6, and 11.4° 2θ, when measured at about 25° C. with Cu—$K_{\alpha 1}$ radiation at 1.5406 Å.

In some aspects, the polymorphic form of Compound (II) is a solvated crystalline form; wherein the solvated crystalline form is solvated with water.

In one aspect, the polymorphic form of Compound (II) is a solvated crystalline form; wherein the solvated crystalline form is solvated with water; and wherein water is present in an amount from about 0.1 to 5.0 weight percent.

In one aspect, the polymorphic form of Compound (II) is a solvated crystalline form; wherein the solvated crystalline form is solvated with water; and the molar ratio of water to 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione is between about 0.3:1 and 0.6:1.

In some aspects, the polymorphic form of Compound (II) is a solvated crystalline form; wherein the solvated crystalline form is solvated with water, and additionally solvated with a solvent other than water.

In one aspect, the polymorphic form of Compound (II) is a solvated crystalline form; wherein the solvated crystalline form is solvated with water, and additionally solvated with a solvent other than water; wherein the solvent other than water is methanol.

In one aspect, the polymorphic form of Compound (II) is a solvated crystalline form; wherein the solvated crystalline form is solvated with water, and additionally solvated with a solvent other than water; wherein the solvent other than water is methanol; and wherein the molar ratio of methanol to water is about 1:0.5.

In one aspect, the polymorphic form of Compound (II) is a solvated crystalline form; wherein the solvated crystalline form is solvated with water, and additionally solvated with a solvent other than water; wherein the solvent other than water is methanol; wherein the molar ratio of methanol to water is about 1:0.5; and the polymorphic form has an X-ray powder diffraction pattern comprising one or more peaks at ±0.2 of 6.0, 8.1, 8.7, 9.5, 9.8, 10.6, 12.2, 12.5, 13.1, and 14.5° 2θ, when measured at about 25° C. with Cu—$K_{\alpha 1}$ radiation at 1.5406 Å.

In one aspect, the polymorphic form of Compound (II) is a solvated crystalline form; wherein the solvated crystalline form is solvated with water, and additionally solvated with a solvent other than water; wherein the solvent other than water is methanol; wherein the molar ratio of methanol to water is about 1:0.5; and the polymorphic form has an X-ray powder diffraction pattern comprising peaks at ±0.2 of 6.0, 9.8, and 12.5° 2θ, when measured at about 25° C. with Cu—$K_{\alpha 1}$ radiation at 1.5406 Å.

In some aspects, the polymorphic form of Compound (II) is crystalline, wherein the crystalline form is a desolvated/dehydrated crystalline form.

In one aspect, the polymorphic form of Compound (II) is crystalline, wherein the crystalline form is a desolvated/dehydrated crystalline form, and the polymorphic form has an X-ray powder diffraction pattern comprising one or more peaks at ±0.2 of 6.1, 8.1, 8.7, 10.2, 10.4, 12.0, 13.1, 14.4, 16.6, and 17.4° 2θ, when measured at about 25° C. with Cu—$K_{\alpha 1}$ radiation at 1.5406 Å.

In another aspect, the polymorphic form of Compound (II) is crystalline, wherein the crystalline form is a desolvated/dehydrated crystalline form, and the polymorphic form has an X-ray powder diffraction pattern comprising peaks at ±0.2 of 10.2, 10.4, and 12.0° 2θ, when measured at about 25° C. with Cu—$K_{\alpha 1}$ radiation at 1.5406 Å.

In one embodiment, a composition of Compound (I) comprising Compound (I) and one or more impurities is provided; wherein the composition comprises at least about 97 weight percent of Compound (I) and not more than about 3 weight percent of the one or more impurities, wherein the composition is prepared by a process comprising, using Compound (II) as an intermediate.

In one aspect, a composition of Compound (I) comprising Compound (I) and one or more impurities is provided; wherein the composition comprises at least about 97 weight percent of Compound (I) and not more than about 3 weight percent of the one or more impurities, wherein the composition is prepared by a process comprising, using Compound (II) as an intermediate; and reacting Compound (IIa) with salicylic acid to form Compound (II).

In one aspect, a composition of Compound (I) comprising Compound (I) and one or more impurities is provided; wherein the composition comprises at least about 97 weight percent of Compound (I) and not more than about 3 weight percent of the one or more impurities, wherein the composition is prepared by a process comprising, using Compound (II) as an intermediate; reacting Compound (IIa) with salicylic acid to form Compound (II); and isolating Compound (II) to provide an isolated Compound (II).

In one aspect, a composition of Compound (I) comprising Compound (I) and one or more impurities is provided; wherein the composition comprises at least about 97 weight percent of Compound (I) and not more than about 3 weight percent of the one or more impurities, wherein the composition is prepared by a process comprising, using Compound (II) as an intermediate; and reacting Compound (IIa) with salicylic acid to form Compound (II); wherein the one or more impurities are selected from the group consisting of Compounds (i, ii, iii, iv, v, vi, vii, viii, ix, x, xv, xvi, xvii, xviii, and IIa).

In one embodiment, a compound of formula (VI) is provided,

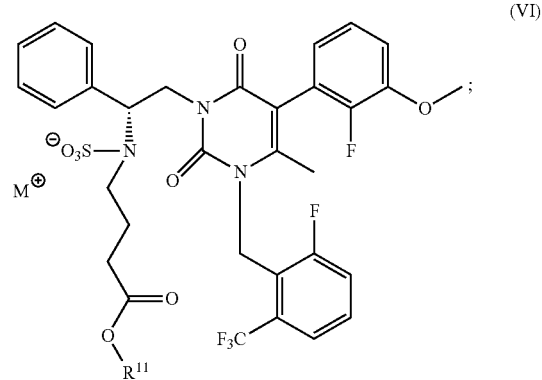

where

R$^{11}$ is selected from the group consisting of hydrogen, M', C$_1$-C$_6$ alkyl, C$_2$-C$_4$ alkenyl, C$_6$-C$_{10}$ aryl, 5-14 membered heteroaryl, J-(C$_6$-C$_{10}$ aryl), and J-(5-14 membered heteroaryl); wherein the C$_6$-C$_{10}$ aryl, 5-14 membered heteroaryl, J-(C$_6$-C$_{10}$ aryl), and J-(5-14 membered heteroaryl) may be optionally substituted with 1 to 4 substituents independently selected from the group consisting of halogen, nitro, cyano, hydroxy, C$_1$-C$_6$ alkyl, C$_1$-C$_6$ haloalkyl, C$_3$-C$_{11}$ cycloalkyl, 3-14 membered heterocyclyl, —OR$^a$, —NR$^a$R$^b$, —NR$^a$C(=O)R$^c$, —C(=O)R$^c$, —C(=O)OH, —C(=O)OR$^c$, —C(=O)NR$^a$R$^b$, —SO$_2$R$^c$, and —SO$_2$NR$^a$R$^b$;

R$^a$, and R$^b$ are each independently selected from the group consisting of hydrogen, C$_1$-C$_6$ alkyl, C$_6$-C$_{10}$ aryl, and 5-14 membered heteroaryl;

R$^c$ is selected from the group consisting of C$_1$-C$_6$ alkyl, C$_6$-C$_{10}$ aryl, and 5-14 membered heteroaryl;

J is C$_1$-C$_2$ alkylene;

M is selected from the group consisting of sodium, tetramethylguanidinium, 2,3,4,6,7,8,9,10-octahydropyrimido[1,2-a]azepinium, 3,4,6,7,8,9-hexahydro-2H-pyrido[1,2-a]pyrimidinium, and 2-hydroxyethan-1-aminium; and M' is selected from the group consisting of sodium, lithium, and potassium.

In one aspect, the compound of formula (VI) is provided which is the compound of formula (VIa),

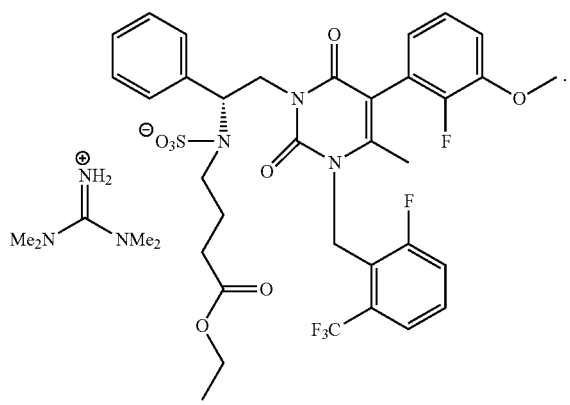

(VIa)

In another aspect, the compound of formula (VIa), is in crystalline form. The compound of formula (VIa) may be crystallized from a suitable solvent, including for example, 2-methyltetrahydrofuran, tetrahydrofuran or 2-propanol. Crystallization may be induced by heating a mixture of compound (VIa) and the solvent to an elevated temperature, and then cooling to a reduced temperature to afford crystallization. In some aspects, the mixture is heated to between about 50-70° C., and then cooled to between about ambient temperature and 0° C. In other aspects the mixture is heated to between about 50-70° C., and then cooled to ambient temperature and separated.

In yet another aspect, the compound of formula (VIa), is in crystalline form, and has an X-ray powder diffraction pattern comprising one or more peaks at ±0.2 of 6.1, 7.7, 8.9, 9.6, 10.7, 12.3, 14.7, 15.3, 16.6, 17.5, and 18.2° 2θ, when measured at about 25° C. with Cu—K$_{α1}$ radiation at 1.5406 Å.

In another aspect, the compound of formula (VIa), is in crystalline form, and has an X-ray powder diffraction pattern comprising peaks at ±0.2 of 6.1, 7.7, and 18.2° 2θ, when measured at about 25° C. with Cu—K$_{α1}$ radiation at 1.5406 Å.

In another aspect, the compound of formula (VIa), is in crystalline form, and has an X-ray powder diffraction pattern comprising one or more peaks at ±0.2 of 5.9, 6.7, 8.5, 9.3, 10.7, 11.1, 15.3, 16.0, 17.4, and 17.8° 2θ, when measured at about 25° C. with Cu—K$_{α1}$ radiation at 1.5406 Å.

In another aspect, the compound of formula (VIa), is in crystalline form, and has an X-ray powder diffraction pattern comprising peaks at ±0.2 of 5.9, 8.5, and 9.3° 2θ, when measured at about 25° C. with Cu—K$_{α1}$ radiation at 1.5406 Å.

In another aspect, the compound of formula (VIa), is in crystalline form, which is a solvated crystalline form that is solvated with water, and has an X-ray powder diffraction pattern comprising one or more peaks at ±0.2 of 6.0, 7.6, 8.9, 9.6, 10.7, 12.4, 14.8, 15.3, 16.6, 17.5, and 18.2° 2θ, when measured at about 25° C. with Cu—K$_{α1}$ radiation at 1.5406 Å.

In another aspect, the compound of formula (VIa), is in crystalline form, which is a solvated crystalline form that is solvated with water, and has an X-ray powder diffraction pattern comprising peaks at ±0.2 of 6.0, 7.6, and 18.2° 2θ, when measured at about 25° C. with Cu—K$_{α1}$ radiation at 1.5406 Å.

In another aspect, the compound of formula (VIa), is in crystalline form, which is a solvated crystalline form that is solvated with dimethyl sulfoxide, and has an X-ray powder diffraction pattern comprising one or more peaks at ±0.2 of 5.8, 7.3, 10.6, 12.1, 14.6, 15.0, 17.0, 17.5, 18.6, and 22.9° 2θ, when measured at about 25° C. with Cu—K$_{α1}$ radiation at 1.5406 Å.

In another aspect, the compound of formula (VIa), is in crystalline form, which is a solvated crystalline form that is solvated with dimethyl sulfoxide, and has an X-ray powder diffraction pattern comprising peaks at ±0.2 of 5.8, 7.3, and 17.5° 2θ, when measured at about 25° C. with Cu—K$_{α1}$ radiation at 1.5406 Å.

In yet another aspect, the compound of formula (VIa), is in crystalline form, which is a solvated crystalline form that is solvated with dichloromethane, and has an X-ray powder diffraction pattern comprising one or more peaks at ±0.2 of 5.9, 6.6, 8.4, 10.6, 11.7, 12.3, 14.8, 15.9, 17.6, 18.2, 18.9, and 20.7° 2θ, when measured at about 25° C. with Cu—K$_{α1}$ radiation at 1.5406 Å.

In another aspect, the compound of formula (VIa), is in crystalline form, which is a solvated crystalline form that is solvated with dichloromethane, and has an X-ray powder diffraction pattern comprising one or more peaks at ±0.2 of 11.7, 18.9, and 20.7° 2θ, when measured at about 25° C. with Cu—K$_{α1}$ radiation at 1.5406 Å.

In one embodiment, a compound of formula (VII) is provided,

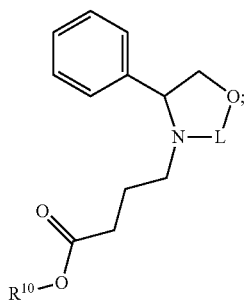

(VII)

where

R[10] is selected from the group consisting of sodium, lithium, potassium, hydrogen, $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —OR$^a$, —NR$^a$R$^b$, —NR$^a$C(=O)R$^c$, —C(=O)R$^c$, —C(=O)OH, —C(=O)OR$^c$, —C(=O)NR$^a$R$^b$, —SO$_2$R$^c$, and —SO$_2$NR$^a$R$^b$;

R$^a$, and R$^b$ are each independently selected from the group consisting of hydrogen and $C_1$-$C_6$ alkyl, $C_6$-$C_{10}$ aryl, and 5-14 membered heteroaryl;

R$^c$ is selected from the group consisting of $C_1$-$C_6$ alkyl, $C_6$-$C_{10}$ aryl, and 5-14 membered heteroaryl;

J is $C_1$-$C_2$ alkylene;

L is selected from the group consisting of —SO—, —SO$_2$—, and —P(O)OR$^{12}$; and R$^{12}$ is selected from the group consisting of hydrogen and $C_1$-$C_6$ alkyl.

In one aspect, a compound of formula (VII) is provided, where L is —SO$_2$—; and R$^{10}$ is $C_1$-$C_6$ alkyl.

In one embodiment, a process for preparing a substantially pure composition of Compound (I) is provided, comprising using as an intermediate in the process, a compound of formula (VI); and converting the compound of formula (VI) to Compound (I) by treatment with an acid and treatment with a first base.

In some aspects, the process for preparing a substantially pure composition of Compound (I) comprises using as an intermediate in the process, a compound of formula (VI); and converting the compound of formula (VI) to Compound (I) at a temperature between about 10 to 35° C. by treatment with an acid which has a pH between about 0.1 and 4.0, and treatment with a first base which comprises a sodium cation. In one embodiment, a composition of Compound (I) is provided, comprising, Compound (I), and one or more impurities, wherein the composition comprises at least about 97 weight percent of Compound (I) and not more than about 3 weight percent of the one or, more impurities, wherein the one or more impurities are selected from the group consisting of, compound (x), (xv), (xvi), (xvii) and (xviii).

In one embodiment, a composition of Compound (I) is provided, comprising Compound (I) and one or more impurities; wherein the composition comprises at least about 97 weight percent of Compound (I) and not more than about 3 weight percent of the one or more impurities; wherein the composition is prepared by a process comprising, using as an intermediate, Compound (VIa).

In one aspect, the composition of Compound (I) comprises Compound (I) and one or more impurities selected from the group consisting of compound (i, IIa, ii, iv, v, vi, vii, viii, ix, x and xviii); wherein the composition comprises at least about 97 weight percent of Compound (I) and not more than about 3 weight percent of the one or more impurities; wherein the composition is prepared by a process comprising, using as an intermediate, Compound (VIa).

BRIEF DESCRIPTION OF THE FIGURES

FIG. 6 is a TGA thermogram of Form C.
FIG. 7 is a DSC thermogram of Form C.

DETAILED DESCRIPTION OF THE INVENTION

Figure 1:
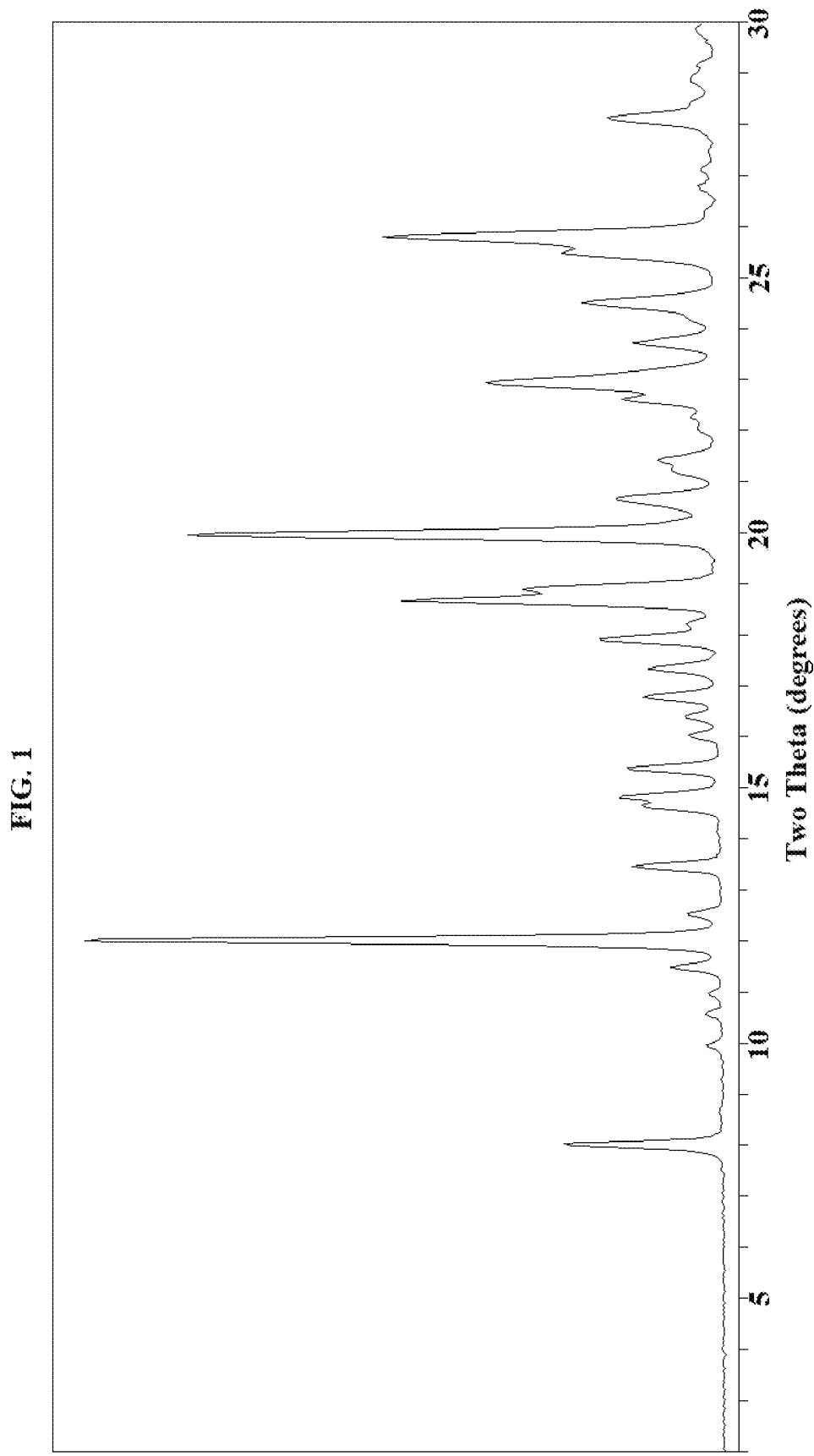
FIG. 1 is a powder X-ray diffraction pattern corresponding to Form A.

The present disclosure is directed, in part, to processes for preparing the sodium salt of elagolix, elagolix sodium (I):

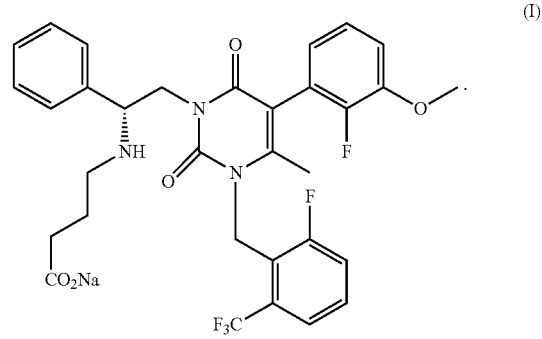

(I)

The processes for preparing elagolix sodium (I) are suitable for manufacturing the drug substance at commercial scale, with good manufacturing practices. The processes described herein for manufacture of elagolix sodium active substance, provides elagolix sodium (I) with a very low impurity profile. Low impurity includes and low mutagenic impurities, which are required by regulatory authorities. While maintaining a desirable impurity profile, the manufacturing process provides improved manufacturability and lower cost of goods for obtaining a substantially pure active substance suitable for commercial scale manufacturing.

The present disclosure is also directed, in part, to a process for preparing elagolix sodium (I) using Compound (II) as an intermediate in the process,

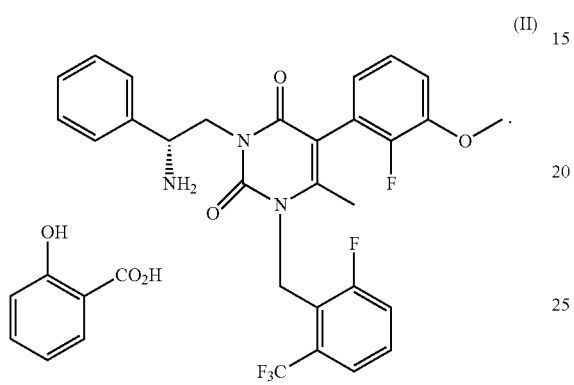

The present disclosure is also directed, in part, to a process for preparing elagolix sodium (I) using as an intermediate in the process, a compound of formula (VI),

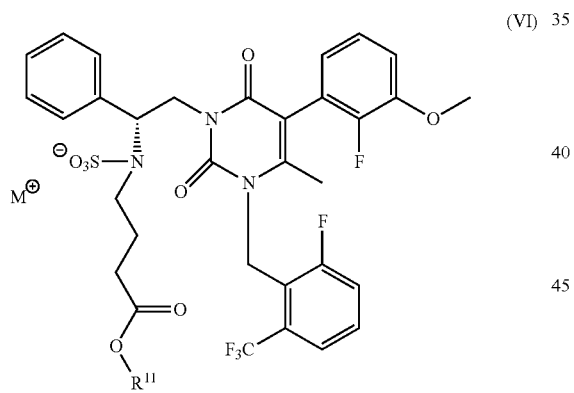

where $R^{11}$ is selected from the group consisting of $C_1$-$C_6$ alkyl, $C_6$ aryl, and J-($C_6$ aryl); J is $C_1$-$C_2$ alkylene; and M is selected from the group consisting of tetramethylguanidinium, 2,3,4,6,7,8,9,10-octahydropyrimido[1,2-a]azepinium, 3,4,6,7,8,9-hexahydro-2H-pyrido[1,2-a]pyrimidinium, and 2-hydroxyethan-1-aminium.

The processes described herein provide lower cost of goods with improved manufacturability for obtaining a substantially pure active substance that is suitable for commercial scale manufacturing. The desired product should be made using a process that affords exacting purity standards to meet regulatory requirements.

When purifying an intermediate at manufacturing scale, it is often preferable to do so via solid isolation, rather than liquid/liquid phase chemical manipulation including, for example, liquid-liquid extraction. Liquid-liquid extraction at manufacturing scale can be very inefficient for a number of reasons including, emulsion formation, long phase separation times, rag layer formation, difficulty defining layer separation, low throughput, and excess solvent waste.

Although Compound (IIa) has been isolated as a solid, formation of the solid is not preferable due to the tendency of Compound (IIa) to oil out of solution. When Compound (IIa) oils out of solution, then liquid/liquid separation may need to be employed which is difficult to carry out at large scale less than ideal process of liquid/liquid separation at manufacturing scale will be encountered.

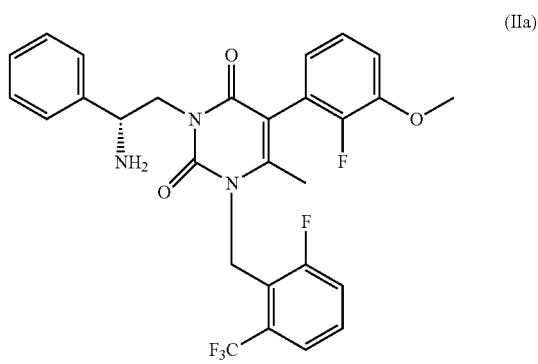 [SMILES: COc1cccc(-c2c(C)n(Cc3c(F)cccc3C(F)(F)F)c(=O)n(C[C@H](N)c3ccccc3)c2=O)c1F]

Applicant has surprisingly found a crystalline salt of Compound (IIa), specifically the salicylate salt, Compound (II). Numerous salts of Compound (IIa) were screened, but unexpectedly, the salicylate salt was found to afford crystalline material, including polymorphic forms. The process of synthesizing elagolix sodium by using Compound (II) as an intermediate afforded a significant advancement in the manufacturability of elagolix sodium, by reducing the number of liquid-liquid extractions of prior synthesis methods for preparing elagolix sodium, increasing purity at the stage of Compound (II) and thereby chemical purity of the final elagolix sodium, as well as enhancing operability and throughput of the process.

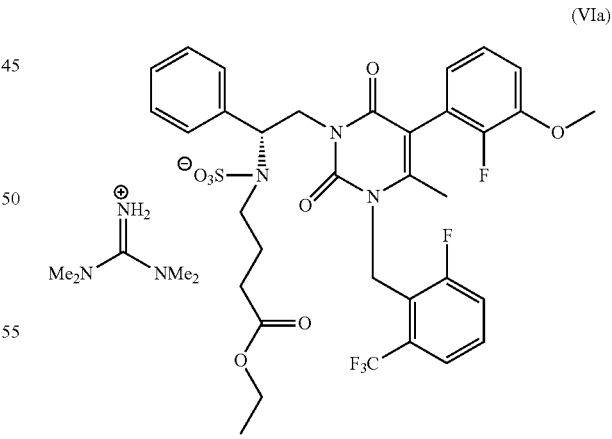

Another process for preparing elagolix sodium (I) disclosed herein, uses as an intermediate in the process, a compound of formula (VI). Compounds of formula (VI) are novel, and crystalline forms of Compound (VIa), are described herein. The process of synthesizing elagolix sodium by using Compound (VIa) as an intermediate afforded a significant advancement in the manufacturability of elagolix sodium, including reducing the number of steps of prior synthesis methods for preparing elagolix sodium, allowing for more efficient manufacturing cycle times, as well as reduced cost of starting materials. Cyrstalline intermediates improved isolation and purification efficiency as compared to amorphous intermediates. Such as, the crystalline intermediates of Compound (VIa) offered enhanced manufacturing throughput and operability in the synthesis of elagolix sodium.

Crystalline Compound (VIa), not only enhances operability at manufacturing scale, but also improves control of the impurity profile of elagolix sodium within a narrow specification of impurity. Compound (VIa) is the penultimate isolated intermediate in the synthesis.

This detailed description is intended only to acquaint others skilled in the art with this disclosure, its principles, and its practical application so that others skilled in the art may adapt and apply the disclosure in its numerous forms, as they may be best suited to the requirements of a particular use. This description and its specific examples are intended for purposes of illustration only. This disclosure, therefore, is not limited to the embodiments described in this patent application, and may be variously modified.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" refers to a single pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain radical. In some instances, the number of carbon atoms in an alkyl moiety is indicated by the prefix "$C_x$-$C_y$," or "$C_{x-y}$," wherein x is the minimum and y is the maximum number of carbon atoms in the substituent. Thus, for example, "$C_1$-$C_8$ alkyl" means an alkyl substituent containing from 1 to 8 carbon atoms. Representative examples of alkyl include, but are not limited to, methyl, ethyl, n-propyl, iso-propyl, n-butyl, sec-butyl, iso-butyl, tert-butyl, pentyl, hexyl, heptyl, and octyl. The terms "alkyl," "$C_1$-$C_4$ alkyl," "$C_{1-4}$ alkyl," $C_1$-$C_6$ alkyl," "$C_{1-6}$ alkyl," "$C_1$-$C_8$ alkyl," and "$C_{1-8}$ alkyl," used herein are unsubstituted, unless otherwise indicated.

The term "alkenyl," as used herein, refers to a straight or branched hydrocarbon chain radical containing at least one carbon-carbon double bond. Representative examples of alkenyl include, but are not limited to, ethenyl, 2-propenyl, 3-butenyl, and the like.

The term "alkylene" denotes a divalent group derived from a straight or branched chain hydrocarbon containing from 1 to 10 carbon atoms. Representative examples of alkylene include, but are not limited to, —$CH_2$—, and —$CH_2CH_2$—.

The term "aryl," as used herein, refers to a monocyclic, bicyclic, or a tricyclic fused hydrocarbon ring system radical wherein one or more of the hydrocarbon rings is aromatic. The bicyclic aryl is naphthyl, or a phenyl fused to a cycloalkyl, or a phenyl fused to a cycloalkenyl. The bicyclic aryl and tricyclic aryl are attached to the parent molecular moiety through any carbon atom contained within the ring system. Representative examples of the aryl groups include, but are not limited to, phenyl, dihydroindenyl, indenyl, naphthyl, dihydronaphthalenyl, tetrahydronaphthalenyl, and the like.

The term "cyano," as used herein, means a —CN group.

The term "cycloalkyl," as used herein, refers to a saturated hydrocarbon ring radical containing carbon ring atoms. The cycloalkyl may be a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptanyl, bicyclo[2.2.1]heptanyl, bicyclo[2.2.2]octanyl, bicyclo[3.2.2]nonanyl, bicyclo[3.3.1]nonanyl, and bicyclo[4.2.1]nonanyl, and the like. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic ring systems include, but are not limited to, tricyclo[3.3.1.03,7]nonanyl (octahydro-2,5-methanopentalenyl or noradamantanyl), and tricyclo[3.3.1.13,7]decanyl (adamantane), and the like. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octanyl.

The term "halo" or "halogen," as used herein, means Cl, Br, I, and F.

The term "haloalkyl," as used herein, refers to an alkyl group, as defined herein, in which one or more hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl, and the like.

The term "heteroaryl," as used herein, refers to an aromatic ring radical containing one or more heteroatoms or a ring system containing one or more heteroaryl rings. The monocyclic heteroaryl is a five- or six-membered ring. The five-membered ring contains two double bonds and one or more heteroatoms selected from O, S, and N. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl, and the like. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycloalkyl. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl, and the like.

The term "heterocycle" or "heterocyclyl" as used herein, refers to a hydrocarbon ring radical wherein at least one carbon atom is replaced by a heteroatom independently selected from the group consisting of O, N, and S. The heterocyclyl ring may be a single ring (monocyclic) or have two or more rings (bicyclic or polycyclic). Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered rings have from 0-3 double bonds. Representative examples of heterocyclyl monocyclic ring systems include, but are not limited to, azetidinyl, azepinyl, aziridinyl, diazepinyl, 1,3-dioxolanyl, dioxanyl, dithianyl, furanyl (furyl), imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, thiopyranyl, triazinyl, triazolyl, trithianyl, and the like. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothiophenyl, isoindolyl, isoindolinyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, thiopyranopyridinyl, and the like. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzofuranyl, dibenzothiophenyl, naphthofuranyl, naphthothiophenyl, oxanthrenyl, phenazinyl, phenoxathiinyl, phenoxazinyl, phenothiazinyl, thianthrenyl, thioxanthenyl, xanthenyl, and the like.

The term "hydroxy" or "hydroxyl" means —OH.

The term "impurity" or "impurities," as used herein, means those impurities specifically described herein, those derived from the process including reagents or solvents used in the process, intermediates used in the process, or degradants, including degradants of the compound synthesized in the process.

The term "nitro," as used herein means a —NO$_2$ group.

The term "nitrogen-protecting group," refers to groups intended to protect an amino group against undesirable reactions during synthetic procedures. Commonly used nitrogen-protecting groups are disclosed in Wuts, P. G. M. Greene's *Protective Groups in Organic Synthesis*, 5th ed.; John Wiley & Sons, Inc.: New Jersey, 2014, the entirety of which is hereby incorporated by reference. Deactivating nitrogen-protecting groups are those groups which delocalize electron density away from the nitrogen, thereby reducing the reactivity of the nitrogen lone pair of electrons by conjugation with another group such as, for example, a carbonyl or sulfonyl group. Preferred nitrogen-protecting groups are t-butyloxycarbonyl (Boc), and benzyloxycarbonyl (Cbz).

As used herein, the term "high yield," when used in reference to a reaction yield, refers to more than 75% yield by mole conversion, preferably more than 80% yield by mole conversion, more preferably more than 85% yield by mole conversion, even more preferably more than 90% yield by mole conversion, yet more preferably more than 95% yield by mole conversion, still more preferably more than 98% yield by mole conversion, yet still more preferably more than 99% yield by mole conversion, and yet still more preferably more than 99.5% yield by mole conversion.

As used herein, the term "substantially pure," when used in reference to a compound, refers to a preparation or composition where the preparation/composition contains more than 97% by weight of the compound, preferably more than 98% by weight of the compound, and more preferably more than 99% by weight of the compound.

Process for Preparing Elagolix Sodium

The processes described herein provide elagolix sodium (I) with high chemical purity and a very low chemical impurity profile, with control of mutagenic impurities. When performed at manufacturing scale, the process affords Compound (I) with a purity of at least about 95 weight percent. In some aspects, the process affords Compound (I) with a purity of at least about 97 weight percent. In some aspects, the purity is between about 97 and 99.9 weight percent. In other aspects, the Compound (I) purity is at least about 98 weight percent. In other aspects, the purity is between about 98 and 99.9 weight percent. In yet other aspects, the Compound (I) purity is at least about 99 weight percent. In other aspects, the purity is between about 99 and 99.9 weight percent.

In one embodiment, a composition of Compound (I) is provided comprising Compound (I) and one or more impurities. The composition of Compound (I) is a pharmaceutical composition. In some aspects, the composition is a solid pharmaceutical composition comprising Compound (I) and one or more impurities, wherein the composition comprises at least about 97 weight percent of Compound (I) and not more than about 3 weight percent of the one or more impurities.

In one embodiment, a composition of Compound (I) is provided which comprises Compound (I) and one or more impurities, wherein the composition comprises at least about 95 weight percent of Compound (I) and not more than about 5 weight percent of the one or more impurities. In some aspects, the composition may comprise Compound (I) and one or more impurities, wherein the composition comprises between about 95 and 99.9 weight percent of Compound (I) and between about 0.00000000001 and 5 weight percent of the one or more impurities. In some aspects, Compound (I) is amorphous.

In one embodiment, a composition of Compound (I) is provided which comprises Compound (I) and one or more impurities, wherein the composition comprises at least about 97 weight percent of Compound (I) and not more than about 3 weight percent of the one or more impurities. In some aspects, the composition may comprise Compound (I) and one or more impurities, wherein the composition comprises between about 97 and 99.9 weight percent of Compound (I) and between about 0.00000000001 and 3 weight percent of the one or more impurities. In some aspects, Compound (I) is amorphous.

In one embodiment, a composition of Compound (I) is provided which comprises Compound (I) and one or more impurities, wherein the composition comprises at least about 98 weight percent of Compound (I) and not more than about 2 weight percent of the one or more impurities. In some aspects, the composition may comprise Compound (I) and one or more impurities, wherein the composition comprises between about 98 and 99.9 weight percent of Compound (I) and between about 0.00000000001 and 2 weight percent of the one or more impurities. In some aspects, Compound (I) is amorphous.

In one embodiment, a composition of Compound (I) is provided which comprises Compound (I) and one or more impurities, wherein the composition comprises at least about 99 weight percent of Compound (I) and not more than about 1 weight percent of the one or more impurities. In some aspects, the composition may comprise Compound (I) and one or more impurities, wherein the composition comprises between about 99 and 99.9 weight percent of Compound (I) and between about 0.00000000001 and 1 weight percent of the one or more impurities. In some aspects, Compound (I) is amorphous.

In one embodiment, a composition of Compound (I) is provided which comprises Compound (I) and one or more impurities, wherein the composition comprises at least about 99.9 weight percent of Compound (I) and not more than about 0.1 weight percent of the one or more impurities. In some aspects, the composition may comprise Compound (I) and one or more impurities, wherein the composition comprises between about 99.9 and 99.99 weight percent of Compound (I) and between about 0.00000000001 and 0.1 weight percent of the one or more impurities. In some aspects, Compound (I) is amorphous.

In one embodiment, in the composition comprising Compound (I) and one or more impurities, the one or more impurities are selected from the group consisting of (i)

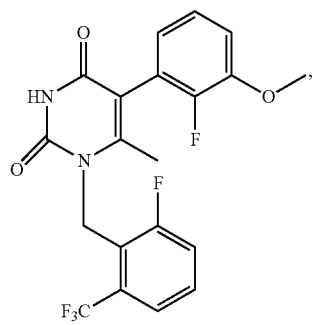

(IIa)

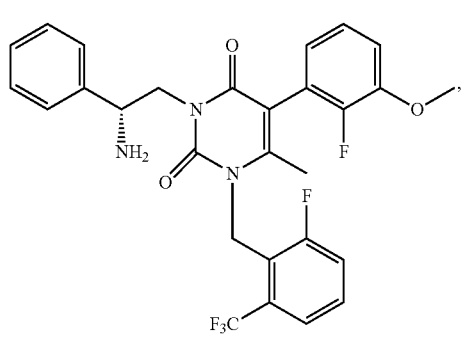

(ii)

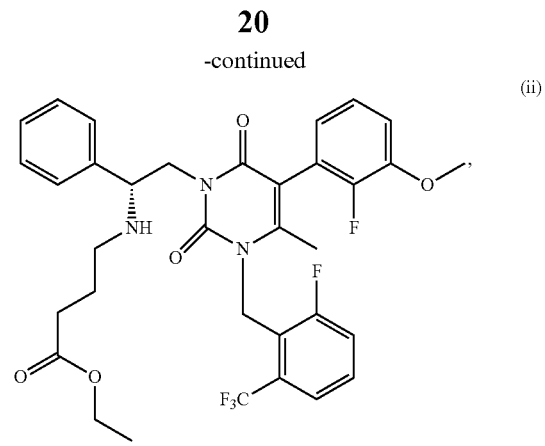

(iii)

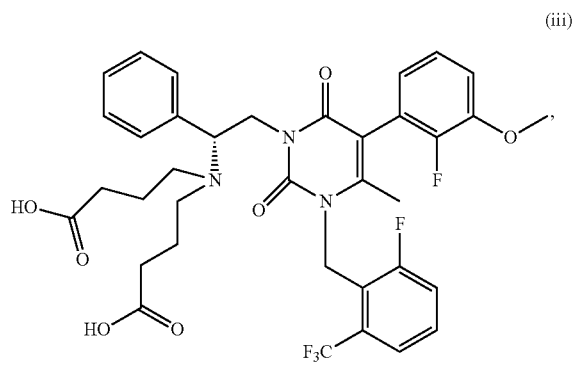

(iv)

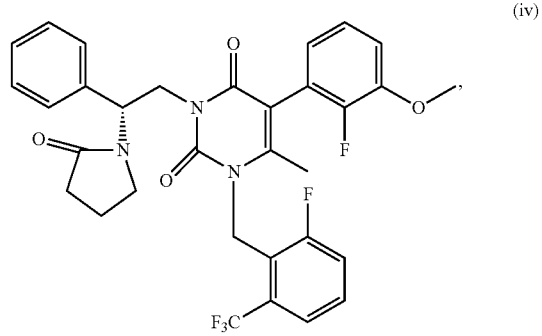

(v)

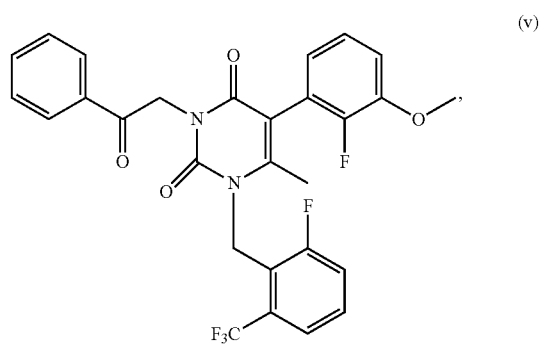

-continued (vi)
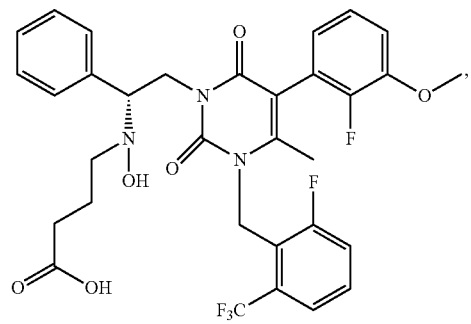

(vii)
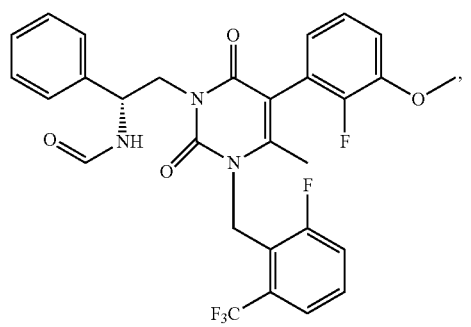

(viii)
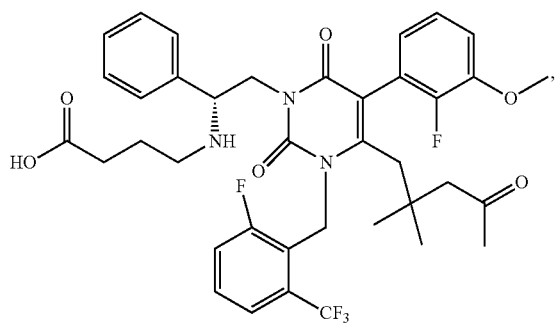

(ix)
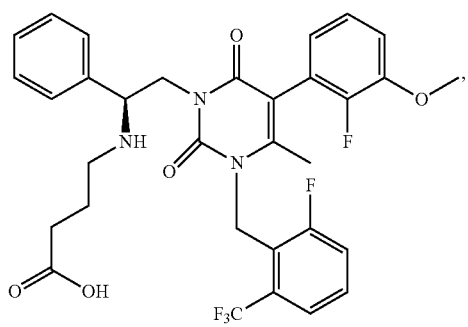

(x)
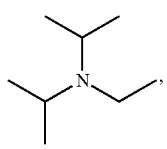

(xv)
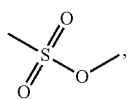

-continued (xvi)
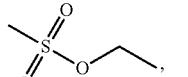

(xvii)
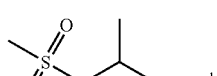, and (xviii)
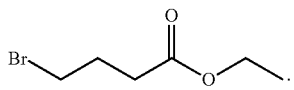.

In one embodiment of the composition comprising Compound (I) and an impurity, the impurity is a mutagenic impurity. The composition comprises no more than about 3 ppm of the mutagenic impurity. In some aspects, composition comprises between about 0.0000001 and 3 ppm of the mutagenic impurity. The mutagenic impurity may be selected from the group consisting of (xv)
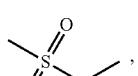, (xvi)
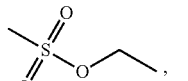, (xvii)
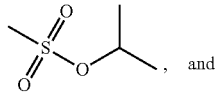, and (xviii)
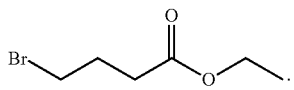.

In one embodiment of the composition comprising Compound (I) and a mutagenic impurity, each of the mutagenic impurities is present in not more than about 3 ppm. In one aspect, each of the mutagenic impurities in present between about 0.0000001 and 3 ppm. In another embodiment, the sum of the mutagenic impurities is not more than about 10 ppm. In one aspect, the sum of the mutagenic impurities is between about 0.0000001 ppm and 10 ppm. The mutagenic impurities may be selected from the group consisting of Compounds (xv, xvi, xvii and xviii). The amount of impurities (xv, xvi, and xvii) may be determined using LC-MS Method D. The amount of impurity (xviii) may be determined using GC-MS Method E.

In one embodiment, a composition of Compound (I) is provided which comprises Compound (I) and one or more impurities selected from the group consisting of Compounds (i, ii, iii, iv, v, vi, vii, viii, ix, x, xv, xvi, xvii, xviii, and IIa), wherein the composition comprises at least about 97 weight percent of Compound (I) and not more than about 3 weight percent of the one or more impurities. In some aspects, the composition comprises Compound (I) and one or more impurities selected from the group consisting of Compounds (i, ii, iii, iv, v, vi, vii, viii, ix, x, xv, xvi, xvii, xviii, and IIa), wherein the composition comprises between about 97 and 99.9 weight percent of Compound (I) and between about 0.00000000001 and 3 weight percent of the one or more impurities. In some aspects, Compound (I) is amorphous.

In one embodiment, a composition of Compound (I) is provided which comprises Compound (I) and one or more impurities selected from the group consisting of Compounds (i, ii, iii, iv, v, vi, vii, viii, ix, x, xv, xvi, xvii, xviii, and IIa), wherein the composition comprises at least about 98 weight percent of Compound (I) and not more than about 2 weight percent of the one or more impurities selected from the group consisting of Compounds (i, ii, iii, iv, v, vi, vii, viii, ix, x, xv, xvi, xvii, xviii, and IIa). In some aspects, the composition may comprise Compound (I) and one or more impurities, wherein the composition comprises between about 98 and 99.9 weight percent of Compound (I) and between about 0.00000000001 and 2 weight percent of the one or more impurities. In some aspects, Compound (I) is amorphous.

In one embodiment, a composition of Compound (I) is provided which comprises Compound (I) and one or more impurities selected from the group consisting of Compounds (i, ii, iii, iv, v, vi, vii, viii, ix, x, xv, xvi, xvii, xviii, and IIa), wherein the composition comprises at least about 99 weight percent of Compound (I) and not more than about 1 weight percent of the one or more impurities selected from the group consisting of Compounds (i, ii, iii, iv, v, vi, vii, viii, ix, x, xv, xvi, xvii, xviii, and IIa). In some aspects, the composition may comprise Compound (I) and one or more impurities, wherein the composition comprises between about 99 and 99.9 weight percent of Compound (I) and between about 0.00000000001 and 1 weight percent of the one or more impurities. In some aspects, Compound (I) is amorphous.

In one embodiment, a composition of Compound (I) is provided which comprises Compound (I) and one or more impurities selected from the group consisting of Compounds (i, ii, iii, iv, v, vi, vii, viii, ix, x, xv, xvi, xvii, xviii, and IIa), wherein the composition comprises at least about 99.9 weight percent of Compound (I) and not more than about 0.1 weight percent of the one or more impurities selected from the group consisting of Compounds (i, ii, iii, iv, v, vi, vii, viii, ix, x, xv, xvi, xvii, xviii, and IIa). In some aspects, the composition may comprise Compound (I) and one or more impurities, wherein the composition comprises between about 99.9 and 99.99 weight percent of Compound (I) and between about 0.00000000001 and 0.1 weight percent of the one or more impurities. In some aspects, Compound (I) is amorphous.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (i). In some aspects, the composition comprises between about 0.00000000001 and 3 weight percent of Compound (i). In other aspects, the composition comprises Compound (I) and one or more impurities, wherein the composition comprises at least about 97 weight percent of Compound (I) and not more than about 0.15 weight percent of the one or more impurities which is Compound (i). In some aspects, the composition comprises between about 0.00000000001 and 0.15 weight percent of Compound (i). The amount of Compound (i) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (IIa). In some aspects, the composition comprises Compound (I) and one or more impurities, wherein the composition comprises at least about 97 weight percent of Compound (I) and not more than about 0.70 weight percent of the one or more impurities which is Compound (IIa). In some aspects, the composition comprises between about 0.00000000001 and 0.70 weight percent of Compound (IIa). In other aspects, the composition comprises Compound (I) and one or more impurities, wherein the composition comprises at least about 97 weight percent of Compound (I) and not more than about 0.25 weight percent of the one or more impurities which is Compound (IIa). In some aspects, the composition comprises between about 0.00000000001 and 0.25 weight percent of Compound (IIa). The amount of Compound (IIa) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (ii). In some aspects, the composition comprises Compound (I) and one or more impurities, wherein the composition comprises at least about 97 weight percent of Compound (I) and not more than about 0.15 weight percent of the one or more impurities which is Compound (ii). In some aspects, the composition comprises between about 0.00000000001 and 0.15 weight percent of Compound (ii). The amount of Compound (ii) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (iii). In some aspects, the composition comprises Compound (I) and one or more impurities, wherein the composition comprises at least about 97 weight percent of Compound (I) and not more than about 0.25 weight percent of the one or more impurities which is Compound (iii). In some aspects, the composition comprises between about 0.00000000001 and 0.25 weight percent of Compound (iii). The amount of Compound (iii) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (iv). In some aspects, the composition comprises Compound (I) and one or more impurities, wherein the composition comprises at least about 97 weight percent of Compound (I) and not more than about 0.30 weight percent of the one or more impurities which is Compound (iv). In some aspects, the composition comprises between about 0.00000000001 and 0.30 weight percent of Compound (iv). The amount of Compound (iv) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (v). In some aspects, the composition comprises Compound (I) and one or more impurities, wherein the composition comprises at least about 97 weight percent of Compound (I) and not more than about 0.55 weight percent of the one or more impurities which is Compound (v). In some aspects, the composition comprises between about 0.00000000001 and 0.55 weight percent of Compound (v). The amount of Compound (v) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (vi). In some aspects, the composition comprises Compound (I) and one or more impurities, wherein the composition comprises at least about 97 weight percent of Compound (I) and not more than about 0.40 weight percent of the one or more impurities which is Compound (vi). In some aspects, the composition comprises between about 0.00000000001 and 0.40 weight percent of Compound (vi). The amount of Compound (vi) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (vii). In some aspects, the composition comprises Compound (I) and one or more impurities, wherein the composition comprises at least about 97 weight percent of Compound (I) and not more than about 0.35 weight percent of the one or more impurities which is Compound (vii). In some aspects, the composition comprises between about 0.00000000001 and 0.35 weight percent of Compound (vii). The amount of Compound (vii) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (viii). In some aspects, the composition comprises Compound (I) and one or more impurities, wherein the composition comprises at least about 97 weight percent of Compound (I) and not more than about 0.15 weight percent of the one or more impurities which is Compound (viii). In some aspects, the composition comprises between about 0.00000000001 and 0.15 weight percent of Compound (viii). The amount of Compound (viii) in the composition may be determined using HPLC method B.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (ix). In some aspects, the composition comprises Compound (I) and one or more impurities, wherein the composition comprises at least about 97 weight percent of Compound (I) and not more than about 0.2 weight percent of the one or more impurities which is Compound (ix). In some aspects, the composition comprises between about 0.00000000001 and 0.2 weight percent of Compound (ix). The amount of Compound (ix) in the composition may be determined using HPLC method G.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (x). In some aspects, the composition comprises Compound (I) and one or more impurities, wherein the composition comprises at least about 97 weight percent of Compound (I) and not more than about 25 ppm of the one or more impurities which is Compound (x). In some aspects, the composition comprises between about 0.0000001 and 25 ppm of Compound (x). The amount of Compound (x) in the composition may be determined using GC-MS method F.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (xv). In some aspects, the composition comprises Compound (I) and one or more impurities, wherein the composition comprises at least about 97 weight percent of Compound (I) and not more than about 0.6 ppm of the one or more impurities which is Compound (xv). In some aspects, the composition comprises between about 0.0000001 and 0.6 ppm of Compound (xv). The amount of Compound (xv) in the composition may be determined using LC-MS method D.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (xvi). In some aspects, the composition comprises Compound (I) and one or more impurities, wherein the composition comprises at least about 97 weight percent of Compound (I) and not more than about 0.9 ppm of the one or more impurities which is Compound (xvi). In some aspects, the composition comprises between about 0.0000001 and 0.9 ppm of Compound (xvi). The amount of Compound (xvi) in the composition may be determined using LC-MS method D.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (xvii). In some aspects, the composition comprises Compound (I) and one or more impurities, wherein the composition comprises at least about 97 weight percent of Compound (I) and not more than about 2.5 ppm of the one or more impurities which is Compound (xvii). In some aspects, the composition comprises between about 0.0000001 and 2.5 ppm of Compound (xvii). The amount of Compound (xvii) in the composition may be determined using LC-MS method D.

In one embodiment, a composition of Compound (I) is provided which comprises Compound (I) and one or more impurities, wherein the composition comprises at least about 97 weight percent of Compound (I) and not more than about 3 weight percent of the one or more impurities, wherein the one or more impurities is Compound (xviii). In some aspects, the composition comprises Compound (I) and one or more impurities, wherein the composition comprises at least about 97 weight percent of Compound (I) and not more than about 2.5 ppm of the one or more impurities which is Compound (xviii). In some aspects, the composition comprises between about 0.0000001 and 2.5 ppm of Compound (xviii). The amount of Compound (xviii) in the composition may be determined using GC-MS method E.

Synthesis of Elagolix

In general, the sodium salt of elagolix may be prepared as illustrated in the following reaction schemes. As shown in Scheme 1, intermediate (1-5) can be prepared from compound (1-1) via compounds of formula (1-3) where $R^1$ is bromo or iodo which are described in International Published Application WO2005007164 and U.S. Pat. No. 8,765,948, respectively. Fluorobenzotrifluoride (1-1) can be lithiated with a suitable base including, for example, lithium diisopropylamide at reduced temperature, followed by treatment with N,N-dimethylformamide to afford an aldehyde. The aldehyde can be converted to the corresponding oxime via treatment with hydroxylamine which is reduced to the corresponding primary amine under suitable conditions known to one skilled in the art including for example, treatment with zinc under acidic conditions. The primary amine can be treated with urea under conditions known to one skilled in the art to afford compound (1-2).

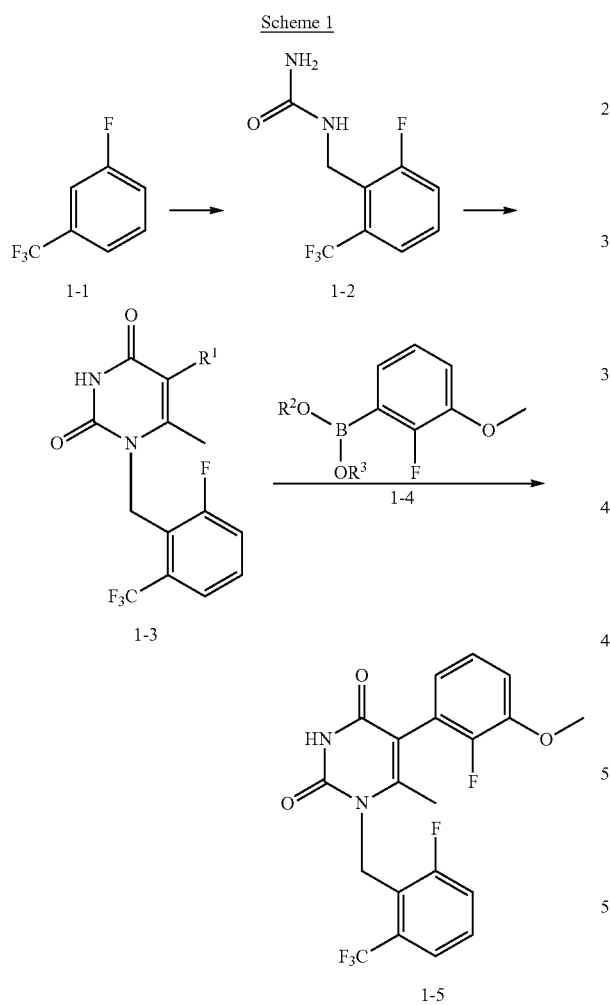

Compounds of formula (1-3) where $R^1$ is bromo or iodo may be prepared from compounds of formula (1-2) as described in International Published Application WO2005007164 and U.S. Pat. No. 8,765,948, respectively. Compounds of formula (1-3) may be coupled with a compound of formula (1-4) where $R^2$ and $R^3$ are each independently hydrogen or $C_1$-$C_4$ alkyl; or where $R^2$ and $R^3$ together may form a $C_1$-$C_4$ alkylene to form compound (1-5). The coupling reaction is performed in the presence of a suitable palladium catalyst, a suitable ligand, and suitable base. Examples of suitable palladium catalysts include, but are not limited to $Pd_2(dba)_3$, $Pd(OAc)_2$ and $Pd(PBu_3)_2$. Examples of suitable ligands for the palladium catalyst include, but are not limited to 4-(di-tert-butylphosphanyl)-N,N-dimethylaniline, and tri-tert-butylphosphine. Suitable bases include but are not limited to potassium hydroxide, and sodium hydroxide. The reaction is performed in a suitable solvent including, for example, 1,4-dioxane/water or acetone/water at elevated temperature, such as, for example 50-95° C.

As shown in Scheme 2, compounds of formula (II) may be prepared from compound (1-5). Compound (1-5) may be treated with a compound of formula (2-1) where $X^1$ is a suitable leaving group such as chloro, bromo, iodo, —$OSO_2CH_3$, —$OSO_2CF_3$, and —$OSO_2C_6H_4CH_3$, and $PG^1$ is any suitable nitrogen-protecting group such as those disclosed in Wuts, P. G. M. Greene's Protective Groups in Organic Synthesis, 5th ed.; John Wiley & Sons, Inc.: New Jersey, 2014, the entirety of which is hereby incorporated by reference, including, for example, —$CO_2C(CH_3)_3$, —$CO_2CH_2C_6H_5$, or other suitable deactivating nitrogen-protecting group to form a compound of formula (2-2). The reaction is performed in the presence of a suitable base including, for example, potassium carbonate, or tetramethyl guanidine, in a suitable solvent, including, for example N,N-dimethylformamide at elevated temperature such as 30-55° C.

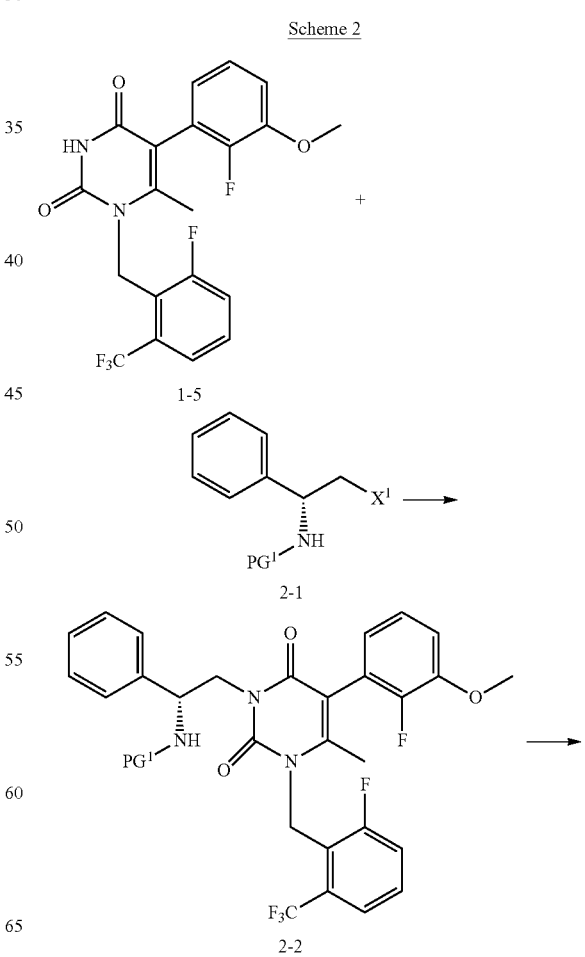

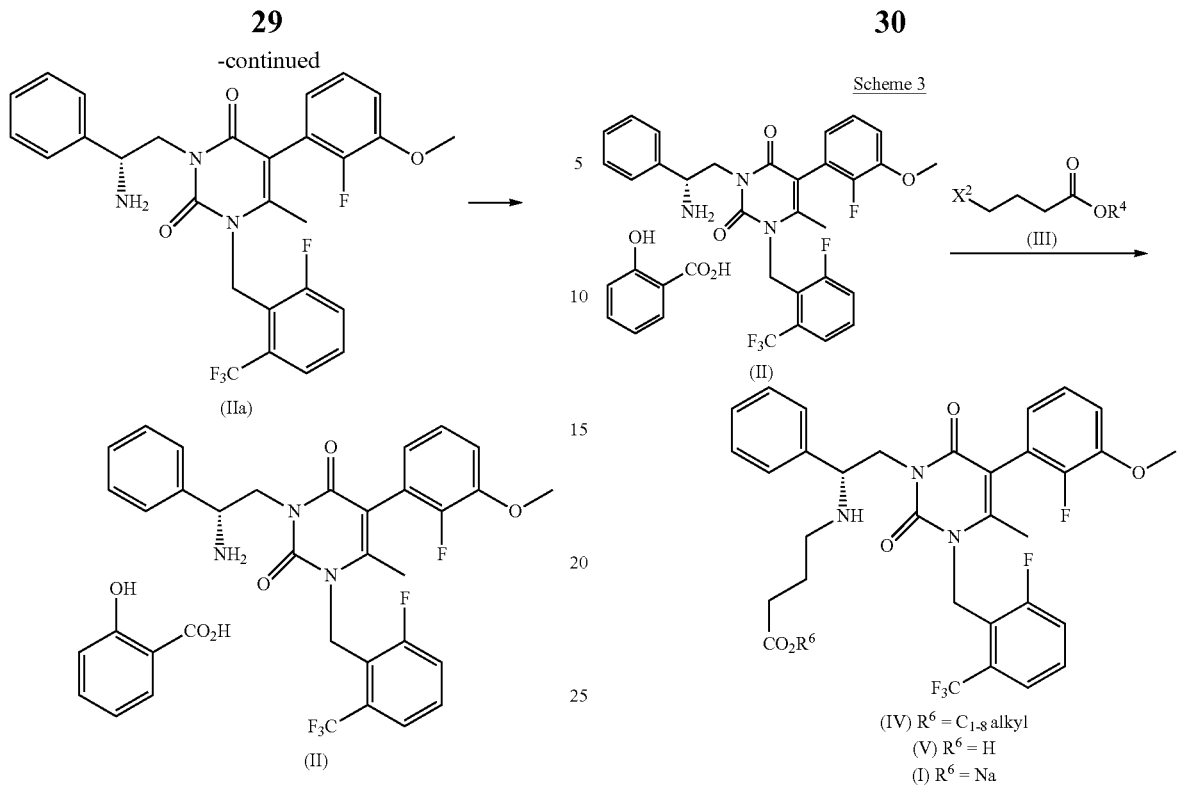

Compounds of formula (2-2) are deprotected to form the free amine compound (IIa). Compounds of formula (2-2) may be deprotected under suitable conditions for the specific protecting group. For example, when $PG^1$ is —$CO_2C(CH_3)_3$, an acid may be used to remove the protecting group. Suitable acids include, but are not limited to trifluoroacetic acid, hydrochloric acid, and methanesulfonic acid. The reaction is performed in a suitable solvent such as isopropyl acetate or isopropyl acetate/water at elevated temperature, for example 50-80° C. The free amine can be used directly in the next step or crystallized and isolated, if desired.

Compound (IIa) is treated with salicylic acid to form the salicylate salt, Compound (II). The salicylate salt may be isolated from the reaction mixture. The salicylate salt may be isolated in solid form. For example, the solid may be precipitated from a suitable solvent mixture including, but not limited to methanol and water. In other embodiments, the salicylate salt is isolated in crystalline form. Crystallization may be induced by adding crystalline seeds of the salicylate salt to assist the crystallization process.

As shown in Scheme 3, elagolix sodium may be prepared from salicylate salt (II). The salicylate salt (II) is converted to the free amine by treatment with a base including for example, sodium hydroxide and potassium hydroxide, and then reacted in the presence of a suitable base with a butyrate of formula (III), where $R^4$ is $C_1$-$C_8$ alkyl; and $X^2$ is a leaving group, to afford a compound of formula (IV), where $R^6$ is $C_1$-$C_8$ alkyl. $X^2$ may be selected from the group consisting of Cl, Br, I, —$OSO_2CH_3$, —$OSO_2C_6H_4CH_3$ and —$OSO_2CF_3$. Suitable bases for the alkylation reaction include, but are not limited to N,N-diisopropylethylamine. Suitable solvents include, but are not limited to N,N-dimethylformamide and N,N-dimethylacetamide. The reaction is performed at elevated temperature such as greater than 50° C., for example.

Compounds of formula (IV) may be hydrolyzed directly to Compound (I) in the presence of a sodium base such as sodium hydroxide. Alternatively, the compound of formula (V) can be formed via ester hydrolysis of compounds of formula (IV). Compound (V) may be converted to Compound (I) via treatment with a sodium base.

Alternatively, the sodium salt of elagolix may be prepared via intermediates of formula (VI) where $R^{11}$ is $C_1$-$C_6$ alkyl, $C_6$ aryl, or J-($C_6$ aryl); J is $C_1$-$C_2$ alkyl; and M is tetramethylguanidinium, 2,3,4,6,7,8,9,10-octahydropyrimido[1,2-a]azepinium, 3,4,6,7,8,9-hexahydro-2H-pyrido[1,2-a]pyrimidinium, or 2-hydroxyethan-1-aminium, and the like. As shown in Scheme 4, intermediate (VI) can be prepared from compound (1-5) via nucleophilic displacement of compounds of formula (VIIb) where $R^{10}$ is $C_1$-$C_6$ alkyl, $C_6$ aryl, or J-($C_6$ aryl); and J is $C_1$-$C_2$ alkyl; in the presence of a suitable base, including, but not limited to guanidines (including, for example, tetramethylguanidine, and the like), amidines (including, for example, 2,3,4,6,7,8,9,10-octahydropyrimido[1,2-a]azepine, 3,4,6,7,8,9-hexahydro-2H-pyrido[1,2-a]pyrimidine, and the like), substituted or unsubstituted trialkylamines (including, for example, triethylamine, trimethylamine, N, N-diisopropylethylamine, 2-hydroxyethan-1-amine, and the like), and other suitable amine bases known to one skilled in the art.

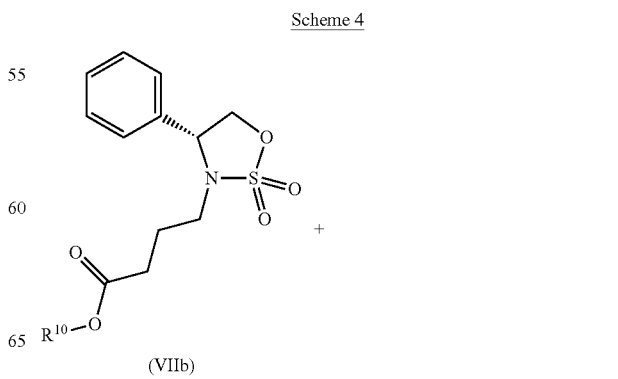

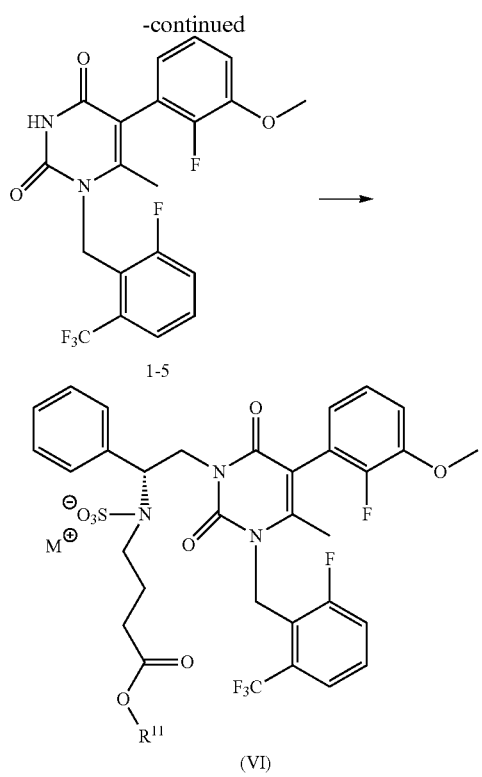

Compounds of formula (VIIb) may be prepared from Compound (5-1). Compound (5-1) may be treated with sulfuryl dichloride in the presence of a base to form Compound (5-2). Compound (5-2) may be alkylated in the presence of a suitable base with compounds of formula (5-3) where $R^{10}$ is $C_1$-$C_6$ alkyl, $C_6$ aryl, or J-($C_6$ aryl); J is $C_1$-$C_2$ alkyl, and $X^3$ is a suitable leaving group. Suitable $X^3$ groups include, but are not limited to, chloro, bromo, iodo, $-OSO_2CH_3$, $-OSO_2CF_3$, and $-OSO_2C_6H_4CH_3$. Alternatively, Compound (5-1) may be alkylated at elevated temperature with Compound (5-3) in the presence of a suitable amine base for example, but not limited to, N,N,-diisopropylethylamine and triethylamine, to afford compounds of formula (5-4). Compound (VIIa) may be prepared by treating Compound (5-4) with thionyl chloride at reduced temperature in the presence of a suitable base for example, but not limited to, N,N,-diisopropylethylamine, pyridine, and triethylamine, and a catalyst such as, for example, 4-(dimethylamino)pyridine. Compound (VIIa) may be oxidized to Compound (VIIb) under suitable oxidation conditions including, for example, ruthenium trichloride hydrate and sodium hypochlorite at ambient temperature.

Scheme 5

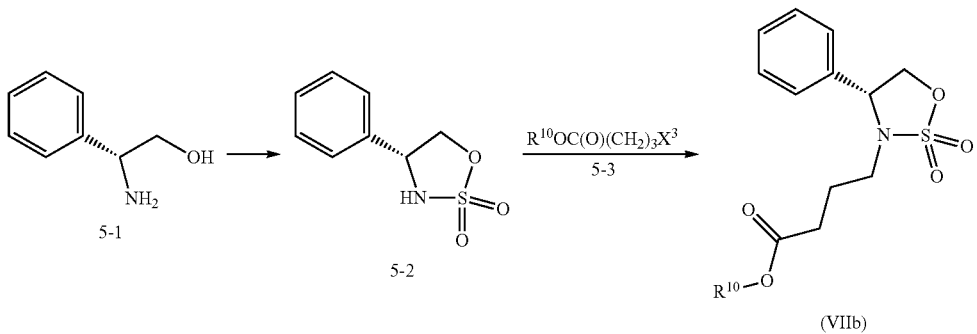

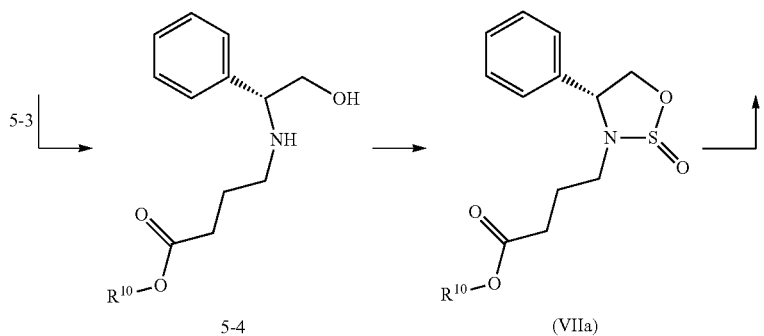

Compounds of formula (VI) where $R^{11}$ is $C_1$-$C_6$ alkyl, $C_6$ aryl, or J-($C_6$ aryl); J is $C_1$-$C_2$ alkyl; and M is tetramethylguanidinium, 2,3,4,6,7,8,9,10-octahydropyrimido[1,2-a]azepinium, 3,4,6,7,8,9-hexahydro-2H-pyrido[1,2-a]pyrimidinium, or 2-hydroxyethan-1-aminium, may be hydrolyzed in the presence of a sodium base such as sodium hydroxide. Treatment with aqueous acid such as HCl to neutralize the salt, followed by addition of a sodium base such as sodium carbonate affords Compound (I). Alternatively, the Compound of formula (VI) may be treated with an acid first to neutralize the salt, followed by treatment with a sodium base such as sodium hydroxide or sodium carbonate to afford Compound (I).

Scheme 6

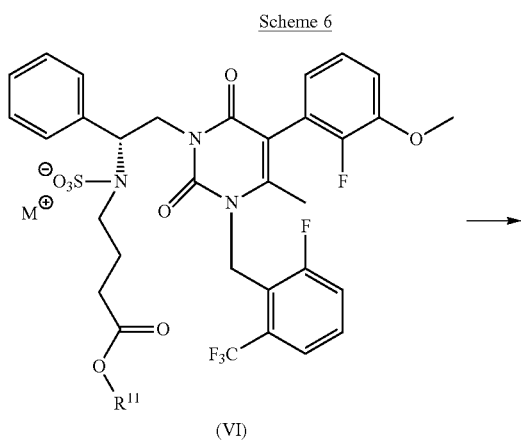

In one embodiment, the process of preparing substantially pure elagolix sodium in comprises, using as an intermediate in the process, a salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione (II):

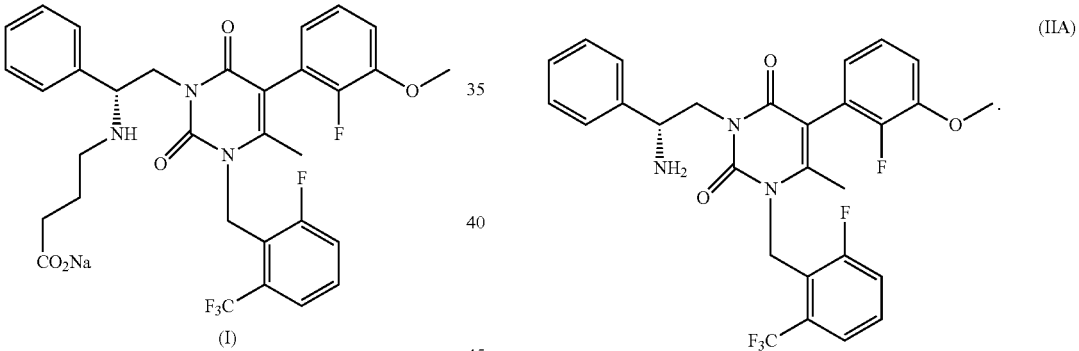

The salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione, Compound (II), is formed by reacting salicylic acid with 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione.

In some aspects, isolated Compound (II) is provided. For example, the salicylate salt may be precipitated from solution and isolated as a solid. In some aspects, Compound (II) in amorphous form is provided. In other aspects, Compound (II) in crystalline form is provided. Suitable solvent systems in which the salicylate salt may be precipitated from include, but are not limited to, water, methanol, 2-propanol, ethanol, dichloromethane, acetonitrile, acetone, toluene, heptanes, ethyl acetate, iso-propyl acetate, formamide, N,N-dimethylformamide, tetrahydrofuran, 2-methyl-tetrahydrofuran, methyl tert-butyl ether, methyl ethyl ketone, and dimethyl sulfoxide, and also includes binary systems including, but not limited to methanol/water, 2-propanol/water, acetonitrile/water, methyl tert-butyl ether/iso-propyl acetate, and ethyl acetate/heptanes. The salicylate salt may be precipitated from the solvent system as an amorphous solid, crystalline solid, or mixture thereof. In other aspects, the salt may be used without isolating it, but instead used directly in the next step of the process.

Compound (II) prepared by the methods disclosed herein provides material comprising between about 72.5 and about 83.0 weight percent of Compound (IIa),

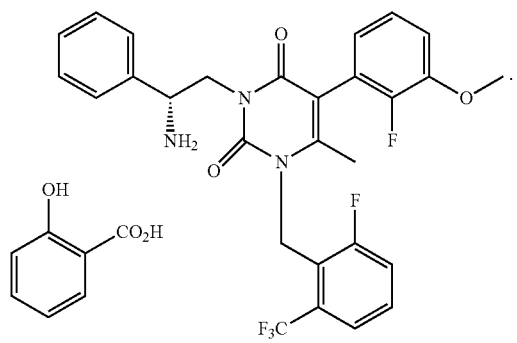

In some aspects, Compound (II) is provided comprising between about 76.5 and about 82.0 weight percent of Compound (IIa). In other aspects, Compound (II) is provided comprising between about 79.0 and about 81.0 weight percent of Compound (IIa). In yet other aspects, Compound (II) is provided comprising between about 79.5 and about 80.5 weight percent of Compound (IIa). The weight percent assay of Compound (IIa) in a sample of Compound (II), may be determined using HPLC Method A, a high purity standard of Compound (IIa), and standard weight percent calculations as known to one skilled in the art.

In one embodiment, a composition comprising Compound (II) and one or more impurities is provided. In one aspect, a composition comprising Compound (II) and one or more impurities is provided, wherein the composition comprises between about 72.5 and about 83.0 weight percent of Compound (IIa). In some aspects, the composition comprises between about 76.5 and about 82.0 weight percent of Compound (IIa). In other aspects, the composition comprises between about 79.0 and about 81.0 weight percent of Compound (IIa). In yet other aspects, the composition comprises between about 79.5 and about 80.5 weight percent of Compound (IIa). The weight percent assay of Compound (IIa) in a sample of Compound (II) may be determined using HPLC Method A, a high purity standard of Compound (IIa), and standard weight percent calculations as known to one skilled in the art.

In one embodiment, a composition comprising Compound (II) and an impurity is provided. The impurity is not more than about 7.5% peak area as determined by HPLC Method A. In other aspects, the impurity is not more than about 6% peak area as determined by HPLC Method A. HPLC Method A as disclosed herein is used for determining the impurity levels in the composition. Individual impurity levels are determined by calculating the peak area (PA) percentage according to the following formula:

$$\text{Individual Impurity Peak Area \%} = 100 \times \frac{PA \text{ Impurity}}{PA \text{ Total}}$$

$PA_{Impurity}$=peak area of individual impurity in sample $PA_{Total}$=sum of all peak areas in the sample equal to or greater than 0.05 peak area %, excluding the salicylic acid peak.

The methods for preparing Compound (II) disclosed herein also provide for control of the levels of impurities. In the composition comprising Compound (II) and one or more impurities, the one or more impurities may be selected from the group consisting of

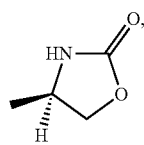
(xi)

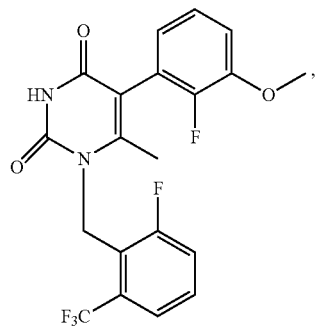
(i)

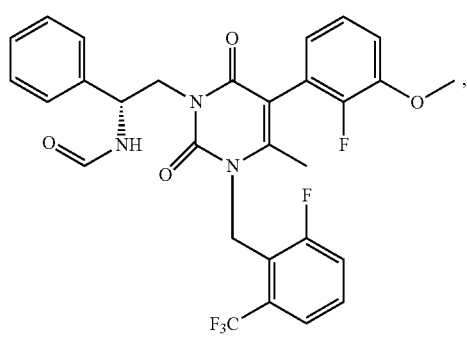
(xii)

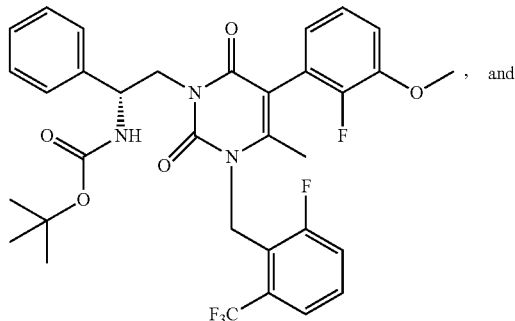
(xiii)
, and

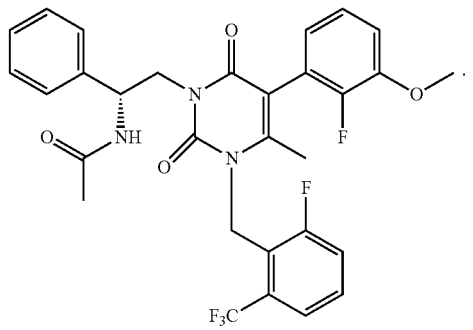
(xiv)

In some aspects the total percent peak area from the above impurities, which is the sum of the individual peak areas of each impurity above, is not more than about 7.5% peak area as determined by HPLC Method A. In other aspects, the total percent peak area from the above impurities is not more than about 6% peak area as determined by HPLC Method A. Individual impurity levels are determined by calculating the peak area (PA) percentage according to the following formula:

$$\text{Individual Impurity Peak Area \%} = 100 \times \frac{PA \text{ Impurity}}{PA \text{ Total}}$$

$PA_{Impurity}$=peak area of individual impurity in sample $PA_{Total}$=sum of all peak areas in the sample equal to or greater than 0.05 peak area %, excluding the salicylic acid peak In one embodiment, the composition comprising Compound (II) and an impurity, comprises not more than about 6% peak area of the impurity Compound (i) as determined by HPLC Method A. In another, the composition comprises not more than about 4% peak area as determined by HPLC Method A. In yet another, the composition comprises not more than about 2% peak area as determined by HPLC Method A.

In one embodiment, the composition comprising Compound (II) and an impurity, comprises not more than about 0.3% peak area of the Compound (xiii) as determined by HPLC Method A. In another, the composition comprises not more than about 0.2% peak area as determined by HPLC Method A. In yet another, the composition comprises not more than about 0.1% peak area as determined by HPLC Method A.

In one embodiment, the composition comprising Compound (II) and an impurity, comprises not more than about 0.6% peak area of the impurity Compound (xi) as determined by HPLC Method A. In another, the composition comprises not more than about 0.4% peak area as determined by HPLC Method A. In yet another, the composition comprises not more than about 0.2% peak area as determined by HPLC Method A.

In one embodiment, the composition comprising Compound (II) and an impurity, comprises not more than about 0.6% peak area of the impurity Compound (xii) as determined by HPLC Method A. In another, the composition comprises not more than about 0.4% peak area as determined by HPLC Method A. In yet another, the composition comprises not more than about 0.2% peak area as determined by HPLC Method A.

In one embodiment, the composition comprising Compound (II) and an impurity, comprises not more than about 0.6% peak area of the impurity Compound (xiv) as determined by HPLC Method A. In another, the composition comprises not more than about 0.4% peak area as determined by HPLC Method A. In yet another, the composition comprises not more than about 0.2% peak area as determined by HPLC Method A.

In one embodiment, a composition comprising Compound (II) and an impurity selected from the group consisting of Compounds (i, xi, xii, xiii, and xiv) is provided, wherein the sum of the % peak area of each of Compounds (i, xi, xii, xiii, and xiv) is not more than about 7.5% peak area as determined by HPLC Method A.

In one embodiment, a composition comprising Compound (II) and an impurity selected from the group consisting of Compounds (i, xi, xii, xiii, and xiv) is provided, wherein the sum of the % peak area of each of Compounds (i, xi, xii, xiii, and xiv) is not more than about 7.5% peak area as determined by HPLC Method A; and wherein the composition comprises not more than about 2.5 weight % of the impurity (2R)-2-[(tert-butoxycarbonyl)amino]-2-phenylethyl methanesulfonate as determined by LC-MS Method C.

In one embodiment, the composition comprising Compound (II) and an impurity, comprises not more than about 2.5 weight % of the impurity (2R)-2-[(tert-butoxycarbonyl)amino]-2-phenylethyl methanesulfonate as determined by LC-MS Method C. In another, the composition comprises not more than about 1.5 weight % as determined by LC-MS Method C. In yet another, the composition comprises not more than about 0.5 weight % as determined by LC-MS Method C.

In one embodiment, the process for preparing substantially pure elagolix sodium comprises using Compound (II) as an intermediate, reacting Compound (II) with a Compound of formula (III),

where $R^4$ is $C_1$-$C_8$ alkyl; and $X^2$ is Cl, Br, I, —OSO$_2$CH$_3$, —OSO$_2$C$_6$H$_4$CH$_3$ or —OSO$_2$CF$_3$; and forming a compound of formula (IV),

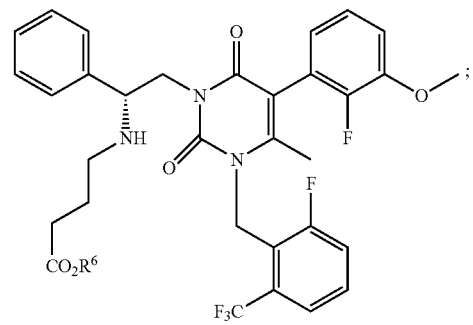

where $R^6$ is $C_1$-$C_8$ alkyl.

In another embodiment, the process for preparing substantially pure elagolix sodium comprises using Compound (II) as an intermediate, reacting Compound (II) with a Compound of formula (III), and treating a compound of formula (IV) with a sodium base to form elagolix sodium.

In other aspects, the process of preparing substantially pure elagolix sodium comprises using as an intermediate in the process, a compound of formula (VI),

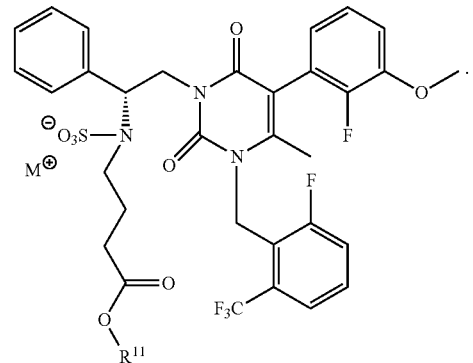

Compounds of formula (VI) are disclosed where
$R^{11}$ is selected from the group consisting of hydrogen, M', $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —OR$^a$, —NR$^a$R$^b$, —NR$^a$C(=O)R$^c$, —C(=O)R$^c$, —C(=O)OH, —C(=O)OR$^c$, —C(=O)NR$^a$R$^b$, —SO$_2$R$^c$, and —SO$_2$NR$^a$R$^b$;
R$^a$, and R$^b$ are each independently selected from the group consisting of hydrogen, $C_1$-$C_6$ alkyl, $C_6$-$C_{10}$ aryl, and 5-14 membered heteroaryl;
R$^c$ is selected from the group consisting of $C_1$-$C_6$ alkyl, $C_6$-$C_{10}$ aryl, and 5-14 membered heteroaryl;
J is $C_1$-$C_2$ alkylene;
M is selected from the group consisting of sodium, tetramethylguanidinium, 2,3,4,6,7,8,9,10-octahydropyrimido[1,2-a]azepinium, 3,4,6,7,8,9-hexahydro-2H-pyrido[1,2-a]pyrimidinium, and 2-hydroxyethan-1-aminium; and M' is selected from the group consisting of sodium, lithium, and potassium.

For compounds of formula (VI), other M groups are contemplated such as amine cations, including, but not limited to ammonium, alkylamminium, dialkylamminium, trialkyl amminium, iminium, guanidinium. Examples of alkylamminium include, for example, methaminium, ethaminium, propanaminium, 2-hydroxyethan-1-aminium, and the like. Examples of dialkylamminium include, for example, N-methylmethanaminium, N-methylethanaminium, N-ethylethanaminium, N-(propan-2-yl)propan-2-aminium, and the like. Examples of trialkylamminium include, for example, N,N-dimethylethanaminium, diethylethanaminium, N-ethyl-N-(propan-2-yl)propan-2-aminium, and the like. Examples of iminium include, for example, imidazolium and the like. Examples of guanidinium include, for example, tetramethylguanidium, 2,3,4,6,7,8,9,10-octahydropyrimido[1,2-a]azepinium, 3,4,6,7,8,9-hexahydro-2H-pyrido[1,2-a]pyrimidinium, and the like. It is understood that M is intended to be a cationic group capable of forming an ionic bond with the negatively charged anionic group in the compounds of formula (VI).

For compounds of formula (VI), other M' groups are contemplated including, but not limited to sodium, lithium, potassium, ammonium, and the like. When $R^{11}$ is M', it is understood that an ionic bond is intended between the cationic group M' and the carboxylate anion to which it is bonded.

In one embodiment, compounds of formula (VI), are provided where $R^{11}$ is selected from the group consisting of hydrogen, $C_1$-$C_6$ alkyl, $C_6$ aryl, and J-($C_6$ aryl); wherein the $C_6$ aryl, and J-($C_6$-$C_{10}$ aryl), may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —$OR^a$, —$NR^aR^b$, —$NR^aC(=O)R^c$, —$C(=O)R^c$, —$C(=O)OH$, —$C(=O)OR^c$, —$C(=O)NR^aR^b$, —$SO_2R^c$, and —$SO_2NR^aR^b$; and the remaining variables are as defined for formula (VI).

In one embodiment, compounds of formula (VI) are provided, where $R^{11}$ is $C_1$-$C_6$ alkyl; and the remaining variables are as defined for formula (VI).

In one embodiment, the compound of formula (VI) is the compound of formula (VIb), (VIb)

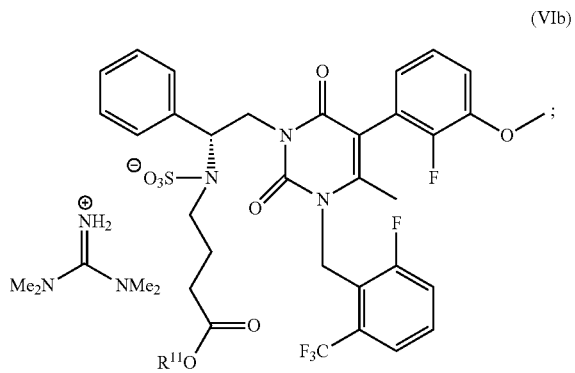

where $R^{11}$ is selected from the group consisting of hydrogen, M', $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —$OR^a$, —$NR^aR^b$, —$NR^aC(=O)R^c$, —$C(=O)R^c$, —$C(=O)OH$, —$C(=O)OR^c$, —$C(=O)NR^aR^b$, —$SO_2R^c$, and —$SO_2NR^aR^b$; and the remaining variables are as defined for formula (VI).

In one embodiment, the compound of formula (VI) is the compound of formula (VIb), where $R^{11}$ is $C_1$-$C_6$ alkyl.

In one embodiment, the compound of formula (VI) is the compound of formula (VIa), (VIa)

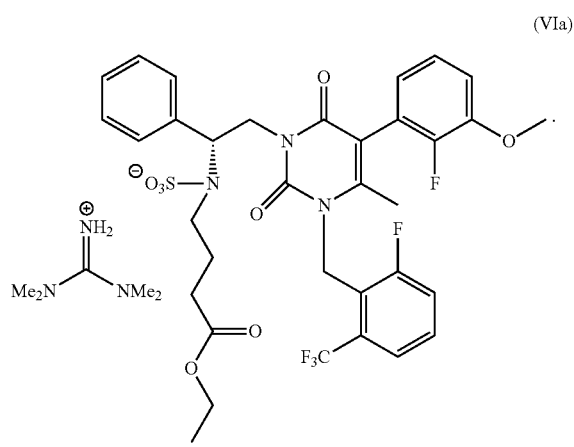

In other aspects, the process of preparing substantially pure elagolix sodium comprises using as an intermediate in the process, a compound of formula (VII).

Compounds of formula (VII) are disclosed where (VII)

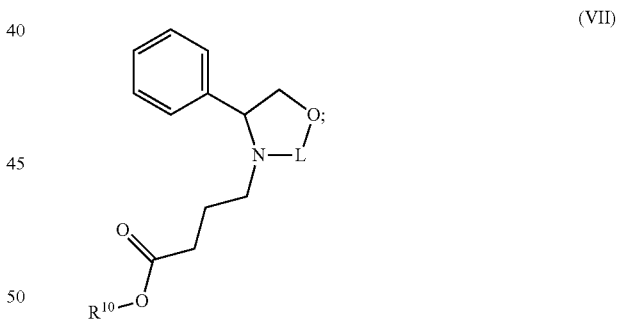

$R^{10}$ is selected from the group consisting of sodium, lithium, potassium, hydrogen, $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —$OR^a$, —$NR^aR^b$, —$NR^aC(=O)R^c$, —$C(=O)R^c$, —$C(=O)OH$, —$C(=O)OR^c$, —$C(=O)NR^aR^b$, —$SO_2R^c$, and —$SO_2NR^aR^b$;

$R^a$, and $R^b$ are each independently selected from the group consisting of hydrogen and $C_1$-$C_6$ alkyl, $C_6$-$C_{10}$ aryl, and 5-14 membered heteroaryl;

$R^c$ is selected from the group consisting of $C_1$-$C_6$ alkyl, $C_6$-$C_{10}$ aryl, and 5-14 membered heteroaryl;

J is $C_1$-$C_2$ alkylene;

L is selected from the group consisting of —SO—, —$SO_2$—, and —P(O)$OR^{12}$; and $R^{12}$ is selected from the group consisting of hydrogen and $C_1$-$C_6$ alkyl.

In one embodiment, compounds of formula (VII) are provided where L is —SO—, and the remaining variables are as defined for formula (VII). In other aspects, compounds of formula (VII) are provided where L is —$SO_2$—, and the remaining variables are as defined for formula (VII).

In one embodiment, compounds of formula (VII) are provided where $R^{10}$ is selected from the group consisting of hydrogen, $C_1$-$C_6$ alkyl, $C_6$ aryl, and J-($C_6$ aryl), and the remaining variables are as defined for formula (VII). In another embodiment, compounds of formula (VII) are provided where $R^{10}$ is selected from the group consisting of hydrogen, $C_1$-$C_6$ alkyl, $C_6$ aryl, and J-($C_6$ aryl), L is —SO—, and the remaining variables are as defined for formula (VII). In other embodiments, compounds of formula (VII) are provided where $R^{10}$ is selected from the group consisting of hydrogen, $C_1$-$C_6$ alkyl, $C_6$ aryl, and J-($C_6$ aryl), L is —$SO_2$—, and the remaining variables are as defined for formula (VII).

In one embodiment, compounds of formula (VII) are provided where $R^{10}$ is $C_1$-$C_6$ alkyl, and the remaining variables are as defined for formula (VII). In another embodiment, compounds of formula (VII) are provided where $R^{10}$ is $C_1$-$C_6$ alkyl, and L is —SO—. In another embodiment, compounds of formula (VII) are provided where $R^{10}$ is $C_1$-$C_6$ alkyl, and L is —$SO_2$—.

In one embodiment, compounds of formula (VII) are provided where $R^{10}$ is methyl, and the remaining variables are as defined for formula (VII). In another embodiment, compounds of formula (VII) are provided where $R^{10}$ is methyl, and L is —SO—. In another embodiment, compounds of formula (VII) are provided where $R^{10}$ is methyl, and L is —$SO_2$—.

In one embodiment, compounds of formula (VII) are provided where $R^{10}$ is ethyl, and the remaining variables are as defined for formula (VII). In another embodiment, compounds of formula (VII) are provided where $R^{10}$ is ethyl, and L is —SO—. In another embodiment, compounds of formula (VII) are provided where $R^{10}$ is ethyl, and L is —$SO_2$—.

In one embodiment, compounds of formula (VII) are provided where $R^{10}$ is propyl, and the remaining variables are as defined for formula (VII). In another embodiment, compounds of formula (VII) are provided where $R^{10}$ is propyl, and L is —SO—. In another embodiment, compounds of formula (VII) are provided where $R^{10}$ is propyl, and L is —$SO_2$—.

Compounds of formula (VIIa) are disclosed where

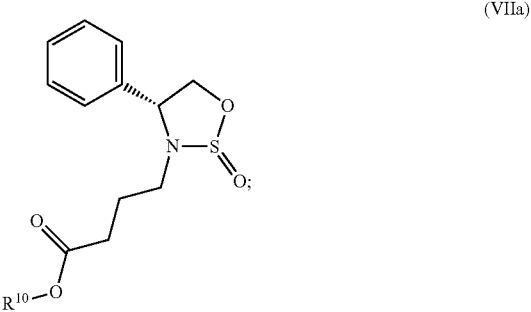

(VIIa)

$R^{10}$ is selected from the group consisting of sodium, lithium, potassium, hydrogen, $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —$OR^a$, —$NR^aR^b$, —$NR^aC(=O)R^c$, —$C(=O)R^c$, —C(=O)OH, —$C(=O)OR^c$, —$C(=O)NR^aR^b$, —$SO_2R^c$, and —$SO_2NR^aR^b$;

$R^a$, and $R^b$ are each independently selected from the group consisting of hydrogen and $C_1$-$C_6$ alkyl, $C_6$-$C_{10}$ aryl, and 5-14 membered heteroaryl;

$R^c$ is selected from the group consisting of $C_1$-$C_6$ alkyl, $C_6$-$C_{10}$ aryl, and 5-14 membered heteroaryl; and J is $C_1$-$C_2$ alkylene.

In some aspects of compounds of formula (VIIa), $R^{10}$ is selected from the group consisting of hydrogen, $C_1$-$C_6$ alkyl, $C_6$ aryl, and J-($C_6$ aryl). In other aspects $R^{10}$ is selected from the group consisting of $C_1$-$C_6$ alkyl, $C_6$ aryl, and J-($C_6$ aryl). In yet other aspects $R^{10}$ is $C_1$-$C_6$ alkyl. In some aspects, $R^{10}$ is methyl. In other aspects, $R^{10}$ is ethyl. In yet other aspects, $R^{10}$ is propyl.

Compounds of formula (VIIb) are disclosed where

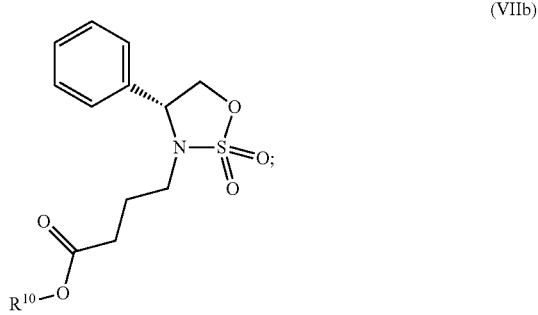

(VIIb)

$R^{10}$ is selected from the group consisting of sodium, lithium, potassium, hydrogen, $C_1$-$C_6$ alkyl, $C_2$-$C_4$ alkenyl, $C_6$-$C_{10}$ aryl, 5-14 membered heteroaryl, J-($C_6$-$C_{10}$ aryl), and J-(5-14 membered heteroaryl); wherein the $C_6$-$C_{10}$ aryl, 5-14 membered heteroaryl, J-($C_6$-$C_{10}$ aryl), and J-(5-14 membered heteroaryl) may be optionally substituted with 1 to 4 substituents independently selected from the group consisting of halogen, nitro, cyano, hydroxy, $C_1$-$C_6$ alkyl, $C_1$-$C_6$ haloalkyl, $C_3$-$C_{11}$ cycloalkyl, 3-14 membered heterocyclyl, —OR$^a$, —NR$^a$R$^b$, —NR$^a$C(=O)R$^c$, —C(=O)R$^c$, —C(=O)OH, —C(=O)OR$^c$, —C(=O)NR$^a$R$^b$, —SO$_2$R$^c$, and —SO$_2$NR$^a$R$^b$;

R$^a$, and R$^b$ are each independently selected from the group consisting of hydrogen and C$_1$-C$_6$ alkyl, C$_6$-C$_{10}$ aryl, and 5-14 membered heteroaryl;

R$^c$ is selected from the group consisting of C$_1$-C$_6$ alkyl, C$_6$-C$_{10}$ aryl, and 5-14 membered heteroaryl; and J is C$_1$-C$_2$ alkylene.

In some aspects of compounds of formula (VIIb), R$^{10}$ is selected from the group consisting of hydrogen, C$_1$-C$_6$ alkyl, C$_6$ aryl, and J-(C$_6$ aryl). In other aspects R$^{10}$ is selected from the group consisting of C$_1$-C$_6$ alkyl, C$_6$ aryl, and J-(C$_6$ aryl). In yet other aspects R$^{10}$ is C$_1$-C$_6$ alkyl. In some aspects, R$^{10}$ is methyl. In other aspects, R$^{10}$ is ethyl. In yet other aspects, R$^{10}$ is propyl.

In one embodiment, a process of preparing substantially pure elagolix sodium is provided comprising, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7,8,9,10-octahydropyrimido[1,2-a]azepinium, 3,4,6,7,8,9-hexahydro-2H-pyrido[1,2-a]pyrimidinium, and 2-hydroxyethan-1-aminium. In some aspects, R$^H$ is C$_1$-C$_6$ alkyl. In other aspects, R$^{11}$ is ethyl.

In one embodiment, the process of preparing substantially pure elagolix sodium comprises, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; and converting the compound of formula (VI) to Compound (I) by treatment with an acid and treatment with a first base. In some aspects, R$^H$ is C$_1$-C$_6$ alkyl. In other aspects, R$^{11}$ is ethyl.

In other embodiments, the process of preparing substantially pure elagolix sodium comprises, using as an intermediate in the process, a compound of formula (VI) where is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; and converting the compound of formula (VI) to Compound (I) at a temperature between about 10 to 35° C. by treatment with an acid, wherein the acid has a pH between about 0.1 and 4.0, and treatment with a first base, wherein the first base comprises a sodium cation. In some aspects, R$^{11}$ is C$_1$-C$_6$ alkyl. In other aspects, R$^{11}$ is ethyl.

In other embodiments, the process of preparing substantially pure elagolix sodium comprises, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; and converting the compound of formula (VI) to Compound (I) at a temperature between about 10 to 35° C. by treatment with an acid, wherein the acid has a pH between about 0.1 and 4.0, and treatment with a first base, wherein the first base comprises a sodium cation; wherein the acid is HCl; and wherein the first base is selected from the group consisting of sodium bicarbonate and sodium hydroxide. In some aspects, R$^{11}$ is C$_1$-C$_6$ alkyl. In other aspects, R$^{11}$ is ethyl.

In other embodiments, the process of preparing substantially pure elagolix sodium comprises, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; and converting the compound of formula (VI) to Compound (I) at a temperature between about 10 to 35° C. by treatment with an acid, wherein the acid has a pH between about 0.1 and 4.0, and treatment with a first base, wherein the first base comprises a sodium cation; treating Compound (VI) with an acid to form Compound (Ia), or a salt thereof; and treating Compound (Ia), or a salt thereof, with a sodium base to form Compound (I). In some aspects, R$^{11}$ is C$_1$-C$_6$ alkyl. In other aspects, R$^{11}$ is ethyl.

In other embodiments, the process of preparing substantially pure elagolix sodium comprises, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; reacting a compound of formula (VIIb) where R$^{10}$ is C$_1$-C$_6$ alkyl, C$_6$ aryl, and J-(C$_6$ aryl) and J is C$_1$-C$_2$ alkylene with compound (1-5) in the presence of a second base at a temperature between about 25 and 80° C. to form the Compound of formula (VI); and converting the compound of formula (VI) to Compound (I) at a temperature between about 10 to 35° C. by treatment with an acid, wherein the acid has a pH between about 0.1 and 4.0, and treatment with a first base, wherein the first base comprises a sodium cation. In some aspects, R$^{10}$ is C$_1$-C$_6$ alkyl; and R$^{11}$ is C$_1$-C$_6$ alkyl. In other aspects, R$^{10}$ is ethyl; and R$^{11}$ is ethyl.

In other embodiments, the process of preparing substantially pure elagolix sodium comprises, using as an intermediate in the process, a compound of formula (VI) where R$^{11}$ is selected from the group consisting of C$_1$-C$_6$ alkyl, C$_6$ aryl, and J-(C$_6$ aryl); J is C$_1$-C$_2$ alkylene; and M is selected from the group consisting of tetramethylguanidinium, 2,3,4,6,7, 8,9,10-octahydropyrimido[1,2-a]azepinium, 3,4,6,7,8,9-hexahydro-2H-pyrido[1,2-a]pyrimidinium, and 2-hydroxyethan-1-aminium; oxidizing a compound of formula (VIIa) at a temperature between about 15 and 36° C. to form a compound of formula (VIIb); reacting a compound of formula (VIIb) where R$^{10}$ is C$_1$-C$_6$ alkyl, C$_6$ aryl, and J-(C$_6$ aryl) and J is C$_1$-C$_2$ alkylene with compound (1-5) in the presence of a second base at a temperature between about 25 and 80° C. to form the Compound of formula (VI); and converting the compound of formula (VI) to Compound (I) at a temperature between about 10 to 35° C. by treatment with an acid, wherein the acid has a pH between about 0.1 and 4.0, and treatment with a first base, wherein the first base comprises a sodium cation. In some aspects, R$^{10}$ for each of formulae (VIIa) and (VIIb) is C$_1$-C$_6$ alkyl; and R$^{11}$ is C$_1$-C$_6$ alkyl. In other aspects, R$^{10}$ for each of formulae (VIIa) and (VIIb) is ethyl; and R$^{11}$ is ethyl.

In one embodiment, the process of preparing substantially pure elagolix sodium comprises, using as an intermediate in the process, a compound of formula (VIa); and converting the compound of formula (VIa) to Compound (I) by treatment with an acid and treatment with a first base.

In one embodiment, the process of preparing substantially pure elagolix sodium comprises, using as an intermediate in the process, a compound of formula (VIa); and converting the compound of formula (VIa) to Compound (I) at a temperature between about 10 to 35° C. by treatment with an acid, wherein the acid has a pH between about 0.1 and 4.0, and treatment with a first base, wherein the first base comprises a sodium cation.

In one embodiment, the process of preparing substantially pure elagolix sodium comprises, using as an intermediate in the process, a compound of formula (VIa); and converting the compound of formula (VIa) to Compound (I) at a temperature between about 10 to 35° C. by treatment with an acid, wherein the acid has a pH between about 0.1 and 4.0, and treatment with a first base, wherein the first base comprises a sodium cation; wherein the acid is HCl; and wherein the first base is selected from the group consisting of sodium bicarbonate and sodium hydroxide.

In one embodiment, the process of preparing substantially pure elagolix sodium comprises, using as an intermediate in the process, a compound of formula (VIa); and converting the compound of formula (VIa) to Compound (I) at a temperature between about 10 to 35° C. by treatment with an acid, wherein the acid has a pH between about 0.1 and 4.0, and treatment with a first base, wherein the first base comprises a sodium cation; treating Compound (VIa) with an acid to form Compound (Ia), or a salt thereof; and treating Compound (Ia), or a salt thereof, with a sodium base to form Compound (I).

In one embodiment, the process of preparing substantially pure elagolix sodium comprises, using as an intermediate in the process, a compound of formula (VIa); reacting a compound of formula (VIIb) where $R^{10}$ is ethyl with compound (1-5) in the presence of a second base at a temperature between about 25 and 80° C. to form the Compound of formula (VIa); and converting the compound of formula (VIa) to Compound (I) at a temperature between about 10 to 35° C. by treatment with an acid, wherein the acid has a pH between about 0.1 and 4.0, and treatment with a first base, wherein the first base comprises a sodium cation.

In one embodiment, the process of preparing substantially pure elagolix sodium comprises, using as an intermediate in the process, a compound of formula (VIa); oxidizing a compound of formula (VIIa) where $R^{10}$ is ethyl at a temperature between about 15 and 36° C. to form a compound of formula (VIIb) where $R^{10}$ is ethyl; reacting a compound of formula (VIIb) where $R^{10}$ is ethyl with compound (1-5) in the presence of a second base at a temperature between about 25 and 80° C. to form the Compound of formula (VIa); and converting the compound of formula (VIa) to Compound (I) at a temperature between about 10 to 35° C. by treatment with an acid, wherein the acid has a pH between about 0.1 and 4.0, and treatment with a first base, wherein the first base comprises a sodium cation.

In one embodiment, a composition comprising Compound (I) and one or more impurities y is provided, wherein the composition comprises at least about 97 weight percent Compound (I) and not more than about 3 weight percent of one or more impurities, wherein the composition is prepared by a process comprising using Compound (II) as an intermediate. In some aspects, the process further comprises reacting Compound (IIa) with salicylic acid to form Compound (II). In yet other aspects, the process further comprises reacting Compound (IIa) with salicylic acid to form Compound (II); and isolating Compound (II) to provide an isolated Compound (II). In some aspects the isolated Compound (II) is in solid form. In other aspects, the isolated Compound (II) is in crystalline form.

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (II) as an intermediate; and wherein the one or more impurities are selected from the group consisting of

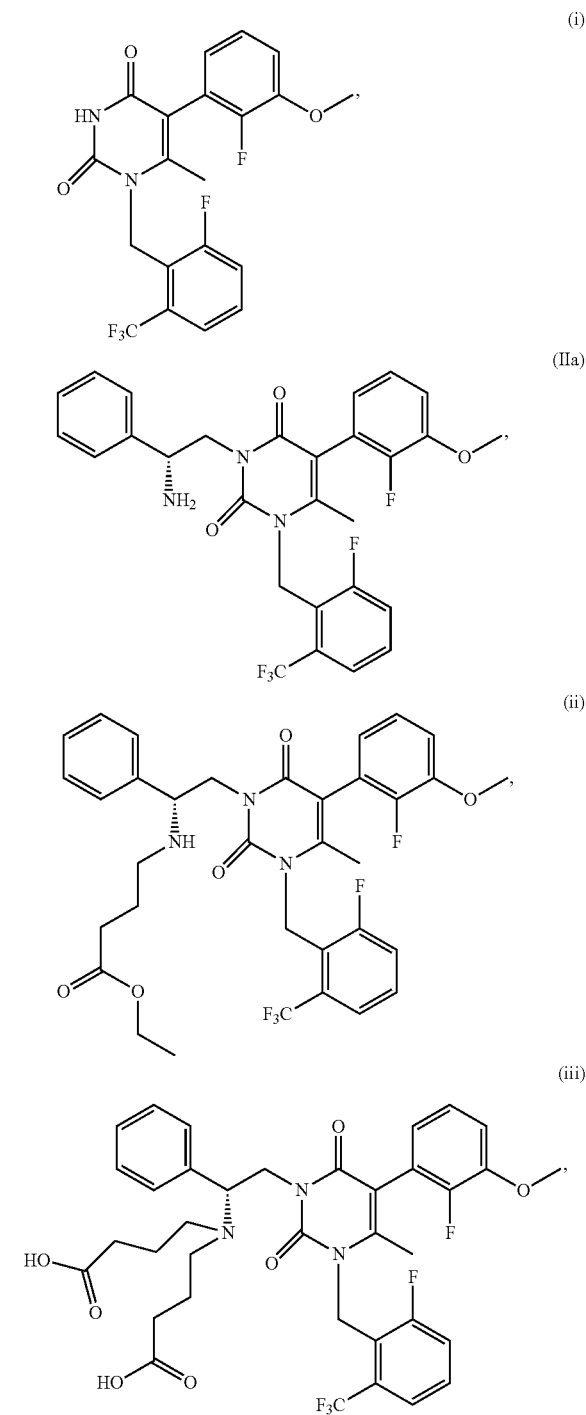

-continued

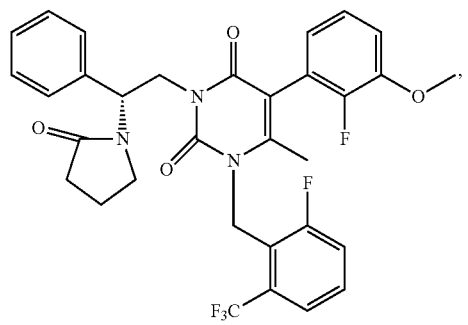
(iv)

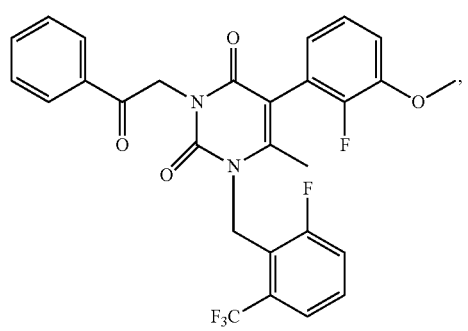
(v)

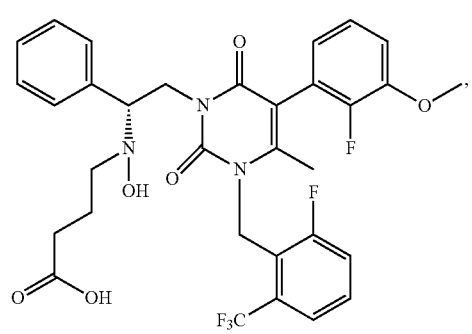
(vi)

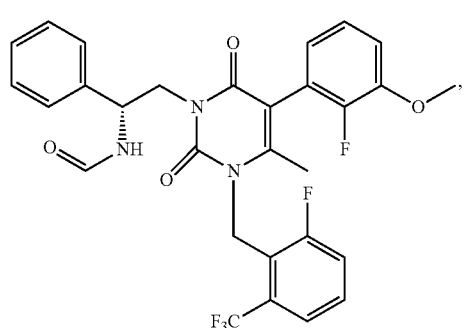
(vii)

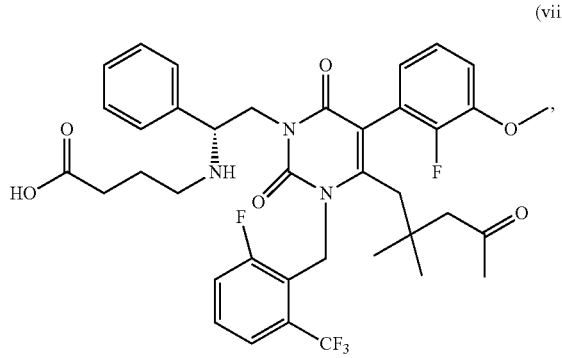
(viii)

-continued

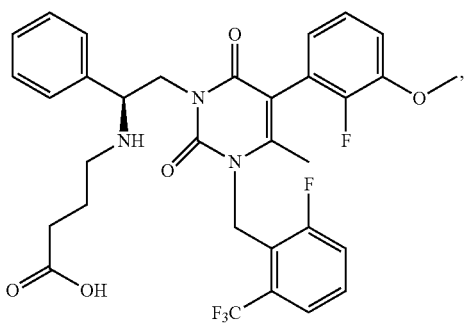
(ix)

(x)

(xv)

(xvi)

(xvii), and

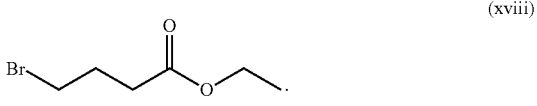
(xviii)

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (II) as an intermediate; and wherein the one or more impurities is a mutagenic impurity. The composition comprises no more than about 3 ppm of the mutagenic impurity. In some aspects, the composition comprises between about 0.0000001 and 3 ppm of the mutagenic impurity. The mutagenic impurity may be selected from the group consisting of

(xv)

(xvi)

(xvii), and (xviii)

Br~~~~O~ (ethyl 4-bromobutanoate structure)

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (II) as an intermediate; and wherein the one or more impurities is a mutagenic impurity, each of the mutagenic impurities is present in not more than about 3 ppm. In some aspects, composition comprises between about 0.0000001 and 3 ppm of the mutagenic impurity. In another embodiment, the sum of the mutagenic impurities is not more than about 10 ppm. In one aspect, the sum of the mutagenic impurities is between about 0.0000001 ppm and 10 ppm. The mutagenic impurities may be selected from the group consisting of Compounds (xv, xvi, xvii and xviii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (i). In some aspects, the composition comprises not more than about 0.15 weight percent of the one or more impurities which is Compound (i).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (IIa). In some aspects, the composition comprises not more than about 0.70 weight percent of the one or more impurities which is Compound (IIa).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (ii). In some aspects, the composition comprises not more than about 0.15 weight percent of the one or more impurities which is Compound (ii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (iii). In some aspects, the composition comprises not more than about 0.25 weight percent of the one or more impurities which is Compound (iii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (iv). In some aspects, the composition comprises not more than about 0.3 weight percent of the one or more impurities which is Compound (iv).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (v). In some aspects, the composition comprises not more than about 0.55 weight percent of the one or more impurities which is Compound (v).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (vi). In some aspects, the composition comprises not more than about 0.40 weight percent of the one or more impurities which is Compound (vi).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (vii). In some aspects, the composition comprises not more than about 0.35 weight percent of the one or more impurities which is Compound (vii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (viii). In some aspects, the composition comprises not more than about 0.15 weight percent of the one or more impurities which is Compound (viii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (ix). In some aspects, the composition comprises not more than about 0.2 weight percent of the one or more impurities which is Compound (ix).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (x). In some aspects, the composition comprises not more than about 25 ppm of the one or more impurities which is Compound (x).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (xv). In some aspects, the composition comprises not more than about 0.6 ppm of the one or more impurities which is Compound (xv).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (xvi). In some aspects, the composition comprises not more than about 0.9 ppm of the one or more impurities which is Compound (xvi).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (xvii). In some aspects, the composition comprises not more than about 2.5 ppm of the one or more impurities which is Compound (xvii).

In one embodiment, a composition comprising Compound (I) and one or more impurities is provided, wherein the composition comprises at least about 97 weight percent Compound (I) and not more than about 3 weight percent of one or more impurities; wherein the composition is prepared by a process comprising using Compound (II) as an intermediate; and wherein the one or more impurities is Compound (xviii). In some aspects, the composition comprises not more than about 2.5 ppm of the one or more impurities which is Compound (xviii).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VI) as an intermediate. In one aspect, the composition is prepared by a process comprising using Compound (VI) where M is guanidinium, as an intermediate. In another aspect the composition is prepared by a process comprising using Compound (VI) where M is guanidinium and $R^{11}$ is $C_1$-$C_6$ alkyl, as an intermediate.

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate. In some aspects the process further comprises isolating Compound (VIa) to provide an isolated Compound (VIa).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities are selected from the group consisting of Compounds (i, Ia, ii, iv, v, vi, vii, viii, ix, x, and xviii).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (i). In some aspects, the composition comprises not more than about 0.15 weight percent of the one or more impurities which is Compound (i).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (IIa). In some aspects, the composition comprises not more than about 0.70 weight percent of the one or more impurities which is Compound (IIa).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (ii). In some aspects, the composition comprises not more than about 0.15 weight percent of the one or more impurities Compound (ii).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is compound (iv). In some aspects, composition comprises not more than about 0.3 weight percent of the impurity Compound (iv). In some aspects, the composition comprises not more than about 0.3 weight percent of the impurity which is Compound (iv).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (v). In some aspects, the composition comprises not more than about 0.55 weight percent of the one or more impurities which is Compound (v).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (vi). In some aspects, the composition comprises not more than about 0.40 weight percent of the one or more impurities which is Compound (vi).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (vii). In some aspects, the composition comprises not more than about 0.35 weight percent of the one or more impurities which is Compound (vii).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (viii). In some aspects, the composition comprises not more than about 0.15 weight percent of the one or more impurities which is Compound (viii).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (ix). In some aspects, the composition comprises not more than about 0.2 weight percent of the one or more impurities which is Compound (ix).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (x). In some aspects, the composition comprises not more than about 25 ppm of the one or more impurities which is Compound (x).

In one embodiment, a composition comprising Compound (I) and one or more impurities is provided, wherein the composition comprises at least about 97 weight percent Compound (I) and not more than about 3 weight percent of one or more impurities, wherein the composition is prepared by a process comprising using Compound (VIa) as an intermediate, wherein the one or more impurities is Compound (xviii). In some aspects, the composition comprises not more than about 2.5 ppm of the one or more impurities which is Compound (xviii).

Since elagolix sodium, Compound (I), does not have any known polymorphic forms, it is isolated in the amorphous form by a process of precipitation by mixing a solution of Compound (I) in a solvent such as methyl isobutyl ketone, water, alcohols, esters, or ketones with an anti-solvent such as heptanes, hexanes, or other alkanes. The mode of mixing may include addition of the solution of Compound (I) into an anti-solvent, or vice-versa, or by simultaneous mixing of the respective streams in a continuous manner. Once precipitated, Compound (I), which has a significant affinity to the solvents, may be isolated by filtration, washing and drying to remove residual solvents and thereby afford elagolix sodium with a very low impurity profile. The isolation may be conducted in a variety of equipment such as an agitated filter dryer, spray dryer, or other commonly used commercial equipment for solid isolation. The combination of the precipitation and isolation processes offer the unique ability to broadly manipulate physical properties of the isolated elagolix sodium, including, for example, particle size distribution, specific surface area, porosity, bulk density and the extent of agglomeration. The combination of these processes allows targeting of the physical properties as characterized by the above attributes to enable the selection and use of a variety of formulations and formulation process options.

Through the processes of precipitation and isolation, the Compound (I) solids form agglomerates and aggregates comprising very small primary particles with diameters in the tens to hundreds of nanometers. The microstructure or porosity of the agglomerates and aggregates is dependent on the size of the primary particles and the extent of interconnections between primary particle sub units. The unique microstructure of amorphous elagolix sodium offers a product powder which consists of highly porous particles with high specific surface area. The ability to enhance product porosity and specific surface area by the processes of precipitation and isolation enables the product to act as binder in a solid dosage formulation such as, for example, in a conventional tablet form. The amorphous form of Compound (I) has a dry glass transition temperature (Tg) of about 108° C. Since solvents such as methyl isobutyl ketone, water, alcohols, esters, ketones are plasticizers of the amorphous solids, the glass transition temperature is reduced in their presence. Under conditions where the glass transition temperature is reduced, the sub-micron particles of Compound (I) can fuse together, which is hereinafter referred to as sintering. Sintering results in larger primary particle sub units and reduction of the overall porosity and specific surface area. Sintering may be induced by increasing temperature beyond the Tg, higher solvent content, and may be accelerated by extending the product-solvent contact time and mixing intensity. Specific surface area of Compound (I) in the range of 0.3 to 49.0 $m^2/g$ has been obtained, as shown in Examples 14-18.

In one embodiment, a composition of Compound (I) is provided comprising Compound (I) and one or more impurities; wherein the composition comprises at least about 97 weight percent of Compound (I) and not more than about 3 weight percent of the one or more impurities; and wherein the composition has a specific surface area between about 0.3 and about 49.0 $m^2/g$.

In another embodiment, a composition of Compound (I) is provided comprising Compound (I) and one or more impurities; wherein the composition comprises at least about 97 weight percent of Compound (I) and not more than about 3 weight percent of the one or more impurities; wherein the composition is prepared by a process comprising, using as an intermediate, Compound (II); and wherein the composition has a specific surface area between about 0.3 and about 49.0 $m^2/g$.

Since the amorphous form of Compound (I) is extremely cohesive, it is prone to formation of agglomerates and aggregates through process of mixing in a vessel via shear, compaction, consolidation and acoustic energy. Thus, the extent of agglomeration and aggregation can dictate the flowability, bulk density, and particle size distribution. In the process of product isolation from a mixture of product, solvent, and anti-solvent, the product cake may experience shear, compaction and consolidation upon mixing. The extent of shear imparted on the product will also be determined by the intensity and duration of any mixing event during processing and the solvent content in the product cake, thus enabling the modulation of the flowability, bulk density and particle-size distribution. Flow function coefficient ($ff_c = \sigma / f_c$) of the product ranging from 1.2 to 6.8, bulk density ranging from 0.15 g/mL to 0.45 g/mL, and volume-averaged particle size Dv10 ranging from 6 to 204 μm have been obtained by modulating the extent of agglomeration and aggregation, as shown in Examples 14-18. Control of the physical properties of Compound (I) including bulk density, flow function coefficient, volume-averaged particle size, and specific surface area has been obtained without the use of acoustic mixing. The process of modulating the flowability, bulk density and particle size distribution of elagolix sodium using acoustic mixing has been described in U.S. Pat. No. 9,949,973, which is incorporated herein by reference.

In one embodiment, a composition of Compound (I) is provided comprising Compound (I) and one or more impurities, wherein the composition comprises at least about 97 weight percent of Compound (I) and not more than about 3 weight percent of the one or more impurities; and wherein the composition has a flow function coefficient between about 1.2 and about 6.8.

In one embodiment, a composition of Compound (I) is provided comprising Compound (I) and one or more impurities, wherein the composition comprises at least about 97 weight percent of Compound (I) and not more than about 3 weight percent of the one or more impurities; and wherein the composition has a bulk density between about 0.15 g/mL and about 0.45 g/mL.

In one embodiment, a composition of Compound (I) is provided comprising Compound (I) and one or more impurities, wherein the composition comprises at least about 97 weight percent of Compound (I) and not more than about 3 weight percent of the one or more impurities; and wherein the composition has a volume-averaged particle size Dv10 between about 6 and about 204 μm.

In another embodiment, a composition of Compound (I) is provided comprising Compound (I) and one or more impurities; wherein the composition comprises at least about 97 weight percent of Compound (I) and not more than about 3 weight percent of the one or more impurities; wherein the composition is prepared by a process comprising, using as an intermediate, Compound (II); and wherein the composition has a flow function coefficient between about 1.2 and about 6.8.

In another embodiment, a composition of Compound (I) is provided comprising Compound (I) and one or more impurities; wherein the composition comprises at least about 97 weight percent of Compound (I) and not more than about 3 weight percent of the one or more impurities; wherein the composition is prepared by a process comprising, using as an intermediate, Compound (II); and wherein the composition has a bulk density between about 0.15 g/mL and about 0.45 g/mL.

In another embodiment, a composition of Compound (I) is provided comprising Compound (I) and one or more impurities; wherein the composition comprises at least about 97 weight percent of Compound (I) and not more than about 3 weight percent of the one or more impurities; wherein the composition is prepared by a process comprising, using as an intermediate, Compound (II); and wherein the composition has a volume-averaged particle size Dv10 between about 6 and about 204 μm.

Solid State of Compound II and IIa

Use of Compound (II), including its polymorphic forms, affords a significant advancement in the manufacturability of elagolix sodium.

The salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione (Compound II) may be prepared by combining 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione with salicylic acid to form a salt as described herein.

In one embodiment, a polymorphic form of Compound (II) is provided. In some aspects the polymorphic form is crystalline. Crystalline forms of Compound (II) provided herein are the desolvated/dehydrated polymorph, the methanol solvated polymorph, the methanol/water solvated polymorph, and the ethyl acetate solvated polymorph.

In one embodiment, the polymorphic form of Compound (II) is a crystalline solid substantially free of amorphous Compound (II).

The polymorphic forms of Compound (II) comprise a molar ratio of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione to salicylic acid of about 1.1:1 to about 1:1.1. In other aspects the ratio is about 1.05:1 to about 1:1.05. In yet other aspects the ratio is about 1:1.

In one embodiment, the polymorphic form of Compound (II) is a solvated crystalline form.

Compound (II) Desolvated/Dehydrated Polymorph

In one embodiment, the crystalline form of Compound (II) is a desolvated/dehydrated crystalline form. The crystalline form may be formed by desolvation of a solvated form. In one aspect, the desolvated/dehydrated crystalline form is formed by desolvation of the methanol/water solvated polymorph form.

Figure 4:
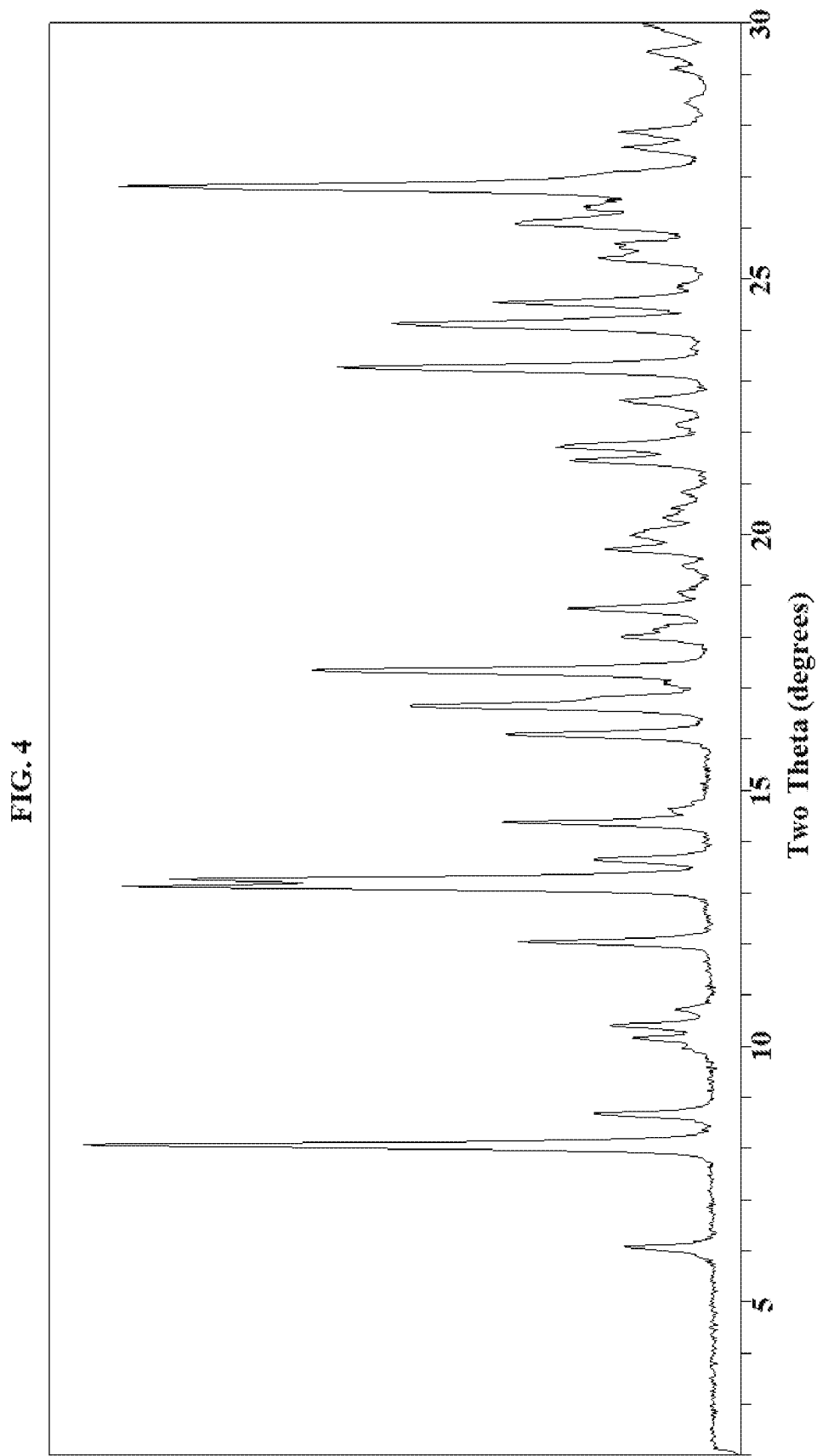
FIG. 4 is a powder X-ray diffraction pattern corresponding to Form D.

In one embodiment, the crystalline form of Compound (II) has an X-ray powder diffraction pattern substantially as shown in FIG. 4.

In one embodiment, the desolvated/dehydrated crystalline form of Compound (II) has an X-ray powder diffraction pattern comprising one or more peaks at about 6.1, 8.1, 8.7, 10.2, 10.4, 12.0, 13.1, 14.4, 16.6, and 17.4° 2θ, when measured at about 25° C. with Cu—$K_{\alpha1}$ radiation (1.5406 Å) with Cu fine focus X-ray tube energized at 40 kV and 30 mA. In one aspect, the desolvated/dehydrate crystalline form of Compound (II) has an X-ray powder diffraction pattern comprising one or more peaks at ±0.2 of 6.1, 8.1, 8.7, 10.2, 10.4, 12.0, 13.1, 14.4, 16.6, and 17.4° 2θ, when measured at about 25° C. with Cu—$K_{\alpha1}$ radiation (1.5406 Å) with Cu fine focus X-ray tube energized at 40 kV and 30 mA. In another aspect, the desolvated/dehydrate crystalline form of Compound (II) has an X-ray powder diffraction pattern comprising one or more peaks at ±0.1 of 6.1, 8.1, 8.7, 10.2, 10.4, 12.0, 13.1, 14.4, 16.6, and 17.4° 2θ, when measured at about 25° C. with Cu—$K_{\alpha1}$ radiation (1.5406 Å) with Cu fine focus X-ray tube energized at 40 kV and 30 mA.

In one embodiment, the desolvated/dehydrate crystalline form of Compound (II) has an X-ray powder diffraction pattern comprising peaks at ±0.2 of 10.2, 10.4, and 12.0° 2θ, when measured at about 25° C. with Cu—$K_{\alpha1}$ radiation (1.5406 Å) with Cu fine focus X-ray tube energized at 40 kV and 30 mA. In another embodiment, the desolvated/dehydrate crystalline form of Compound (II) has an X-ray powder diffraction pattern comprising peaks at ±0.2 of 6.1, 8.1, 10.2, 10.4, and 12.0° 2θ, when measured at about 25° C. with Cu—$K_{\alpha1}$ radiation (1.5406 Å) with Cu fine focus X-ray tube energized at 40 kV and 30 mA.

Compound (II) Methanol Solvated Polymorph

The solvated crystalline form of Compound (II) may be solvated with methanol. The methanol may be present in the solvated crystalline form of Compound (II) in an amount from about 0.1 to 5.0 weight percent. In other aspects, the methanol is present in an amount from about 0.1 to 4.5 weight percent.

In one embodiment, the methanol solvated crystalline form of Compound (II), the molar ratio of methanol to 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione is between about 0.1:1 and 1:1.1. In other aspects the ratio is about 0.45:1 to about 1:1.1. In yet other aspects the ratio is about 1:1.

Figure 3:
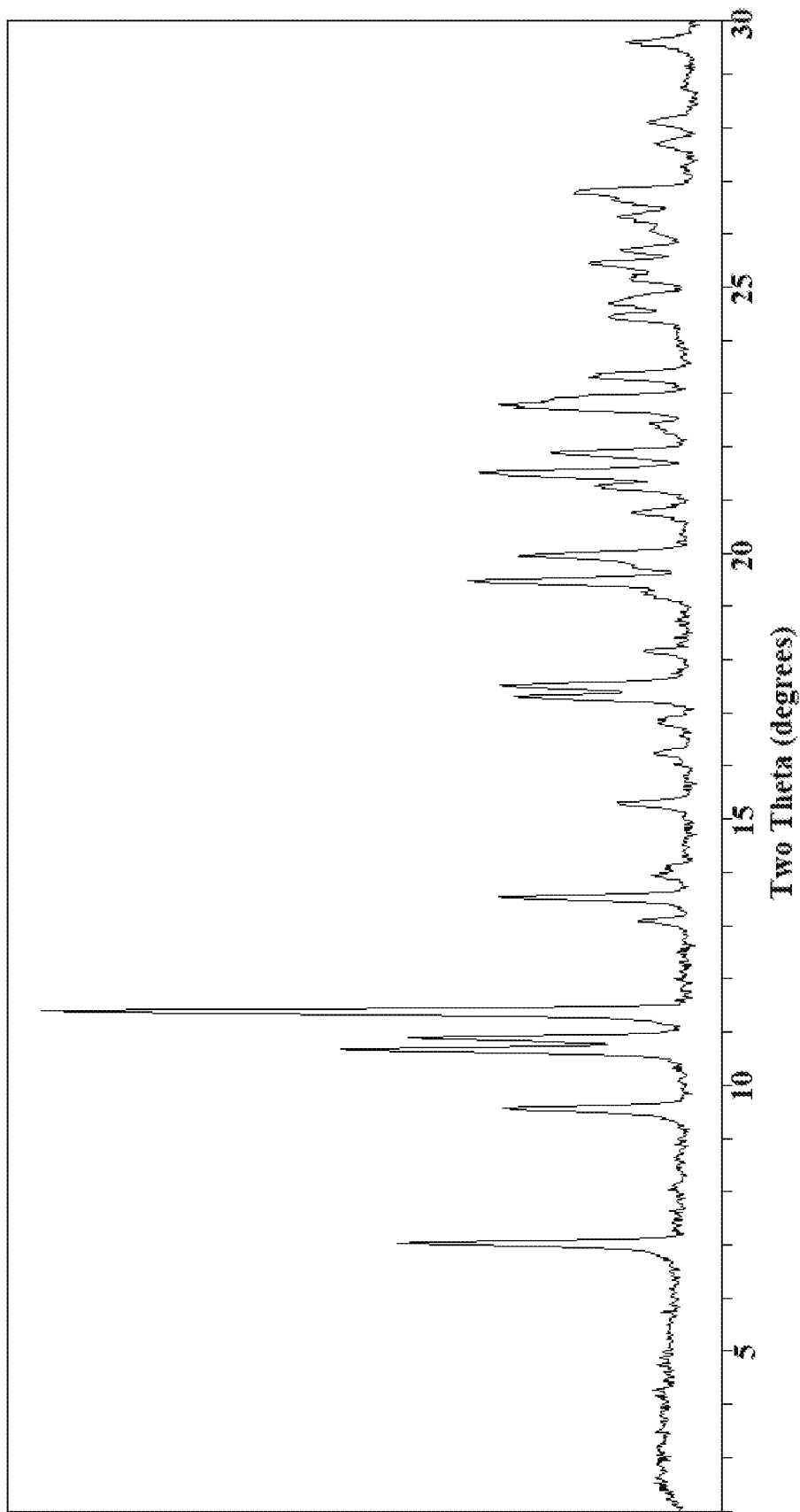
FIG. 3 is a powder X-ray diffraction pattern corresponding to Form C.

In one embodiment, the methanol solvated crystalline form of Compound (II) has an X-ray powder diffraction pattern substantially as shown in FIG. 3.

In one embodiment, the methanol solvated crystalline form of Compound (II) has an X-ray powder diffraction pattern comprising one or more peaks at ±0.2 of 7.0, 9.6, 10.7, 10.9, 11.4, 13.1, 13.5, 17.3, 17.5, and 18.2° 2θ, when measured at about 25° C. with Cu—K$_{\alpha 1}$ radiation (1.5406 Å) with Cu fine focus X-ray tube energized at 40 kV and 30 mA. In another aspect, the methanol solvated crystalline form of Compound (II) has an X-ray powder diffraction pattern comprising one or more peaks at ±0.1 of 7.0, 9.6, 10.7, 10.9, 11.4, 13.1, 13.5, 17.3, 17.5, and 18.2° 2θ, when measured at about 25° C. with Cu—K$_{\alpha 1}$ radiation (1.5406 Å) with Cu fine focus X-ray tube energized at 40 kV and 30 mA. In yet another aspect, the methanol solvated crystalline form of Compound (II) has an X-ray powder diffraction pattern comprising one or more peaks at about 7.0, 9.6, 10.7, 10.9, 11.4, 13.1, 13.5, 17.3, 17.5, and 18.2° 2θ, when measured at about 25° C. with Cu—K$_{\alpha 1}$ radiation (1.5406 Å) with Cu fine focus X-ray tube energized at 40 kV and 30 mA.

In one embodiment, the methanol solvated crystalline form of Compound (II) has an X-ray powder diffraction pattern comprising peaks at ±0.2 of 7.0, 9.6, and 11.4° 2θ, when measured at about 25° C. with Cu—K$_{\alpha 1}$ radiation (1.5406 Å) with Cu fine focus X-ray tube energized at 40 kV and 30 mA. In one embodiment, the methanol solvated crystalline form of Compound (II) has an X-ray powder diffraction pattern comprising peaks at ±0.2 of 7.0, 9.6, 10.7, 10.9, and 11.4° 2θ, when measured at about 25° C. with Cu—K$_{\alpha 1}$ radiation (1.5406 Å) with Cu fine focus X-ray tube energized at 40 kV and 30 mA.

Compound (II) Methanol/Water Solvated Polymorph

The solvated crystalline form of Compound (II) may be solvated with more than one solvent. The solvated crystalline form of Compound (II) may be solvated with methanol and water. The methanol may be present in the solvated crystalline form of Compound (II) in an amount from about 0.1 to 5.0 weight percent and the water may be present in an amount from about 1.0 to 5.0 weight percent. In other aspects, the methanol is present in an amount from about 0.1 to 5.0 weight percent and the water is present in an amount from about 1.1 to 1.4 weight percent. In yet other aspects, the methanol is present in an amount from about 0.1 to 2.0 weight percent and the water is present in an amount from about 1.3 to 5.0 weight percent.

In one embodiment, the solvated crystalline form of Compound (II) is solvated with methanol and water. The methanol may be present in the solvated crystalline form of Compound (II) in an amount from about 4.2 to 4.8 weight percent and the water is present in an amount from about 1.0 to 1.6 weight percent. In other aspects, the methanol is present in an amount from about 4.3 to 4.7 weight percent and the water is present in an amount from about 1.2 to 1.4 weight percent. In yet other aspects, the methanol is present in an amount from about 4.4 to 4.6 weight percent and the water is present in an amount from about 1.25 to 1.35 weight percent. In other aspects, the methanol is present in an amount about 4.5 weight percent and the water is present in an amount of about 1.3 weight percent.

In one embodiment, the molar ratio of water to 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione is between about 0.3:1 and 0.6:1. In other aspects, the molar ratio of water to 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione is between about 0.45:1 and 0.55:1.

In one embodiment, the solvated crystalline form of Compound (II) is solvated with methanol and water, and the ratio of methanol to water is from 1.1:0.4 to 0.9:0.6. In other aspects, the ratio of methanol to water is about 1:0.5.

As the solvated crystalline form of Compound (II) which is solvated with methanol and water is dried, methanol can escape via channels in the crystalline form, thereby reducing he methanol content in the crystalline form. In some aspects, the methanol is replaced by water, thereby increasing the water content in the crystalline form. For example, the solvated crystalline form of Compound (II) which is solvated with methanol and water may comprise between about 0.1 to 5.0 weight percent methanol and between about 1.0 to 5.0 weight percent water.

When the crystalline form comprises about 1.0 equivalents of methanol and 0.5 equivalents of water, the crystalline form of Compound (II) comprises between about 4.3 and 4.5 weight percent methanol and 1.1 to 1.3 weight percent water. When the crystalline form comprises about 0.5 equivalents of methanol and 0.5 equivalents of water, the crystalline form of Compound (II) comprises between about 2.3 and 2.1 weight percent methanol and 1.2 to 1.4 weight percent water. When the crystalline form comprises about 0.5 equivalents of methanol and 0.75 equivalents of water, the crystalline form of Compound (II) comprises between about 1.0 and 1.2 weight percent methanol and 1.8 to 2.0 weight percent water. When the crystalline form comprises trace amounts of methanol and 2.0 equivalents of water, the crystalline form of Compound (II) comprises greater than zero and less than 0.1 weight percent methanol and between about 4.9 and 5.1 weight percent water.

Figure 2:
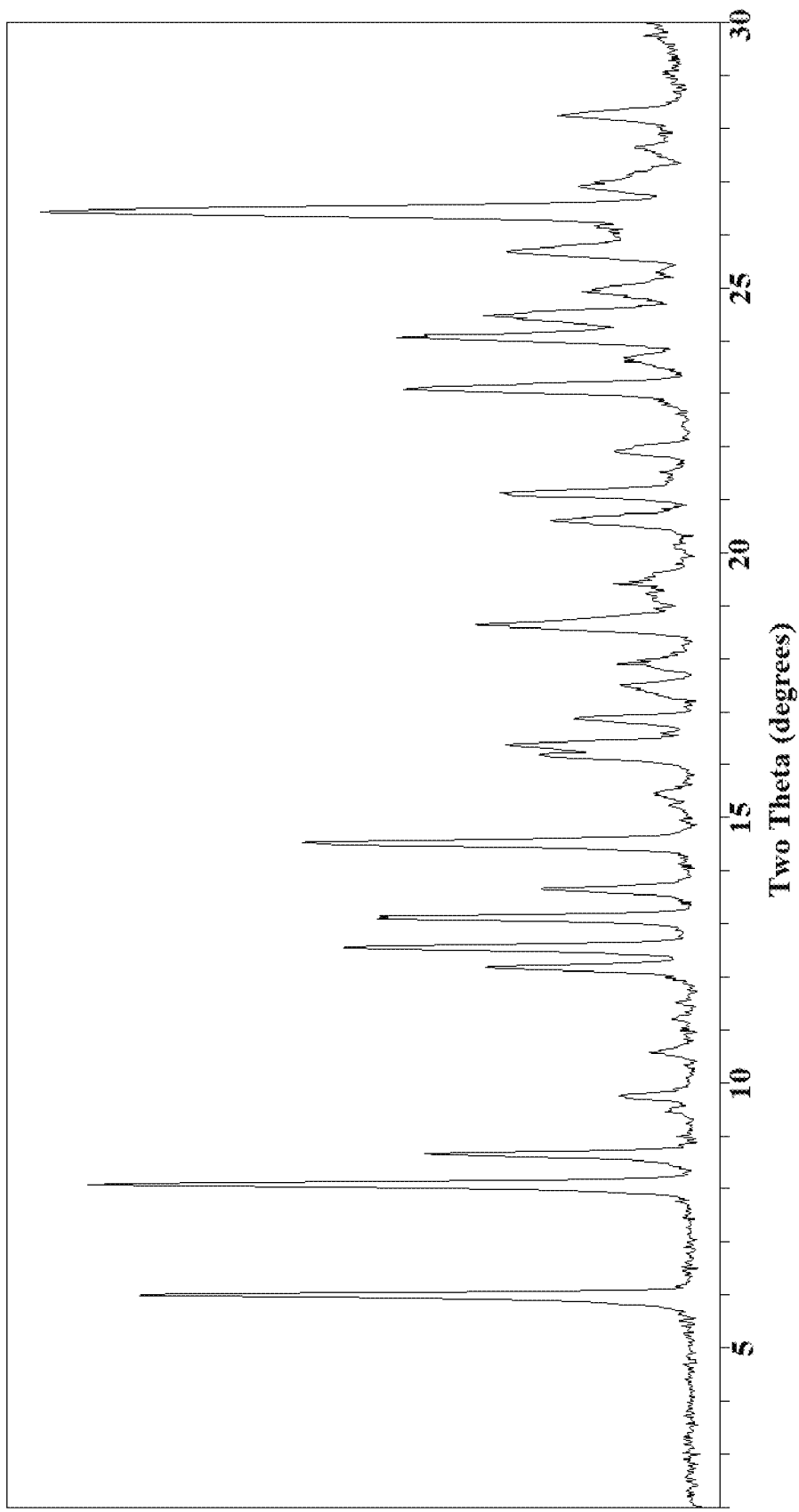
FIG. 2 is a powder X-ray diffraction pattern corresponding to Form B.

In one embodiment, the methanol and water solvated crystalline form of Compound (II) has an X-ray powder diffraction pattern substantially as shown in FIG. 2.

In one embodiment, the methanol and water solvated crystalline form of Compound (II) has an X-ray powder diffraction pattern comprising one or more peaks at about 6.0, 8.1, 8.7, 9.5, 9.8, 10.6, 12.2, 12.5, 13.1, and 14.5° 2θ, when measured at about 25° C. with Cu—K$_{\alpha 1}$ radiation (1.5406 Å) with Cu fine focus X-ray tube energized at 40 kV and 30 mA. In one aspect, the methanol and water solvated crystalline form of Compound (II) has an X-ray powder diffraction pattern comprising one or more peaks at ±0.2 of 6.0, 8.1, 8.7, 9.5, 9.8, 10.6, 12.2, 12.5, 13.1, and 14.5° 2θ, when measured at about 25° C. with Cu—K$_{\alpha 1}$ radiation (1.5406 Å) with Cu fine focus X-ray tube energized at 40 kV and 30 mA. In another aspect, the methanol and water solvated crystalline form of Compound (II) has an X-ray powder diffraction pattern comprising one or more peaks at ±0.1 of 6.0, 8.1, 8.7, 9.5, 9.8, 10.6, 12.2, 12.5, 13.1, and 14.5° 2θ, when measured at about 25° C. with Cu—K$_{\alpha 1}$ radiation (1.5406 Å) with Cu fine focus X-ray tube energized at 40 kV and 30 mA.

In one embodiment, the methanol and water solvated crystalline form of Compound (II) has an X-ray powder diffraction pattern comprising peaks at ±0.2 of 6.0, 9.8, and 12.5° 2θ, when measured at about 25° C. with Cu—K$_{\alpha 1}$ radiation (1.5406 Å) with Cu fine focus X-ray tube energized at 40 kV and 30 mA. In another embodiment, the methanol and water solvated crystalline form of Compound (II) has an X-ray powder diffraction pattern comprising peaks at ±0.2 of 6.0, 8.1, 9.8, 12.5, and 14.5° 2θ, when measured at about 25° C. with Cu—K$_{\alpha 1}$ radiation (1.5406 Å) with Cu fine focus X-ray tube energized at 40 kV and 30 mA.

Compound (II) Ethyl Acetate Solvated Polymorph

In one embodiment, a polymorphic form of Compound (II) is provided, wherein the polymorphic form is crystalline, and wherein the crystalline form is solvated with ethyl acetate.

Figure 5:
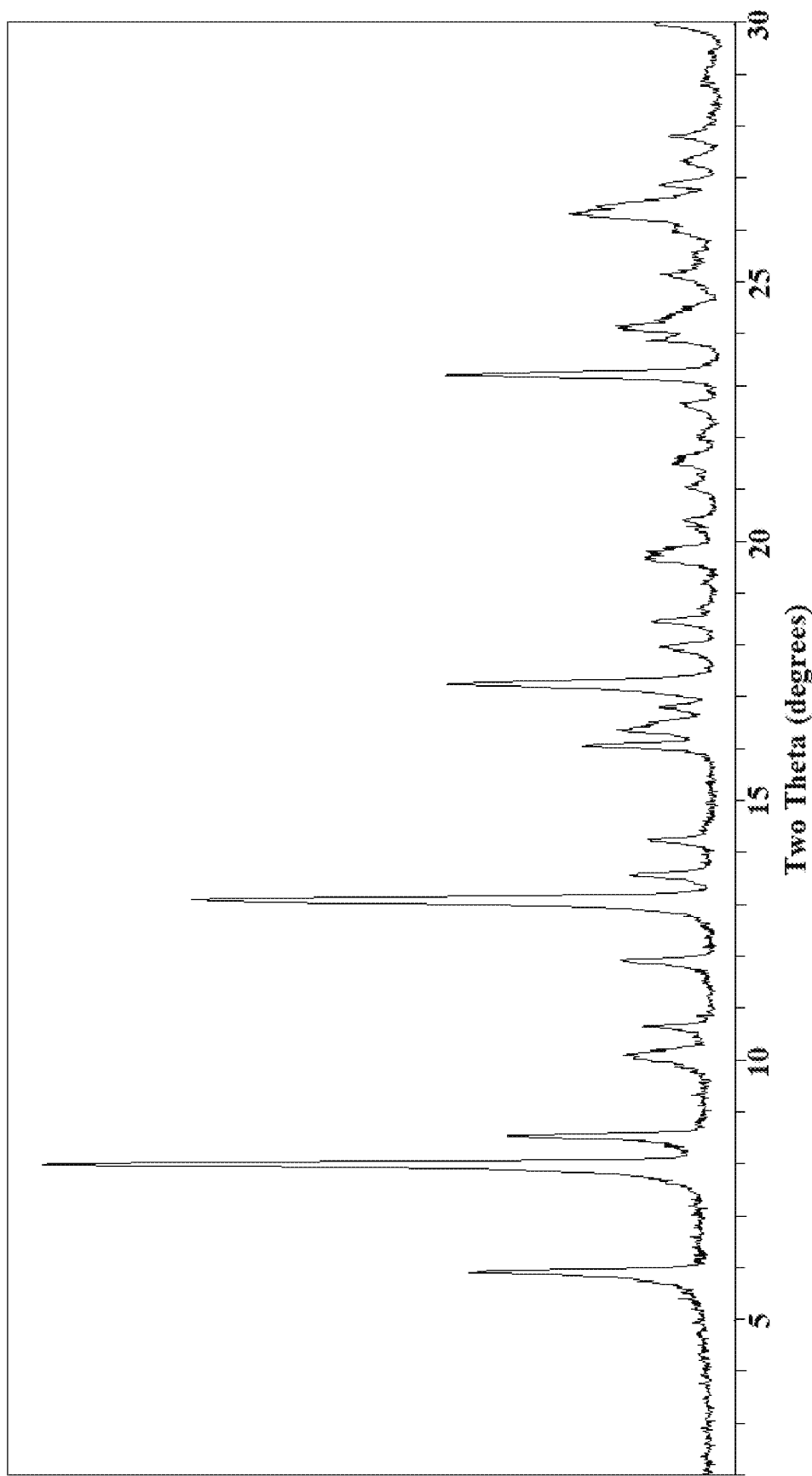
FIG. 5 is a powder X-ray diffraction pattern corresponding to Form E.

In one embodiment, the ethyl acetate solvated crystalline form of Compound (II) has an X-ray powder diffraction pattern substantially as shown in FIG. 5.

In one embodiment, the ethyl acetate solvated crystalline form of Compound (II) has an X-ray powder diffraction pattern comprising on or more peaks at about 5.9, 8.0, 8.5, 10.1, 10.6, 11.9, 13.1, 13.6, 16.0 and 17.2° 2θ, when measured at about 25° C. with Cu—K$_{\alpha 1}$ radiation (1.5406 Å) with Cu fine focus X-ray tube energized at 40 kV and 30 mA. In one aspect, the ethyl acetate solvated crystalline form of Compound (II) has an X-ray powder diffraction pattern comprising one or more peaks at ±0.2 of 5.9, 8.0, 8.5, 10.1, 10.6, 11.9, 13.1, 13.6, 16.0 and 17.2° 2θ, when measured at about 25° C. with Cu—K$_{\alpha 1}$ radiation (1.5406 Å) with Cu fine focus X-ray tube energized at 40 kV and 30 mA. In another aspect, the ethyl acetate solvated crystalline form of Compound (II) has an X-ray powder diffraction pattern comprising one or more peaks at ±0.1 of 5.9, 8.0, 8.5, 10.1, 10.6, 11.9, 13.1, 13.6, 16.0 and 17.2° 2θ, when measured at about 25° C. with Cu—K$_{\alpha 1}$ radiation (1.5406 Å) with Cu fine focus X-ray tube energized at 40 kV and 30 mA.

In one embodiment, the ethyl acetate solvated crystalline form of Compound (II) has an X-ray powder diffraction pattern comprising peaks at ±0.2 of 8.0, 8.5, and 13.1° 2θ, when measured at about 25° C. with Cu—K$_{\alpha 1}$ radiation (1.5406 Å) with Cu fine focus X-ray tube energized at 40 kV and 30 mA. In one embodiment, the ethyl acetate solvated crystalline form of Compound (II) has an X-ray powder diffraction pattern comprising peaks at ±0.2 of 5.9, 8.0, 8.5, 13.1, and 17.2° 2θ, when measured at about 25° C. with Cu—K$_{\alpha 1}$ radiation (1.5406 Å) with Cu fine focus X-ray tube energized at 40 kV and 30 mA.

Compound (IIa) Anhydrate

In one embodiment, a crystalline form of a 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione, Compound (IIa), is provided. The crystalline form is substantially free of amorphous 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione.

In one embodiment, the crystalline form of Compound (IIa) is an anhydrate crystalline form.

In one embodiment, the anhydrate crystalline form of Compound (IIa) has an X-ray powder diffraction pattern substantially as shown in FIG. 1.

In one embodiment, the anhydrate crystalline form of Compound (IIa) has an X-ray powder diffraction pattern comprising one or more peaks at about 8.0, 11.5, 12.0, 12.5, 13.5, 15.4, 16.8, 17.3, 18.7, and 20.0° 2θ, when measured at about 25° C. with Cu—K$_{\alpha 1}$ radiation (1.5406 Å) with Cu fine focus X-ray tube energized at 40 kV and 30 mA. In another aspect, the anhydrate crystalline form of Compound (IIa) has an X-ray powder diffraction pattern comprising one or more peaks at ±0.2 of 8.0, 11.5, 12.0, 12.5, 13.5, 15.4, 16.8, 17.3, 18.7, and 20.0° 2θ, when measured at about 25° C. with Cu—K$_{\alpha 1}$ radiation (1.5406 Å) with Cu fine focus X-ray tube energized at 40 kV and 30 mA. In yet another aspect, the anhydrate crystalline form of Compound (IIa) has an X-ray powder diffraction pattern comprising one or more peaks at ±0.1 of 8.0, 11.5, 12.0, 12.5, 13.5, 15.4, 16.8, 17.3, 18.7, and 20.0° 2θ, when measured at about 25° C. with Cu—K$_{\alpha 1}$ radiation (1.5406 Å) with Cu fine focus X-ray tube energized at 40 kV and 30 mA.

In one embodiment, the anhydrate crystalline form of Compound (IIa) has an X-ray powder diffraction pattern comprising peaks at ±0.2 of 8.0, 12.0, and 13.5° 2θ, when measured at about 25° C. with Cu—K$_{\alpha 1}$ radiation (1.5406 Å) with Cu fine focus X-ray tube energized at 40 kV and 30 mA. In another embodiment, the anhydrate crystalline form of Compound (IIa) has an X-ray powder diffraction pattern comprising peaks at ±0.2 of 8.0, 12.0, 13.5, 15.4, and 20.0° 2θ, when measured at about 25° C. with Cu—K$_{\alpha 1}$ radiation (1.5406 Å) with Cu fine focus X-ray tube energized at 40 kV and 30 mA Salicylate Salts of Intermediates Salicylate salts of related intermediates are also contemplated for use in the synthesis of elagolix sodium. For example, as shown in Scheme 7, compounds of formula (7-2) where $R^7$ is $C_1$-$C_8$ alkyl; and $R^8$ is bromo or iodo, can be prepared from compounds of formula (7-1), where $R^7$ is $C_1$-$C_8$ alkyl; and $R^8$ is bromo or iodo. The compounds of formula (7-1) where $R^7$ is methyl, ethyl, propyl, isopropyl and the like, and $R^8$ is bromo are disclosed in International Published Application WO2017221144. Compounds of formula (7-1) may be deprotected under suitable conditions for removing the —CO$_2$C(CH$_3$)$_3$ as known to one skilled in the art, including using an acid. Suitable acids include, but are not limited to trifluoroacetic acid, hydrochloric acid, and methanesulfonic acid. Compounds of formula (7-2) may be treated with salicylic acid to form the corresponding salicylate salt. The salicylate salt of compounds of formula (7-2) may be isolated from the reaction mixture using conditions known to one skilled in the art, including in solid form or in crystalline form.

Scheme 7

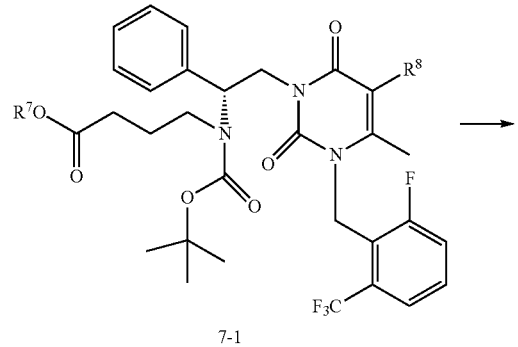

7-1

-continued

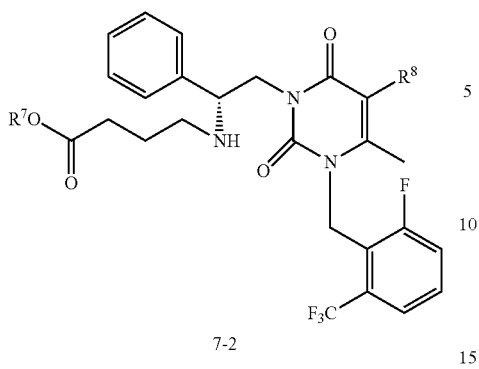

7-2

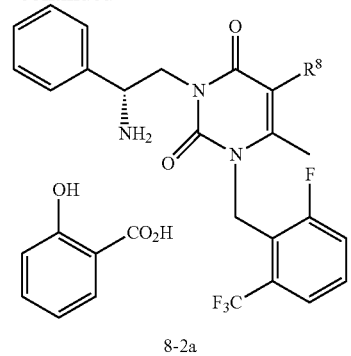

8-2a

Salicylate salts of other related intermediates are also contemplated for use in the synthesis of elagolix sodium. For example, as shown in Scheme 8, compounds of formula (8-1) and (8-2) $R^8$ is bromo or iodo, comprise primary amines which are suitable for salt formation. Compounds of formulae (8-1) and (8-2) may be treated with salicylic acid to form the corresponding salicylate salt. The salicylate salt of compounds of formulae (8-1) and (8-2) may be isolated from the reaction mixture using conditions known to one skilled in the art, including in solid form or in crystalline form.

Scheme 8

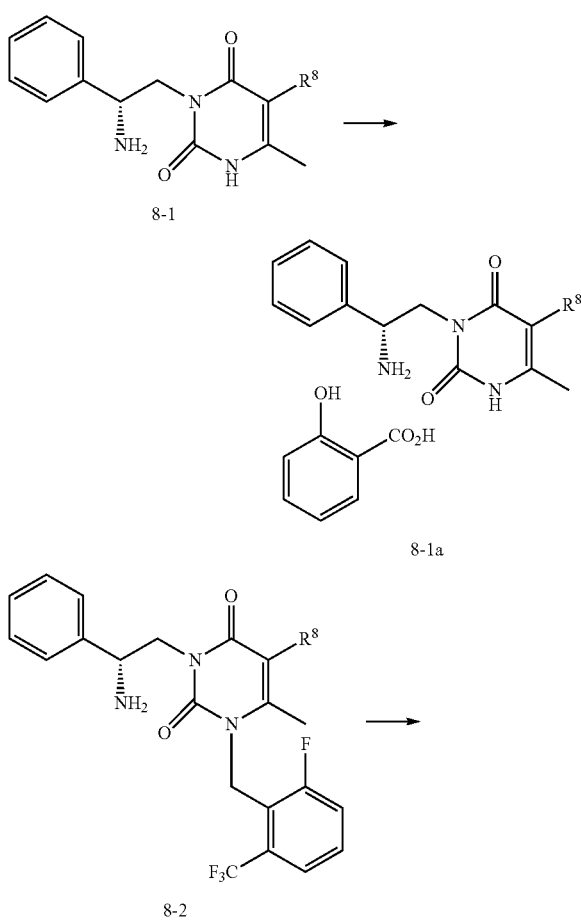

Use of Compound (VI), and its salts including its polymorphic forms, affords a significant advancement in the manufacturability of elagolix sodium. Salts of Compound (VI) may be prepared by treatment of (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid with a suitable base. In some aspects, Compound (VI) may be prepared in the presence of a base and afford the corresponding salt of Compound (VI). Compounds of Formula (VI) may be prepared by treating compound (1-5) with compounds of formula (VIIb) in the presence of a suitable base to afford a salt of Compounds of formula (VI). Suitable bases include, but are not limited to guanidines (including, but not limited to tetramethylguanidine), amidines (including, but not limited to 2,3,4,6,7,8,9,10-octahydropyrimido[1,2-a]azepine, 3,4,6,7,8,9-hexahydro-2H-pyrido[1,2-a]pyrimidine), and substituted or unsubstituted trialkylamines (including, but not limited to triethylamine, trimethylamine, N, N-diisopropylethylamine, or 2-hydroxyethan-1-amine.

Compound (VIa) may be formed by treating compound (1-5) with a compound of formula (VIIb) where $R^{10}$ is ethyl. In one embodiment, Compound (VIa) is a solid. In another embodiment, compound (VIa) is in crystalline form.

In one embodiment, the crystalline form of Compound (VIa) is a solvated crystalline form.

Compound (VIa) Hydrated Polymorph

In one embodiment, the crystalline form of Compound (VIa) is solvated with water. The crystalline form of Compound (VIa) that is a solvated with water is a hydrated crystalline form.

In one embodiment, the crystalline form of Compound (VIa) is Polymorphic Form F.

Figure 17:
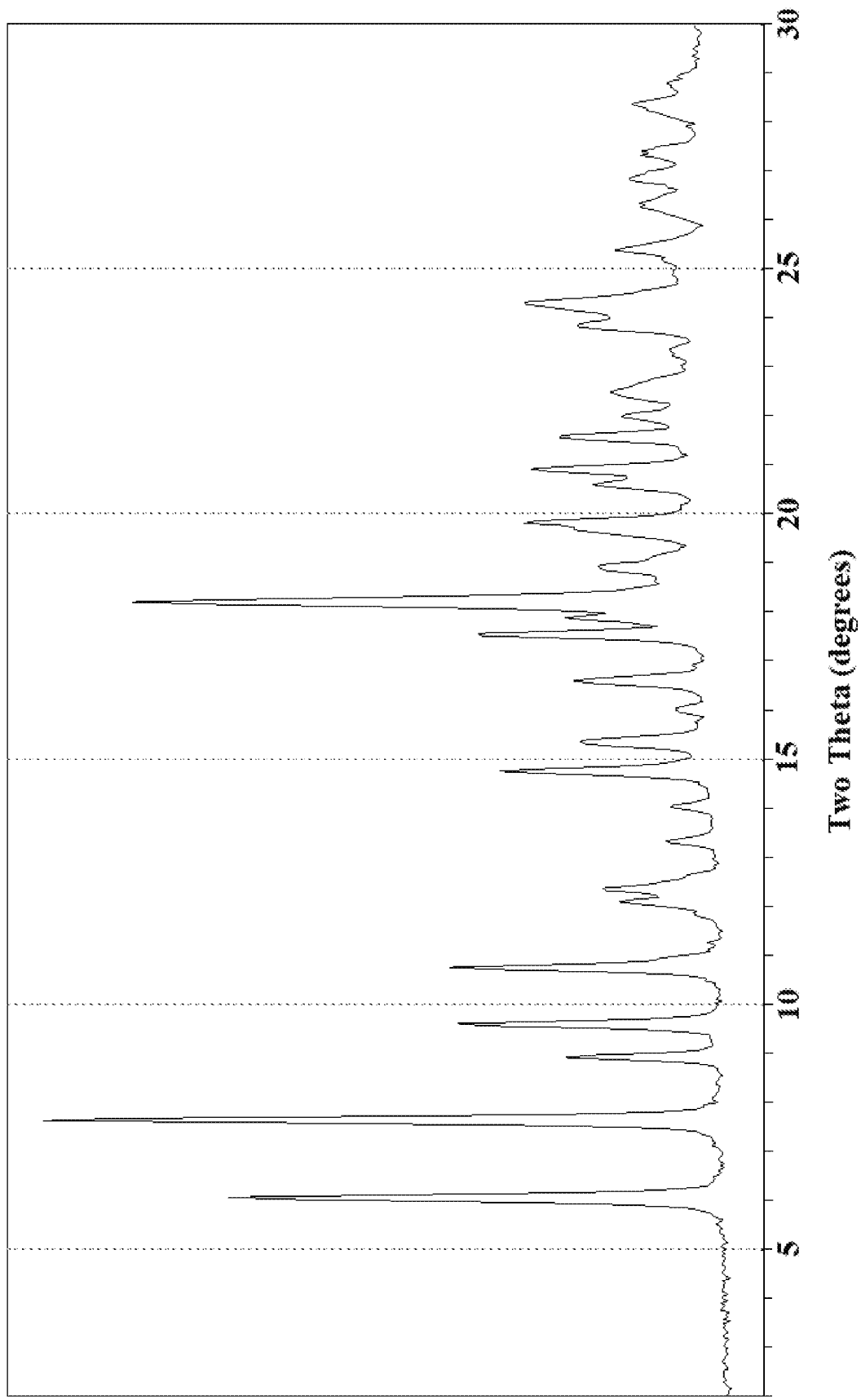
FIG. 17 is a powder X-ray diffraction pattern corresponding to Form F.

In one embodiment, the hydrated crystalline form of Compound (VIa) has an X-ray powder diffraction pattern substantially as shown in FIG. 17.

In one embodiment, the hydrated crystalline form of Compound (VIa) has an X-ray powder diffraction pattern comprising one or more peaks at about 6.0, 7.6, 8.9, 9.6, 10.7, 12.4, 14.8, 15.3, 16.6, 17.5, and 18.2° 2θ, when measured at about 25° C. with Cu—K$_{\alpha1}$ radiation (1.5406 Å) with Cu fine focus X-ray tube energized at 40 kV and 30 mA. In one aspect, the hydrated crystalline form of Compound (VIa) has an X-ray powder diffraction pattern comprising one or more peaks at ±0.2 of 6.0, 7.6, 8.9, 9.6, 10.7, 12.4, 14.8, 15.3, 16.6, 17.5, and 18.2° 2θ, when measured at about 25° C. with Cu—K$_{\alpha1}$ radiation (1.5406 Å) with Cu fine focus X-ray tube energized at 40 kV and 30 mA. In another aspect, the hydrated crystalline form of Compound (VIa) has an X-ray powder diffraction pattern comprising one or more peaks at ±0.1 of 6.0, 7.6, 8.9, 9.6, 10.7, 12.4, 14.8, 15.3, 16.6, 17.5, and 18.2° 2θ, when measured at about 25° C. with Cu—K$_{α1}$ radiation (1.5406 Å) with Cu fine focus X-ray tube energized at 40 kV and 30 mA.

In one embodiment, the hydrated crystalline form of Compound (VIa) has an X-ray powder diffraction pattern comprising peaks at ±0.2 of 6.0, 7.6, and 18.2° 2θ, when measured at about 25° C. with Cu—K$_{α1}$ radiation (1.5406 Å) with Cu fine focus X-ray tube energized at 40 kV and 30 mA. In another embodiment, the hydrated crystalline form of Compound (VIa) has an X-ray powder diffraction pattern comprising peaks at ±0.2 of 6.0, 7.6, 9.6, 14.8, and 18.2° 2θ, when measured at about 25° C. with Cu—K$_{α1}$ radiation (1.5406 Å) with Cu fine focus X-ray tube energized at 40 kV and 30 mA.

The hydrated crystalline form of Compound (VIa) may comprise varying amounts of water. Without wishing to be bound by theory, the water is believed to be able to be removed from the crystal structure without affecting the crystal lattice structure. As such, the level of water in the hydrated crystalline form of Compound (VIa) may vary depending on the level of hydration. The level of hydration may be affected by the humidity of the environment or the extent to which the hydrated crystalline form of Compound (VIa) is dried, for example.

In one embodiment, the hydrated crystalline form of Compound (VIa) comprises between about 0.1 to about 3 mole equivalents of water relative to Compound (VIa). In another embodiment, the hydrated crystalline form of Compound (VIa) comprises between about 0.1 to about 2 mole equivalents of water relative to Compound (VIa). In yet another embodiment, the hydrated crystalline form of Compound (VIa) comprises between about 0.1 to about 1 mole equivalents of water relative to Compound (VIa).

In one embodiment, the hydrated crystalline form of Compound (VIa) comprises between about 0.1 to about 6.0 weight percent of water. In another embodiment, the hydrated crystalline form of Compound (VIa) comprises between about 0.1 to about 4.1 weight percent of water. In yet another embodiment, the hydrated crystalline form of Compound (VIa) comprises between about 0.1 to about 2.2 weight percent of water.

In one embodiment, the hydrated crystalline form of Compound (VIa) comprises about one mole equivalent of water relative to Compound (VIa). In one aspect, the hydrated crystalline form of Compound (VIa) comprises between about 0.6 and 1.4 mole equivalents of water relative to Compound (VIa). In another aspect, the hydrated crystalline form of Compound (VIa) comprises between about 0.8 and 1.2 mole equivalents of water relative to Compound (VIa). In yet another aspect, the hydrated crystalline form of Compound (VIa) comprises between about 0.9 and 1.1 mole equivalents of water relative to Compound (VIa). In one aspect, the hydrated crystalline form of Compound (VIa) comprises between about 1.8 and 2.4 weight percent of water. In another aspect, the hydrated crystalline form of Compound (VIa) comprises between about 1.9 and 2.3 weight percent of water. In yet another aspect, the hydrated crystalline form of Compound (VIa) comprises between about 2.0 and 2.2 weight percent of water.

In one embodiment, the hydrated crystalline form of Compound (VIa) comprises about two mole equivalents of water relative to Compound (VIa). In one aspect, the hydrated crystalline form of Compound (VIa) comprises between about 1.6 and 2.4 mole equivalents of water relative to Compound (VIa). In another aspect, the hydrated crystalline form of Compound (VIa) comprises between about 1.8 and 2.2 mole equivalents of water relative to Compound (VIa). In yet another aspect, the hydrated crystalline form of Compound (VIa) comprises between about 1.9 and 2.1 mole equivalents of water relative to Compound (VIa). In one aspect, the hydrated crystalline form of Compound (VIa) comprises between about 3.7 and 4.3 weight percent of water. In another aspect, the hydrated crystalline form of Compound (VIa) comprises between about 3.8 and 4.2 weight percent of water. In yet another aspect, the hydrated crystalline form of Compound (VIa) comprises between about 3.9 and 4.1 weight percent of water.

In one embodiment, the crystalline form of Compound (VIa) is Polymorphic Form F, and has an endothermic event by DSC between about 160 and 173° C. at a heating rate of 10° C./min. In another embodiment, the crystalline form of Compound (VIa) is Polymorphic Form F, and has an endothermic event by DSC between about 165 and 169° C. at a heating rate of 10° C./min.

Compound (VIa) Nonhydrate and Nonsolvate Polymorphic Forms

In one embodiment, the crystalline form of Compound (VIa) is a nonhydrate crystalline form. In another embodiment, the crystalline form of Compound (VIa) is a substantially water-free crystalline form.

In one embodiment, the crystalline form of Compound (VIa) is a nonhydrate/nonsolvate crystalline form.

In one embodiment, the crystalline form of Compound (VIa) is Polymorphic Form G.

Figure 15:
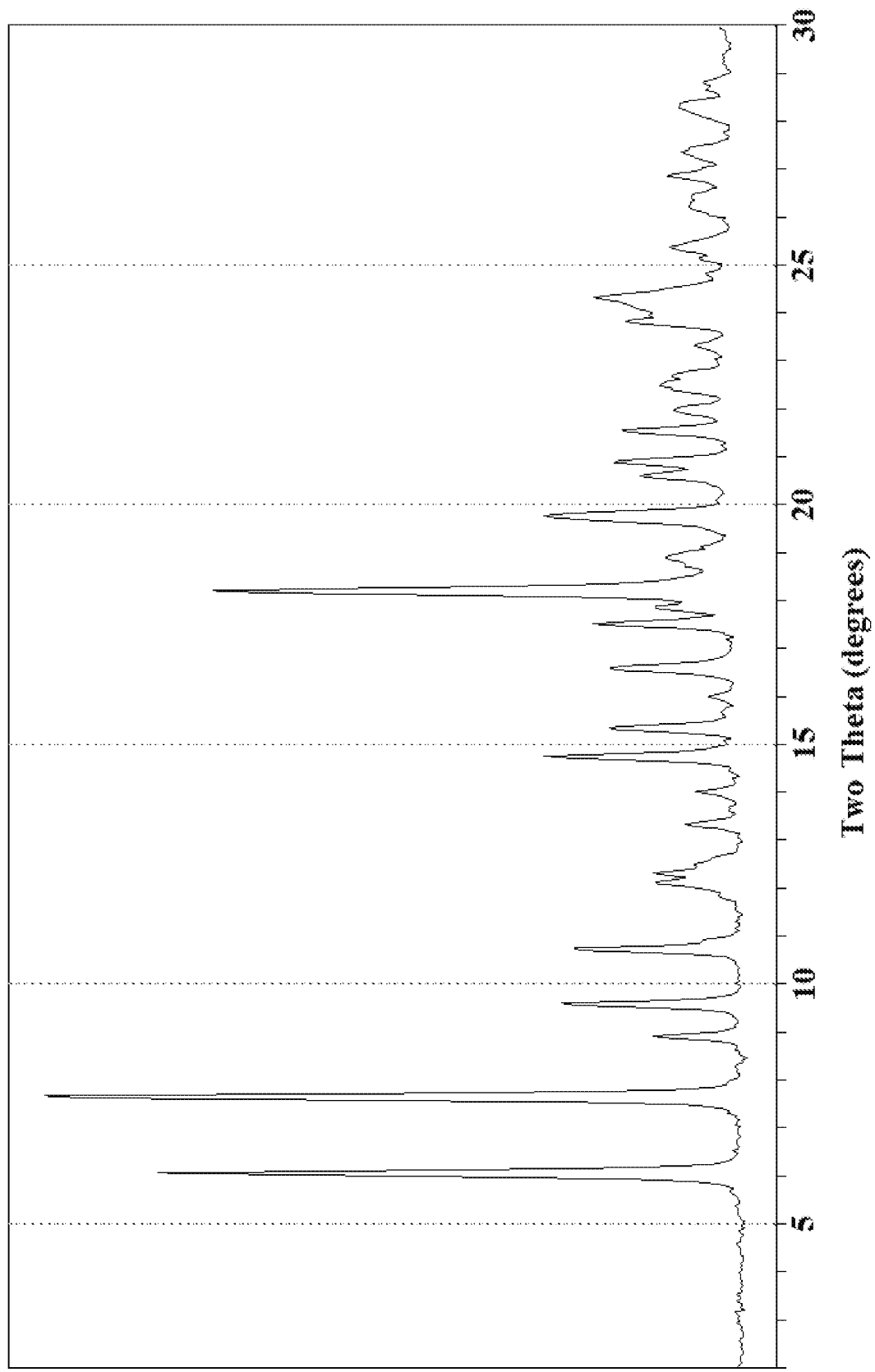
FIG. 15 is a powder X-ray diffraction pattern corresponding to Form G.

In one embodiment, a nonhydrate crystalline form of Compound (VIa) has an X-ray powder diffraction pattern substantially as shown in FIG. 15.

In one embodiment, the nonhydrate crystalline form of Compound (VIa) has an X-ray powder diffraction pattern comprising one or more peaks at about 6.1, 7.7, 8.9, 9.6, 10.7, 12.3, 14.7, 15.3, 16.6, 17.5, and 18.2° 2θ, when measured at about 25° C. with Cu—K$_{α1}$ radiation (1.5406 Å) with Cu fine focus X-ray tube energized at 40 kV and 30 mA.

In another embodiment, the nonhydrate crystalline form of Compound (VIa) has an X-ray powder diffraction pattern comprising one or more peaks at ±0.2 of 6.1, 7.7, 8.9, 9.6, 10.7, 12.3, 14.7, 15.3, 16.6, 17.5, and 18.2° 2θ, when measured at about 25° C. with Cu—K$_{α1}$ radiation (1.5406 Å) with Cu fine focus X-ray tube energized at 40 kV and 30 mA. In one aspect, the crystalline form of Compound (VIa) is substantially water free and has an X-ray powder diffraction pattern comprising one or more peaks at ±0.2 of 6.1, 7.7, 8.9, 9.6, 10.7, 12.3, 14.7, 15.3, 16.6, 17.5, and 18.2° 2θ, when measured at about 25° C. with Cu—K$_{α1}$ radiation (1.5406 Å) with Cu fine focus X-ray tube energized at 40 kV and 30 mA.

In yet another embodiment, the nonhydrate crystalline form of Compound (VIa) has an X-ray powder diffraction pattern comprising one or more peaks at ±0.1 of 6.1, 7.7, 8.9, 9.6, 10.7, 12.3, 14.7, 15.3, 16.6, 17.5, and 18.2° 2θ, when measured at about 25° C. with Cu—K$_{α1}$ radiation (1.5406 Å) with Cu fine focus X-ray tube energized at 40 kV and 30 mA.

In one embodiment, the nonhydrate crystalline form of Compound (VIa) has an X-ray powder diffraction pattern comprising peaks at ±0.2 of 6.1, 7.7, and 18.2° 2θ, when measured at about 25° C. with Cu—K$_{α1}$ radiation (1.5406 Å) with Cu fine focus X-ray tube energized at 40 kV and 30 mA. In another embodiment, the nonhydrate crystalline form of Compound (VIa) has an X-ray powder diffraction pattern comprising peaks at ±0.2 of 6.1, 7.7, 9.6, 14.7, and 18.2° 2θ, when measured at about 25° C. with Cu—K$_{α1}$ radiation (1.5406 Å) with Cu fine focus X-ray tube energized at 40 kV and 30 mA.

In one embodiment, the crystalline form of Compound (VIa) is Polymorphic Form G, and has an endothermic event by DSC between about 163 and 173° C. In another embodiment, the crystalline form of Compound (VIa) is Polymorphic Form G, and has an endothermic event by DSC between about 165 and 171° C. In yet another embodiment, the crystalline form of Compound (VIa) is Polymorphic Form G, and has an endothermic event by DSC between about 167 and 169° C.

In one embodiment, the crystalline form of Compound (VIa) is Polymorphic Form H.

Figure 16:
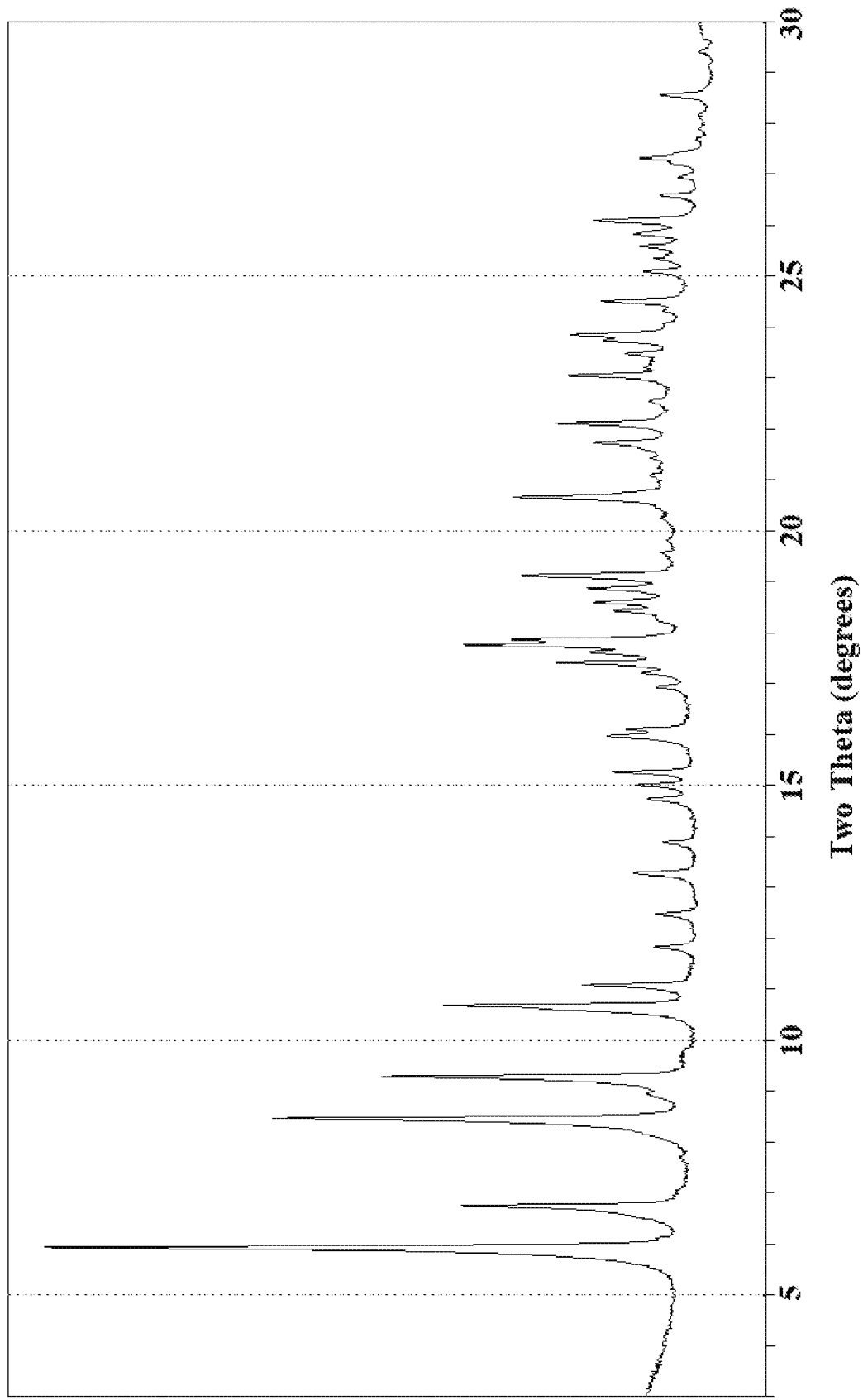
FIG. 16 is a powder X-ray diffraction pattern corresponding to Form H.

In one embodiment, the nonhydrate/nonsolvate crystalline form of Compound (VIa) has an X-ray powder diffraction pattern substantially as shown in FIG. 16.

In one embodiment, the nonhydrate/nonsolvate crystalline form of Compound (VIa) has an X-ray powder diffraction pattern comprising one or more peaks at about 5.9, 6.7, 8.5, 9.3, 10.7, 11.1, 15.3, 16.0, 17.4, and 17.8° 2θ, when measured at about 25° C. with Cu—K$_{α1}$ radiation (1.5406 Å) with Cu fine focus X-ray tube energized at 40 kV and 30 mA. In one aspect, the nonhydrate/nonsolvate crystalline form of Compound (VIa) has an X-ray powder diffraction pattern comprising one or more peaks at ±0.2 of 5.9, 6.7, 8.5, 9.3, 10.7, 11.1, 15.3, 16.0, 17.4, and 17.8° 2θ, when measured at about 25° C. with Cu—K$_{α1}$ radiation (1.5406 Å) with Cu fine focus X-ray tube energized at 40 kV and 30 mA. In another aspect, the nonhydrate/nonsolvate crystalline form of Compound (VIa) has an X-ray powder diffraction pattern comprising one or more peaks at ±0.1 of 5.9, 6.7, 8.5, 9.3, 10.7, 11.1, 15.3, 16.0, 17.4, and 17.8° 2θ, when measured at about 25° C. with Cu—K$_{α1}$ radiation (1.5406 Å) with Cu fine focus X-ray tube energized at 40 kV and 30 mA.

In one embodiment, the nonhydrate/nonsolvate crystalline form of Compound (VIa) has an X-ray powder diffraction pattern comprising peaks at ±0.2 of 5.9, 8.5, and 9.3° 2θ, when measured at about 25° C. with Cu—K$_{α1}$ radiation (1.5406 Å) with Cu fine focus X-ray tube energized at 40 kV and 30 mA. In another embodiment, the nonhydrate/nonsolvate crystalline form of Compound (VIa) has an X-ray powder diffraction pattern comprising peaks at ±0.2 of 5.9, 6.7, 8.5, 9.3, and 17.8° 2θ, when measured at about 25° C. with Cu—K$_{α1}$ radiation (1.5406 Å) with Cu fine focus X-ray tube energized at 40 kV and 30 mA.

In one embodiment, the crystalline form of Compound (VIa) is Polymorphic Form H, and has a first endothermic event by DSC between about 98 and 134° C.; and a second endothermic event between about 162 and 169° C. In another embodiment, the crystalline form of Compound (VIa) is Polymorphic Form H, and has a first endothermic event by DSC between about 100 and 130° C.; and a second endothermic event between about 165 and 169° C. It is to be understood that only one of the first or second endothermic events may be observed by DSC, depending on the conditions in which the DSC data is collected.

Compound (VIa) Dimethyl Sulfoxide Solvated Polymorph

In one embodiment, the crystalline form of Compound (VIa) is solvated with dimethyl sulfoxide. The crystalline form of Compound (VIa) that is solvated with dimethyl sulfoxide is a dimethyl sulfoxide solvated crystalline form.

In one embodiment, the crystalline form of Compound (VIa) is Polymorphic Form I.

Figure 18:
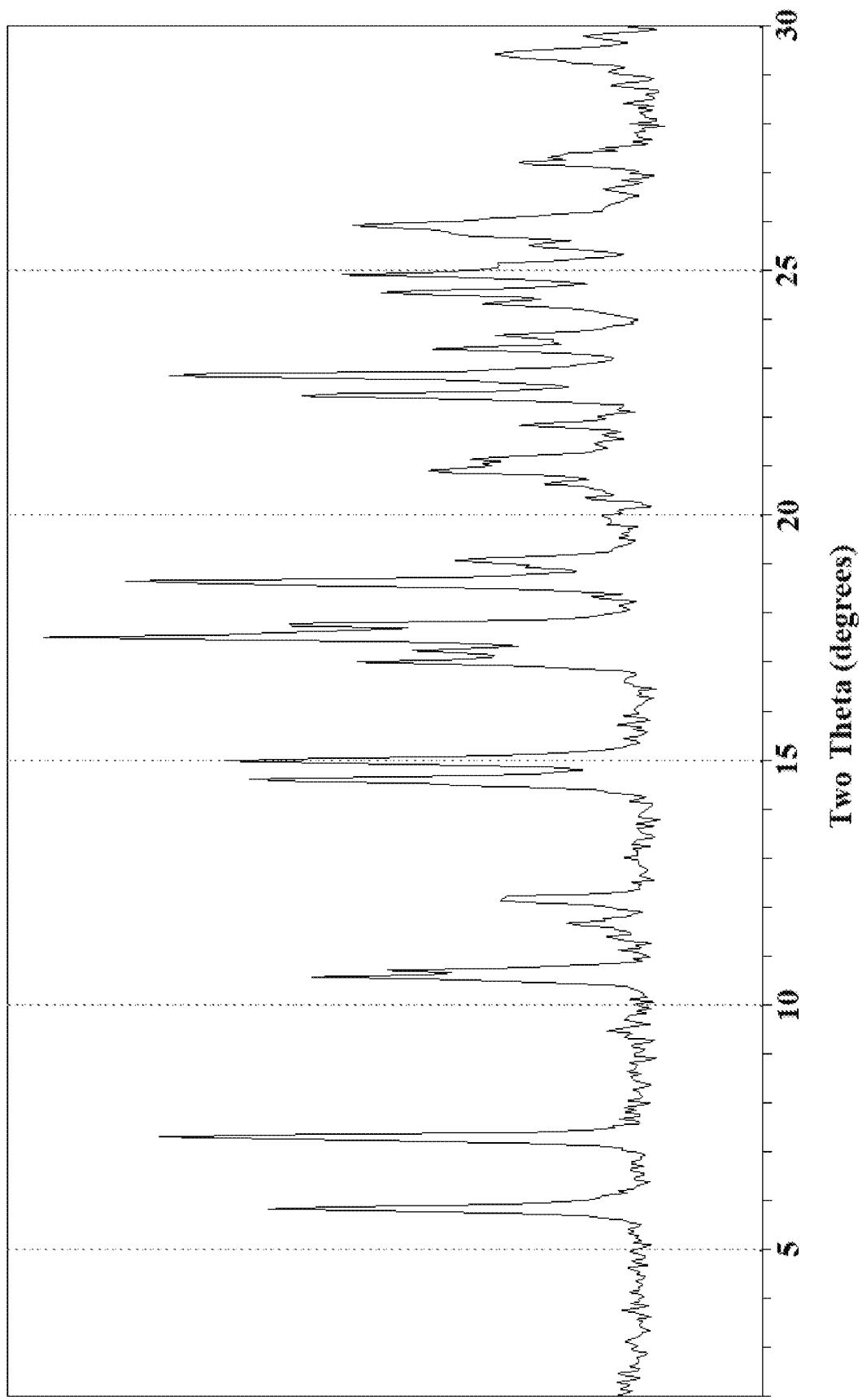
FIG. 18 is a powder X-ray diffraction pattern corresponding to Form I.

In one embodiment, the dimethyl sulfoxide solvated crystalline form of Compound (VIa) has an X-ray powder diffraction pattern substantially as shown in FIG. 18.

In one embodiment, the dimethyl sulfoxide solvated crystalline form of Compound (VIa) has an X-ray powder diffraction pattern comprising one or more peaks at about 5.8, 7.3, 10.6, 12.1, 14.6, 15.0, 17.0, 17.5, 18.6, and 22.9° 2θ, when measured at about 25° C. with Cu—K$_{α1}$ radiation (1.5406 Å) with Cu fine focus X-ray tube energized at 40 kV and 30 mA. In another embodiment, the dimethyl sulfoxide solvated crystalline form of Compound (VIa) has an X-ray powder diffraction pattern comprising one or more peaks at ±0.2 of 5.8, 7.3, 10.6, 12.1, 14.6, 15.0, 17.0, 17.5, 18.6, and 22.9° 2θ, when measured at about 25° C. with Cu—K$_{α1}$ radiation (1.5406 Å) with Cu fine focus X-ray tube energized at 40 kV and 30 mA. In yet another embodiment, the dimethyl sulfoxide solvated crystalline form of Compound (VIa) has an X-ray powder diffraction pattern comprising one or more peaks at ±0.1 of 5.8, 7.3, 10.6, 12.1, 14.6, 15.0, 17.0, 17.5, 18.6, and 22.9° 2θ, when measured at about 25° C. with Cu—K$_{α1}$ radiation (1.5406 Å) with Cu fine focus X-ray tube energized at 40 kV and 30 mA.

In one embodiment, the dimethyl sulfoxide solvated crystalline form of Compound (VIa) has an X-ray powder diffraction pattern comprising peaks at ±0.2 of 5.8, 7.3, and 17.5° 2θ, when measured at about 25° C. with Cu—K$_{α1}$ radiation (1.5406 Å) with Cu fine focus X-ray tube energized at 40 kV and 30 mA. In another embodiment, the dimethyl sulfoxide solvated crystalline form of Compound (VIa) has an X-ray powder diffraction pattern comprising peaks at ±0.2 of 5.8, 7.3, 10.6, 15.0, and 17.5° 2θ, when measured at about 25° C. with Cu—K$_{α1}$ radiation (1.5406 Å) with Cu fine focus X-ray tube energized at 40 kV and 30 mA In one embodiment, the crystalline form of Compound (VIa) is Polymorphic Form I, and has a first endothermic event by DSC between about 90 and 105° C.; and a second endothermic event between about 105 and 155° C. In another embodiment, the crystalline form of Compound (VIa) is Polymorphic Form I, and has a first endothermic event by DSC between about 99 and 103° C.; and a second endothermic event between about 110 and 150° C. It is to be understood that only one of the first or second endothermic events may be observed by DSC, depending on the conditions in which the DSC data is collected.

Compound (VIa) Dichloromethane Solvated Polymorph

In one embodiment, the crystalline form of Compound (VIa) is solvated with dichloromethane. The crystalline form of Compound (VIa) that is solvated with dichloromethane is a dichloromethane solvated crystalline form.

In one embodiment, the crystalline form of Compound (VIa) is Polymorphic Form J.

Figure 19:
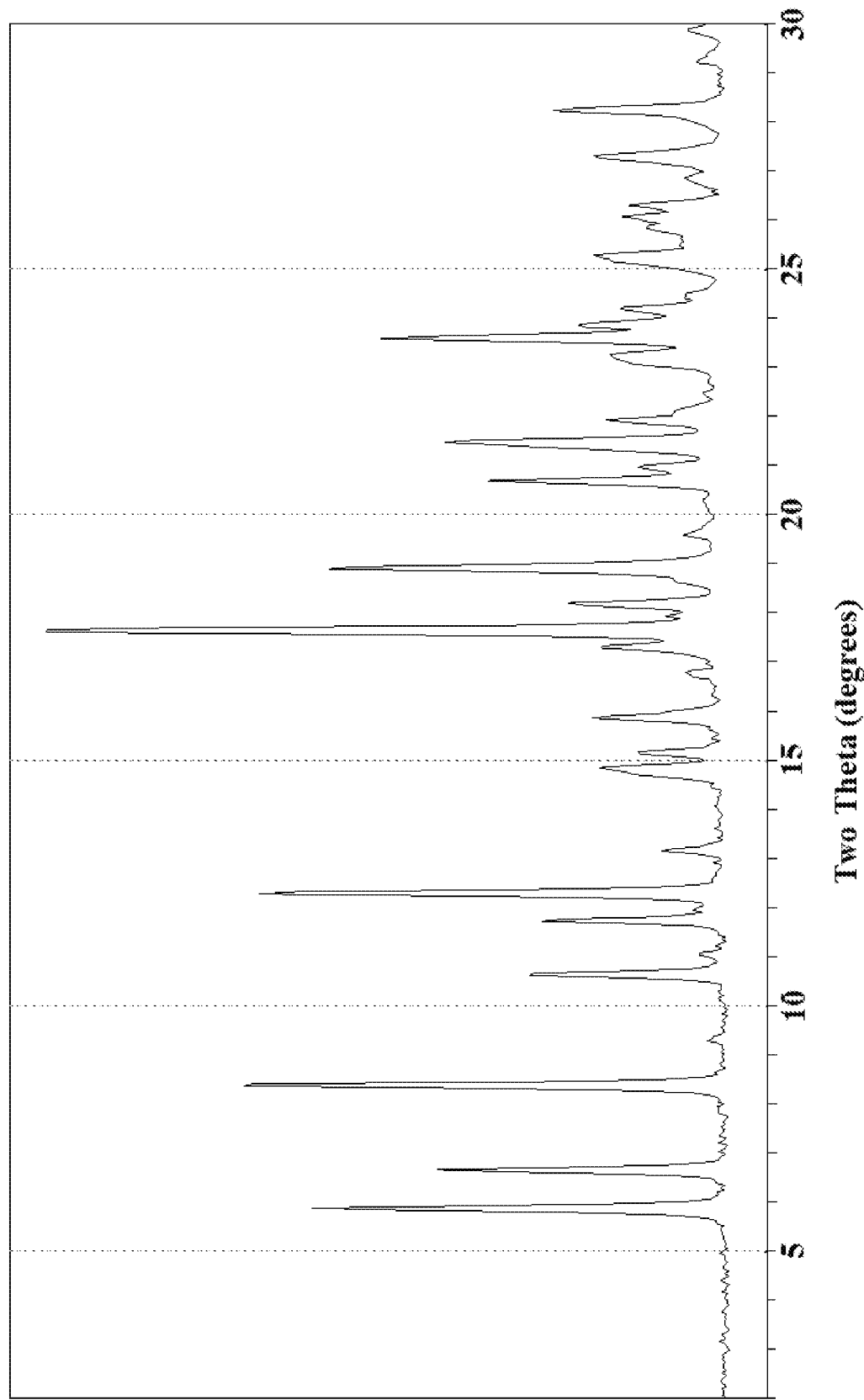
FIG. 19 is a powder X-ray diffraction pattern corresponding to Form J.

In one embodiment, the dichloromethane solvated crystalline form of Compound (VIa) has an X-ray powder diffraction pattern substantially as shown in FIG. 19.

In one embodiment, the dichloromethane solvated crystalline form of Compound (VIa) has an X-ray powder diffraction pattern comprising one or more peaks at about 5.9, 6.6, 8.4, 10.6, 11.7, 12.3, 14.8, 15.9, 17.6, 18.2, 18.9, and 20.7° 2θ, when measured at about 25° C. with Cu—K$_{α1}$ radiation (1.5406 Å) with Cu fine focus X-ray tube energized at 40 kV and 30 mA. In another embodiment, the dichloromethane solvated crystalline form of Compound (VIa) has an X-ray powder diffraction pattern comprising one or more peaks at ±0.2 of 5.9, 6.6, 8.4, 10.6, 11.7, 12.3, 14.8, 15.9, 17.6, 18.2, 18.9, and 20.7° 2θ, when measured at about 25° C. with Cu—K$_{α1}$ radiation (1.5406 Å) with Cu fine focus X-ray tube energized at 40 kV and 30 mA. In yet another embodiment, the dichloromethane solvated crystalline form of Compound (VIa) has an X-ray powder diffraction pattern comprising one or more peaks at ±0.1 of 5.9, 6.6, 8.4, 10.6, 11.7, 12.3, 14.8, 15.9, 17.6, 18.2, 18.9, and 20.7° 2θ, when measured at about 25° C. with Cu—$K_{\alpha 1}$ radiation (1.5406 Å) with Cu fine focus X-ray tube energized at 40 kV and 30 mA.

In one embodiment, the dichloromethane solvated crystalline form of Compound (VIa) has an X-ray powder diffraction pattern comprising peaks at ±0.2 of 11.7, 18.9, and 20.7° 2θ, when measured at about 25° C. with Cu—$K_{\alpha 1}$ radiation (1.5406 Å) with Cu fine focus X-ray tube energized at 40 kV and 30 mA. In another embodiment, the dichloromethane solvated crystalline form of Compound (VIa) has an X-ray powder diffraction pattern comprising peaks at ±0.2 of 5.9, 11.7, 17.6, 18.9, and 20.7° 2θ, when measured at about 25° C. with Cu—$K_{\alpha 1}$ radiation (1.5406 Å) with Cu fine focus X-ray tube energized at 40 kV and 30 mA.

In one embodiment, the dichloromethane solvated crystalline form of Compound (VIa) has a $P2_1$ space group, a unit cell a value of about 9.9 Å, a unit cell b value of about 14.8 Å, and a unit cell c value of about 29.7 Å. In one aspect, the dichloromethane solvated crystalline form of Compound (VIa) has a $P2_1$ space group, a unit cell a value of about 9.9 Å, a unit cell b value of about 14.8 Å, a unit cell c value of about 29.7 Å, a cell angle α of about 90.0°, a cell angle θ of about 90.3°, and a cell angle γ of about 90.0°.

In one embodiment, the crystalline form of Compound (VIa) is Polymorphic Form J, and has an endothermic event by DSC between about 163 and 174° C. In another embodiment, the crystalline form of Compound (VIa) is Polymorphic Form J, and has a first endothermic event by DSC between about 167 and 171° C.

EXAMPLES

In order that the invention described herein may be more fully understood, the following examples are set forth. The synthetic examples described in this application are offered to illustrate the compounds, polymorphs, pharmaceutical compositions, and processes provided herein and are not to be construed in any way as limiting their scope.

Compounds and intermediates are named by using Name 2017.2.1 (File Version N40E41, Build 96719) or Name 2018.1.1 (File Version N50E41, Build 103230) naming algorithm by Advanced Chemical Development.

Common abbreviations well known to those with ordinary skills in the synthetic art which are used throughout: Bu for n-butyl; dba for dibenzylideneacetone; DMF for N,N-dimethylformamide; DMSO for dimethyl sulfoxide; EA or EtOAc for ethyl acetate; MeOH for methanol; MTBE for methyl tert-butyl ether; OAc for —OC(O)CH$_3$; TFA for trifluoroacetic acid; and THF for tetrahydrofuran.

Other abbreviations well known to those with ordinary skills in the art which are used throughout: atm for atmospheres of gas pressure; DSC for differential scanning calorimetry; DVS for dynamic vapor sorption; ESI for electrospray ionization; g for gram; h for hour or hours; HPLC for high performance liquid chromatography; LC/MS or LCMS or LC-MS for liquid chromatography—mass spectrometry; μL for microliter; μm for micrometer; mg for milligram; min for minute; mL for milliliter; mmol for millimoles; MS for mass spectrum; NMR for nuclear magnetic resonance; PXRD for powder x-ray diffraction; psi for pounds per square inch; rt for ambient temperature; RH for relative humidity; SFC for supercritical fluid chromatography; TGA for thermo gravimetric analysis; and UPLC for ultra high pressure chromatography.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer or a 500 MHz spectrometer. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of doublets of doublets (ddd), doublet of doublets of doublets of doublets (dddd), doublet of doublets of quartets (ddq), doublet of doublets of triplets (ddt), doublet of quartets (dq), doublet of triplets of doublets (dtd), heptet (hept), triplet (t), triplet of doublets of doublets (tdd), triplet of quartets (tq), quartet (q), quartet of doublets (qd), quartet of triplets (qt), quintuplet (quin), multiplet (m) and broad (br).

For FIGS. 1, 2, 4, 15, 17, and 18, PXRD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromater was utilized to provide monochromatic $K_{\alpha 1}$ radiation (λ=1.5406 Å). The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the MDI Jade software (version 9.0, Materials Data, Inc., Livermore, Calif.). Samples for PXRD analysis were prepared by spreading the wet cake or solid sample powder in a thin layer on an aluminum sample holder and gently leveling with a glass microscope slide. The aluminum sample holder was then mounted on the rotating sample holder of the XRG 3000 diffractometer and diffraction data was collected at ambient conditions.

For FIGS. 2 and 5, PXRD diffractograms were acquired using PANalytical X'Pert Pro diffractometer using Ni-filtered Cu—$K_{\alpha 1}$ (45 kV/40 mA) radiation and a step size of 0.02° 2-theta and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers. Hazardous samples were covered with Kapton film.

For FIGS. 16 and 19, PXRD diffractograms were acquired using a D8 Advance diffractometer using Cu—$K_{\alpha 1}$ radiation (λ=1.5406 Å) with germanium monochromator at ambient temperature. The diffractometer was operated at 40 kV. Diffraction data were collected in the 2θ range 3-41.5° 2θ. Detector scan on solid state LynxEye detector was performed using 0.016° per step with 2-10 sec/step scan speed. The samples were measured in 8 mm long glass capillary with 0.5 mm outer diameter.

For FIG. 7, Differential Scanning calorimetry (DSC) data was collected with a DSC (Q-2000, TA Instruments, New Castle, Del.) equipped with Universal Analysis 2000 software (Version 4.5 Å, TA Instruments, New Castle, Del.) to determine the DSC thermal traces. The temperature axis was calibrated with biphenyl, indium, and tin standards. The cell constant was calibrated with indium. Unless otherwise stated, the sample (2-5 mg) was encapsulated in a ventilated aluminum pan, and heated at a rate of 10° C./minute under a nitrogen gas flow of 50 mL/minute during the study. For FIG. 8, DSC was conducted with a TA Instruments Q100 differential scanning calorimeter equipped with an autosampler and a refrigerated cooling system under 40 mL/min $N_2$ purge. DSC thermograms were obtained at 15° C./min in crimped Al pans. For FIGS. 10, and 12, DSC was conducted with a DSC922e instrument (Mettler-Toledo) which was calibrated for temperature and enthalpy with indium. Samples were sealed in standard 40 µL aluminum pans, pin-holed and heated in the DSC from 25° C. to 300° C., at a heating rate of 10° C./min under a 50 mL/min dry N2 purge.

For FIG. 6, Thermo Gravimetric Analysis (TGA) was run with TA instruments. Data was collected on a thermal balance (Q-5000, TA Instruments, New Castle, Del.) equipped with a data analyzer (Universal Analysis 2000, version 4.5 Å, TA Instruments, New Castle, Del.). During experiments, the furnace was purged with nitrogen at 60 mL/minute, while the balance chamber was purged at 40 mL/minute. Temperature of the TGA furnace was calibrated using curie points of aluminum and nickel. Sample size ranged from 2 to 20 mg, and a heating rate of 10° C./minute was used. For TGA-MS, the thermogravimetric analysis part was the same as above. The mass of evolved gas was analyzed with PFEIFFER GSD 301 T3 ThermoStar (PFEIFFER Vacuum, Asslar, Germany). The instrument was operated and data evaluated with Software Quadstar 32-bit (V7.01, Inficon, LI-9496 Balzers, Liechtenstein). For FIG. 8, TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N2 flow and heating rate of 15° C./min in Pt or Al pans. IR spectra were collected at 4 $cm^{-1}$ resolution and 32 scans at each time point. For FIGS. 13 and 20, TGA was conducted with a TGA/DSC 3+ STARe system (Mettler-Toledo). The TGA was calibrated for temperature with indium and aluminum. Samples (about 2 mg) were weighed into 100 µL aluminum crucibles and sealed. The seals were pin-holed, and the crucibles heated in the TGA from 25 to 300° C. at 10° C./min with a dry N2 purge.

Figure 9:
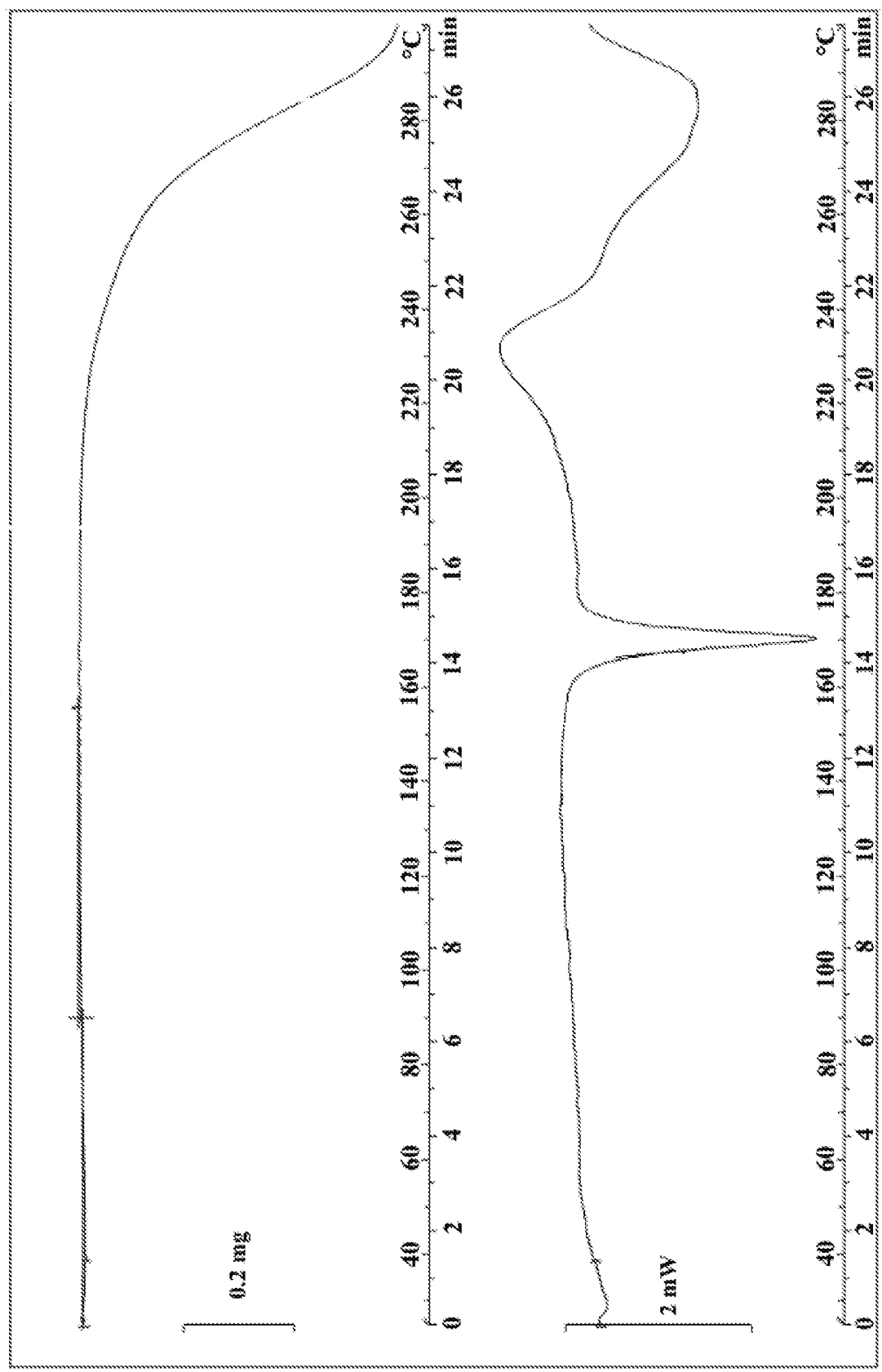
FIG. 9 is a TGA/DSC thermogram of Form G.
Figure 11:
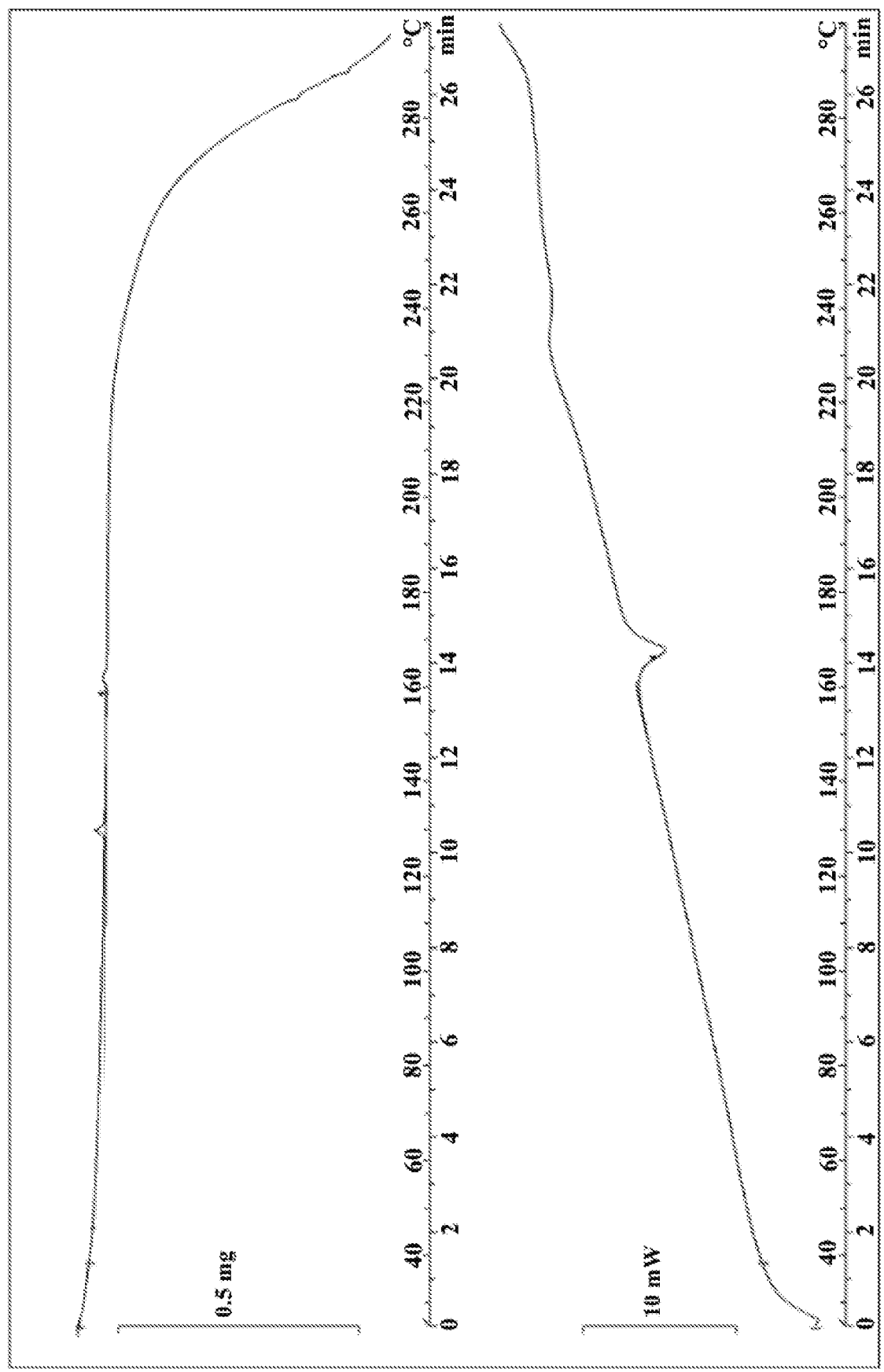
FIG. 11 is a TGA/DSC thermogram of Form F.
Figure 14:
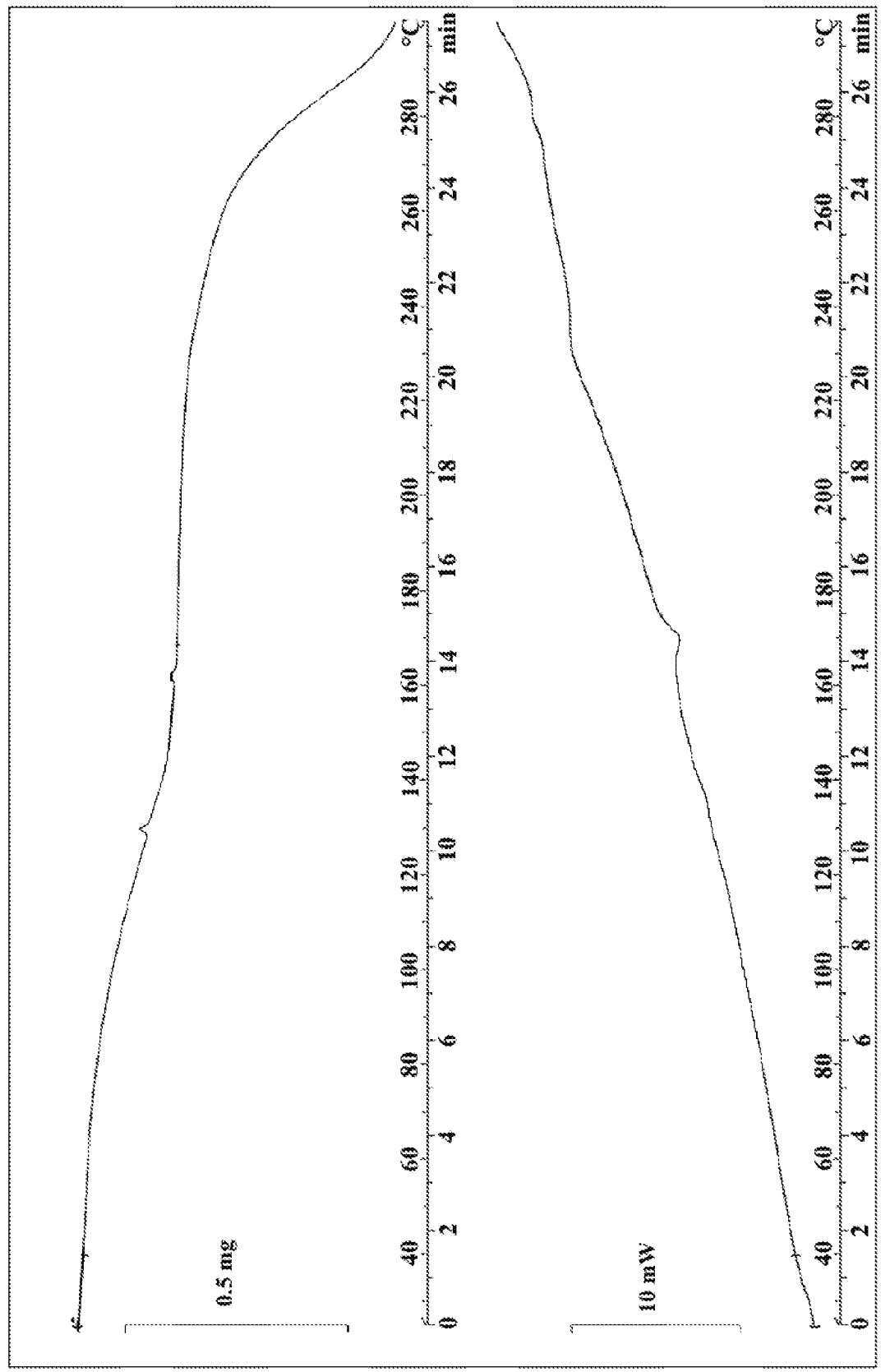
FIG. 14 is a TGA/DSC thermogram of Form J.

For FIGS. 9, 11, and 14, TGA/DSC thermograms were collected using a Mettler TGA/DSC 1 (Mettler-Toledo International Incorporated, Scwezenbach, Switzerland) equipped with a robotic autosampler. The instrument was operated and data evaluated with the Stare software (V9.01, Mettler-Toledo International Incorporated, Scwezenbach, Switzerland). The temperature axis was calibrated with indium and aluminum standards. The sample powders were encapsulated in an appropriate pan and scanned at certain rate as specified in TGA thermogram plots. A 20 mL/min nitrogen purge to the sample chamber was used. Temperature of the TGA furnace was calibrated using curie points of aluminum, nickel and Zinc. Generally, sample size ranged from 2 to 20 mg, and a heating rate of 10° C./min was used unless specified otherwise.

For thermal analyses including, for example, DSC and TGA, the temperature at which thermal events occur is dependent upon the conditions in which the data was collected. The temperatures at which thermal events are reported herein were collected according to the conditions described above. It is to be understood that if thermal events are recorded under different conditions, the temperature at which the thermal events occur may be different. For example, the temperature variance may be 5%. In other aspects the temperature variance may be 3%. In yet other aspects, the temperature variance may be 1%.

The BET (Brunauer, Emmett and Teller) specific surface area was determined from nitrogen adsorption isotherm at 77° K using a surface area analyzer (Tristar 3020, Micromeritics, Norcross, Ga.). A sample of approximately 1-2 g was first outgassed under vacuum for 2 hours at 50° C. prior to nitrogen adsorption experiment. The multipoint measurement method was used according to USP <846>. The quantity adsorbed was measured between 0.05 and 0.3 relative pressure. A minimum of 5 data points between this pressure range was determined to obtain the specific surface area using the BET equation.

Particle size distribution was measured by laser diffraction using a Malvern Mastersizer 2000S (Malvern Panalytical Ltd., Malvern, United Kingdom) in the wet dispersion mode. The liquid dispersion accessory was first filled with a solution of 0.025% w/v lecithin in HPLC n-heptane. After laser background intensity was measured, approximately 40 mg of sample was added directly to the liquid dispersion accessory to obtain a target laser obscuration between 5 and 22%. Particle size distribution measurement was started immediately upon addition of the sample. The following method parameters were used: Calculation theory—Mie; Measurement model—general purpose; Measurement sensitivity—normal; Dispersant refractive index—1.39; Background time—30 s; Measurement time—30 s; Stirrer speed—1500 rpm; Measurement cycle—1.

Flow properties of each sample were characterized using a Schulze ring shear tester RST-XS (Dietmar Schulze Schutgutmesstechnik, Wolfenbüttel, Germany). A standard annular cell of a cross-sectional area of 24 $cm^2$ and a volume of 30 $cm^3$ is used to measure the yield loci. All experiments were performed under ambient conditions immediately after the sample was removed from the sample container. During each measurement, the powder sample was first pre-sheared under a pre-consolidation stress of 1 kPa until a steady-state was reached. The pre-sheared powder was then subjected to shear under four normal stress levels of 275, 390, 600 and 275 kPa to obtain the yield locus (plot of shear stress at failure as a function of the normal stress). Between each shear points, the sample was pre-consolidated at 1 kPa. From the yield locus, the major principle stress ($\sigma$) and unconfined yield strength ($f_c$) were derived by drawing two critical Mohr stress circles with the software RST-CONTROL 95 (Dietmar Schulze Schuttgiit-messtechnik, Wolfenbüttel, Germany). The major principle stress ($\sigma$) was obtained from the Mohr stress circle which is tangential to the yield locus and intersects at the point of normal and shear stresses at steady state flow. The unconfined yield strength ($f_c$) was obtained from the Mohr stress circle which is tangential to the yield locus and runs through the origin. Flow function coefficient ($ff_c=\sigma/f_c$) was used to characterize the flow of the powder sample.

The bulk density of the sample was obtained by measurement in a graduated cylinder. A 50 mL graduated cylinder (readable to 1 mL) was used in all measurement. First, the tared weight of the cylinder was obtained with a balance (readable to ±0.01 g). Sufficient amount of sample was then transferred into the cylinder, gently to avoid compaction of the sample, to a volume between 30 and 50 mL. The total weight of the sample and cylinder was then measured with the balance (readable to ±0.01 g), and the net sample weight was calculated. The bulk density is the weight of the sample divided by the apparent volume (to the nearest graduated unit).

HPLC Method A

HPLC Method A was used to determine the purity of Compound (II) or Compound (IIa). Samples of Compound (II) were analyzed for purity using High Performance Liquid Chromatography (HPLC) with a UV detector, using an Ascentis Express C8, 2.7 μm column (150 mm×4.6 mm) or equivalent. A gradient of 0.1% (v/v) phosphoric acid in water/methanol (90/10, v/v) (A) and 0.1% (v/v) phosphoric acid in acetonitrile/methanol (90/10, v/v) (B) was used, at a flow rate of 1.2 mL/min (0-3.0 min 97% A, 3.0-30.0 min linear gradient 97-30% A, 30.0-35.0 min linear gradient 30-5% A, 35.0-40.0 min 5% A, 40.0-40.1 min linear gradient 5-95% A, 40.1-45.0 min, 97% A). An injection volume of 10 μL was used, UV detection was set to collect at a wavelength of 210 nm, autosampler was at ambient temperature, and the column temperature was set at 35° C.

Samples for HPLC analysis by Method A were prepared by dissolving a sample of Compound (II) in a diluent of acetonitrile/water (50/50, v/v) at a concentration of approximately 0.2 mg/mL.

Individual impurity levels were determined by calculating the peak area (PA) percentage according to the following formula:

$$\text{Individual Impurity Peak Area \%} = 100 \times \frac{PA \text{ Impurity}}{PA \text{ Total}}$$

$PA_{Impurity}$=peak area of individual impurity in sample
$PA_{Total}$=sum of all peak areas in the sample equal to or greater than 0.05 peak area %, excluding the salicylic acid peak The Compound (IIa) level is determined by calculating weight percent of Compound (IIa) in the sample of the Compound (II). A reference standard of Compound (IIa) of known purity is prepared at a known concentration of approximately 0.2 mg/mL using a diluent of acetonitrile/water (50/50, v/v). The reference standard concentration is corrected for the purity of the standard. The reference standard is used to determine the weight percent of Compound (IIa) in the sample of the Compound (II).

Salicylic acid eluted prior to Compound (IIa). The relative order of elution of select impurities relative to salicylic acid and Compound (IIa) are as follows in order of earlier eluting to later eluting peaks:
  a) Compound (xi);
  b) salicylic acid;
  c) Compound (IIa);
  d) 5-(2-fluoro-3-methoxyphenyl)-1-{[2-fluoro-6-(trifluoromethyl)phenyl]methyl}-6-methylpyrimidine-2,4(1H,3H)-dione;
  e) Compound (xii);
  f) Compound (xiv); and
  g) Compound (xiii).

HPLC Method B

HPLC Method B was used to determine the purity of Compound (I). Samples of Compound (I) were analyzed for purity using High Performance Liquid Chromatography (HPLC) with a UV detector, using a Waters Symmetry C8, 5 μm, 100 Å particles, column (150 mm×3.9 mm). A gradient of triethylamine/acetic acid buffer solution (A) and acetonitrile (B) was used, at a flow rate of 1.1 mL/min (0-8.8 min linear gradient 80-60% A, 8.8-11.8 60% A, 11.8-17.6 min linear gradient 60-40% A, 17.6-21.8 min linear gradient 40-15% A, 21.8-24.7 min, 15% A, 24.7-25.9 linear gradient 15-80% A, 25.9-30, 80% A). The triethylamine/acetic acid buffer solution (A) was prepared by adding triethylamine (5.0 mL) and acetic acid (3.0 mL) to distilled water (5 L). The solution was mixed well, and the pH adjusted to 5.3 via addition of triethylamine to raise the pH or acetic acid to lower the pH. An injection volume of 36 μL was used, UV detection was set to collect at a wavelength of 275 nm, autosampler was at 5° C., and the column temperature was set at 50° C.

Samples for HPLC analysis by Method B were prepared by dissolving a sample of Compound (I) in a diluent prepared by mixing Triethylamine/Acetic Acid Buffer Solution (A) (1600 mL) with acetonitrile (400 mL) at a concentration of approximately 25 μg/mL.

Compound (I) level is determined by calculating weight percent of Compound (I) in the sample of the Compound (I). Individual impurity levels are determined by calculating weight percent of each impurity in the sample of the Compound (I). Compound (I) is hygroscopic. Care should be taken to minimize exposure to environmental moisture. The weight of the sample is corrected to exclude moisture content in the sample of Compound (I) according to the following formula:

$$\text{corrected sample amount} = \text{sample amount} \times \frac{100 - \% \text{ Water}}{100}$$

corrected sample amount=moisture corrected sample amount in milligrams
sample amount=sample amount in milligrams prior to moisture correction
% Water=moisture content of sample as determined by Karl Fischer titration The relative order of elution of select impurities relative to Compound (I) are as follows in order of earlier eluting to later eluting peaks:
  a) 4,4'-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}azanediyl)dibutanoic acid;
  b) Compound (i);
  c) 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoic acid;
  d) 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione;
  e) 4-[{(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}(hydroxy)amino]butanoic acid;
  f) Compound (xii);
  g) 5-(2-fluoro-3-methoxyphenyl)-1-{[2-fluoro-6-(trifluoromethyl)phenyl]methyl}-6-methyl-3-[(2R)-2-(2-oxopyrrolidin-1-yl)-2-phenylethyl]pyrimidine-2,4(1H,3H)-dione;

h) 5-(2-fluoro-3-methoxyphenyl)-1-{[2-fluoro-6-(trifluoromethyl)phenyl]methyl}-6-methyl-3-(2-oxo-2-phenylethyl)pyrimidine-2,4(1H,3H)-dione; and
i) ethyl 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate.

4-[{(1R)-2-[5-(2-Fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}(hydroxy)amino]butanoic acid may elute as two peaks or two slightly resolved peaks due to atropisomerism. If there are two resolved, separately integrated peaks, the sum the peak areas is used for determining the weight percent of the impurity.

LC-MS Method C

LC-MS Method C was used to determine the amount of (2R)-2-[(tert-butoxycarbonyl)amino]-2-phenylethyl methanesulfonate impurity ("sulfonate impurity") on a weight basis in Compound (II). Samples of Compound (II) were analyzed for purity using High performance liquid chromatography (HPLC) with UV detector and Mass Spectrometer (Agilent model #6130) or equivalent. The HPLC column was a Waters X-Bridge Shield RP18, 3.5 µm column (150 mm×4.6 mm) or equivalent. A gradient of 0.1% ammonium hydroxide in water (A) and 0.1% ammonium hydroxide in acetonitrile (B) was used, at a flow rate of 1.2 mL/min (0-15.0 min linear gradient 80-50% A, 15.0-17.0 min 50% A, 17.0-19.0 min linear gradient 50-0% A, 19.0-25.0 min 0% A, 25.0-25.1 min, linear gradient 0-80% A, 25.1-30 min 80% A). An injection volume of 10 µL was used, UV detection was set to collect at a wavelength of 210 nm, autosampler was at set at 4° C., and the column temperature was set at 25° C. Mass spectrometry used ESI ionization mode with positive polarity, 3000 V or appropriate capillary voltage, SIM scan event type, 260.0 SIM ion, 1:1 or as appropriate post column split ratio, 6.0 L/min drying gas flow, 40 psig nebulizer pressure, 350° C. drying gas temperature, 70 V fragmentor, 1.00 or as appropriate Gain, 0.59 second or as appropriate dwell time. Mass data collected between 12.5-17.5 minutes or as appropriate.

Samples for LC-MS analysis by Method C are prepared by dissolving a sample of Compound (II) in a diluent of N,N-dimethyl formamide at a concentration of approximately 33 mg/mL. A standard sample of the sulfonate impurity at a known concentration of approximately 0.1 µg/mL in a diluent of N,N-dimethyl formamide is prepared. The sulfonate impurity level in ppm relative to Compound (IIa), the free base of Compound (II), in the analyzed sample is calculated according to the following formula:

$$\text{sulfonate impurity } (ppm) = \frac{A_{Samp}}{A_{Stand}} \times \frac{C_{Stand}}{C_{Samp}} \times P \times \frac{1}{SF}$$

$A_{Samp}$=Peak area of sulfonate impurity in sample
$A_{Stand}$=Peak area of sulfonate impurity in standard
$C_{Stand}$=Concentration of standard in µg/mL
$C_{Samp}$=Concentration of sample in g/mL
P=Purity of sulfonate impurity standard. For example if sulfonate impurity standard is 98.2%, then P is 0.982
SF=Salt Factor is 0.80 (100× Molecular weight of Compound (IIa)/Molecular weight of Compound (II))

LC-MS Method D

LC-MS Method D was used to determine the amount of Compounds (xv, xvi, and xvii) in Compound (I). Samples of Compound (I) were analyzed for purity using High performance liquid chromatography (HPLC) with mass spectrometry detection after chemical derivatization. The HPLC column was a Supelco Ascentis Express HILIC, silica particles, 2.7 µm column (150 mm×4.6 mm) or equivalent. An isocratic system of 0.1% formic acid (v/v) in acetonitrile (A) and 20 mM ammonium formate in water and 0.1% formic acid (v/v) (B) was used, at a flow rate of 1 mL/min (0-25 min 87% A, 13% B). An injection volume of 50 µL was used, and the column temperature was set at 35° C. Mass spectrometry used positive electrospray ionization mode with selected ion monitoring at 116.0 m/z, 88.0 m/z, and 102.0 m/z.

Samples for LC-MS analysis by Method D are prepared at a concentration of about 15 mg/mL. The samples are brought to about 90% volume with acetonitrile, derivatized by adding 10% of a triethylamine solution relative to the final volume (triethylamine solution: 4.5% (v/v) triethylamine in water), and heating at 60° C. for at least two hours. Solutions should return to ambient temperature prior to analysis.

GC-MS Method E

GC-MS Method E was used to determine the amount of Compound (xviii) in Compound (I). Samples of Compound (I) were analyzed for purity using gas chromatography (GC) with mass spectrometry electron ionization detection. The GC column was a 5% diphenyl-95% dimethyl polysiloxane, 1 µm film (30 mm×0.32 mm ID). The carrier gas was helium at a flow rate of approximately 1.5 mL/min. An oven program (50° C., 0 min; 10° C./min to 100° C.; hold 100° C. for 1 min; 30° C./min to 250° C., hold 250° C. for 5 min) was used. A split inlet mode was used with a split ratio of 5:1, an inlet temperature of 220° C., and injection volume of 1 with detection using an electron ionization mass spectrometer. Mass spectrometry used a positive electron impact ionization mode with a transfer line temperature of 280° C., source temperature of 230° C., and quad temperature of 150° C. with selected ion monitoring at 74 and 88 m/z.

Samples for GC-MS analysis by Method E are prepared by combining with mixing about 260 mg of Compound (I), 5.0 mL of water and 3.0 mL of hexanes. After layer separation, the hexane layer is transferred to a 10 mL volumetric flask. The procedure is repeated twice more with hexanes. The three hexanes layers are combined in the 10 mL volumetric flask and diluted to volume with hexanes.

GC-MS Method F

GC-MS Method F was used to determine the amount of Compound (x) in Compound (I). Samples of Compound (I) were analyzed for purity using gas chromatography (GC) with mass spectrometry electron ionization detection. Samples of Compound (I) were analyzed for purity using gas chromatography (GC) with mass spectrometry electron ionization detection. The GC column was a 5% diphenyl-95% dimethyl polysiloxane, 1 µm film (30 mm×0.32 mm ID). The carrier gas was helium at a flow rate of approximately 1.5 mL/min. An oven program (50° C., 0-2 min; 10° C./min to 90° C.; hold 100° C. for 2 min; 30° C./min to 250° C., hold 250° C. for 5 min) was used. A split inlet mode was used with split ratio of 15:1, an inlet temperature of 220° C., and injection volume of 1 µL, with detection using an electron ionization mass spectrometer. Mass spectrometry used a positive electron impact ionization mode with a transfer line temperature of 280° C., source temperature of 230° C., and quad temperature of 150° C. with selected ion monitoring at 31, 43, 72, 87, and 114 m/z. Samples for GC-MS analysis by Method F are prepared at a concentration of about 0.05 g of Compound (I) in N-methyl-2-pyrrolidone.

HPLC Method G

HPLC Method G was used to determine the amount of Compound (ix) in Compound (I). Samples of Compound (I) were analyzed using High Performance Liquid Chromatography (HPLC) with a UV detector, using a Phenomenex Chirex 3011, (S)-tert-leucine and 3,5-dinitroaniline, 5 μm, column (250 mm 4.6 mm). An isocratic system using the mobile phase comprising Ammonium Acetate Buffer Solution (50 mM ammonium acetate in distilled water, pH 7.5), acetonitrile, and methanol in a 10:20:70 (v/v) ratio, at a flow rate of 1 mL/min, was used. An injection volume of 50 μL was used, UV detection was set to collect at a wavelength of 275 nm, and the column temperature was set at 25° C.

Samples for HPLC analysis by Method G were prepared by dissolving a sample of Compound (I) in the mobile phase at a concentration of approximately 500 μg/mL. The weight percent of compound (ix) is determined relative to the sum of weight of Compound (ix) and Compound (I).

The Examples and reactions are described using smaller-scale gram quantities of materials. The compounds, however, may be scaled-up in kilogram quantities for commercial production. To illustrate, thus for Example 1, wherein the reactor is charged with 520 mL, one of skilled in the art may use 520 L for commercial production; and therefore the resulting title compound would be 132.6 kilograms.

Example 1

N-{[2-fluoro-6-(trifluoromethyl)phenyl]methyl}urea

To a reactor is charged tetrahydrofuran (520 mL) followed by 3-fluorobenzotrifluoride (130.0 g) and diisopropylamine (20.8 g). The mixture is cooled to −76° C., then n-butyllithium (2.5 M in hexanes, 215.8 g) is added, keeping the temperature below −70° C. After stirring the mixture for 1 hour, N,N-dimethylformamide (63.7 g) is added, keeping the temperature below −70° C. After an hour, a mixture of tetrahydrofuran (130 mL) and acetic acid (152 mL) is added, keeping the temperature below −50° C. The temperature is increased to −20° C., and water (520 mL) is added, then the temperature is increased to 20° C. A combination of water (130 mL) and hydroxylamine hydrochloride (66.3 g) is added and stirred for 2 hours. Sodium chloride (162.5 g) is added to the mixture which is stirred for 30 minutes at 30° C. The bottom layer is separated and discarded. To the organic layer is added zinc powder (130.0 g), and then the mixture is warmed to 55° C. To the suspension is added concentrated hydrochloric acid (330 mL). After 2 hours, the mixture is cooled to 30° C. and filtered. Water (65 mL) is used to rinse the filter. The lower aqueous product layer is separated and urea (427.7 g) is added. Ammonia (306 mL) is added, and the reaction temperature is raised to 95° C., distilling volatiles to a separate container. After 3 hours at 95° C., concentrated hydrochloric acid (462 mL) is added keeping the temperature less than 100° C. Another charge of concentrated hydrochloric acid (250 mL) is done to lower the pH to <2. Acetic acid (260 mL) is added at 95° C., then the mixture is cooled to 20° C. and the solids are isolated by filtration. The initial cake is suspended in a combination of water (341 g) and concentrated hydrochloric acid (36 mL), and is then isolated again by filtration, and is washed with water (520 mL). The material is dried at 50° C. using hot air, which affords the title compound (132.6 g). The title compound has the following characteristic data: $^1$H NMR (400 MHz, DMSO-$d_6$) δ 7.64-7.52 (m, 3H), 6.17 (t, J=5.2 Hz, 1H), 5.48 (s, 2H), 4.36 (dt, J=5.3, 1.4 Hz, 2H).

Example 2

1-{[2-fluoro-6-(trifluoromethyl)phenyl]methyl}-6-methylpyrimidine-2,4(1H,3H)-dione 1-{[2-fluoro-6-(trifluoromethyl)phenyl]methyl}-6-methylpyrimidine-2,4(1H,3H)-dione may be prepared as described in U.S. Pat. No. 8,765,948.

Example 3

1-{[2-fluoro-6-(trifluoromethyl)phenyl]methyl}-5-iodo-6-methylpyrimidine-2,4(1H,3H)-dione 1-{[2-fluoro-6-(trifluoromethyl)phenyl]methyl}-5-iodo-6-methylpyrimidine-2,4(1H,3H)-dione may be prepared as described in U.S. Pat. No. 8,765,948.

Example 4

5-(2-fluoro-3-methoxyphenyl)-1-{[2-fluoro-6-(trifluoromethyl)phenyl]methyl}-6-methylpyrimidine-2,4(1H,3H)-dione Example 3 (60.1 g), 4-(di-tert-butylphosphanyl)-N,N-dimethylaniline ligand (0.23 g), palladium acetate (0.095 g) and (2-fluoro-3-methoxyphenyl)boronic acid (35.7 g) were charged to a reactor and degassed with nitrogen to <20 ppm oxygen. A separate flask was charged with potassium hydroxide (36.7 g), water (241 g) and dioxane (258 g) and degassed with nitrogen to <20 ppm oxygen. The solution was transferred into the solids in the reactor, and the mixture was warmed to 60° C. for 6 hours, then cooled to ambient temperature. The reaction mixture was filtered through diatomaceous earth, and the filtrate was added over 18 hours to a separate flask charged with N-acetyl cysteine (3.43 g), dioxane (172.5 g), acetic acid (92.5 g) and water (58.4 g), then warmed to 75° C. The product slurry was cooled to ambient over 2 hours and filtered. The cake was washed with 3/2 water/methanol, then pure methanol, then dried under vacuum at 60° C., to afford the title compound (51.3 g). $^1$H NMR (400 MHz, DMSO-$d_6$) δ ppm 11.55 (s, 1H), 7.64 (dt, J=7.5, 3.3 Hz, 1H), 7.61-7.50 (m, 2H), 7.20-7.08 (m, 2H), 6.72 (ddd, J=6.2, 5.5, 3.2 Hz, 1H), 5.33 (d, J=3.5 Hz, 2H), 3.85 (s, 3H), 2.05 (s, 3H).

Example 5

(2R)-2-[(tert-butoxycarbonyl)amino]-2-phenylethyl methanesulfonate

To a reactor was charged boc-phenylglycinol (5.9 g), N,N-dimethylformamide (11.3 mL), and triethylamine (4.2 mL). The mixture was cooled to <5° C., and methanesulfonyl chloride (1.94 mL) was added over 90 min. Acetone (17.8 mL) was charged followed by water (28.4 mL) over 3 hours, keeping temperature <5° C. The mixture was filtered and washed with water/acetone mixture (2/1, water/acetone, 31.7 mL). The cake was dried under vacuum at 35° C. to afford the title compound (6.30 g). $^1$H NMR (400 MHz, CDCl$_3$) δ ppm 7.43-7.27 (m, 5H), 5.22 (d, J=8.0 Hz, 1H), 5.01 (s, 1H), 4.46 (dd, J=10.2, 4.6 Hz, 1H), 4.40 (dd, J=10.4, 6.0 Hz, 1H), 2.88 (s, 3H), 1.44 (s, 9H).

Example 6

3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione may be prepared starting from Example 4 and Example 5 following the procedure described in U.S. Pat. No. 8,765,948.

Example 7A salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione (1/1)

To Example 6 (40.0 g) was added methanol (120 mL), and then the reaction mixture warmed to 50° C. To a separate vessel was charged salicylic acid (10.6 g) and methanol (40 mL), and then the mixture warmed to 50° C. About 25% of the Example 6/methanol mixture was added to the salicylic acid mixture, and then the mixture was seeded with 2-hydroxybenzoic acid-3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione (1/1). The addition was continued over approximately 1.5 hour, and a thick slurry formed after 10 min. After the addition was completed, the mixture was allowed to cool to 20° C. The slurry was filtered and the cake washed with methanol (2×50 mL). The cake dried at 50° C. under vacuum overnight, to afford the title compound (47.5 g).

Example 7B salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione (1/1)

To a reactor was charged Example 4 (20.6 g), Example 5 (38.4 g), N,N-dimethylformamide (38.5 g), and then 1,1,3,3-tetramethylguanidine (19.1 g). The mixture was warmed to 40-45° C. When the reaction was complete, ammonia (17.8 g, 28% grade) was added, and the temperature was increased to 65° C. After the Example 5 was consumed, iso-propyl acetate (162 g) was added, and the mixture was extracted with 17% aqueous $H_3PO_4$ solution 3 times (1×163 g, 1×115 g, and then 1×93.5 g). To the resulting organic layer was added water (6.3 g) and methanesulfonic acid (14.0 g) and then the mixture was heated to 60° C. After reaction completion, the reaction mixture was extracted with 14% aqueous $K_3PO_4$ solution (2×220 g), until pH>9. The solvent was removed by distillation. Methanol was added until the volume was approximately 190 mL. After warming to 55° C., water (16.7 g) was added, followed by a solution of salicylic acid (7.1 g) in methanol (17.3 g). The mixture was seeded, then cooled to 10° C. Water (73 g) was added. The product was isolated by filtration. The cake was washed with a mixture of methanol/water (65/35, w/w), then dried at 80° C. to produce the title compound (30.4 g). $^1$H NMR (400 MHz, DMSO-$d_6$) δ ppm 8.62 (s, 3H), 7.71-7.62 (m, 2H), 7.62-7.47 (m, 2H), 7.44-7.35 (m, 5H), 7.21-7.09 (m, 3H), 6.83 (td, J=6.1, 3.1 Hz, 0.5H), 6.70-6.57 (m, 2H), 5.37 (dd, J=17.0, 9.7 Hz, 1H), 5.17 (dd, J=17.0, 12.5 Hz, 1H), 4.63 (ddd, J=12.7, 8.4, 5.7 Hz, 1H), 4.38-4.06 (m, 2H), 3.84 (s, 3H), 1.94 (d, J=2.6 Hz, 3H).

Example 8 sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate A mixture of Example 7B (20.7 g), methyl tert-butyl ether (98.9 g), iso-propyl acetate (49.7 g) and a 5% aqueous NaOH solution (56.9 g) was heated to 50° C. The resulting organic layer was concentrated via distillation, and N,N-dimethylacetamide (38.2 g) was added. To the N,N-dimethylacetamide solution was added N,N-diisopropylethylamine (4.5 g) and ethyl 4-bromobutyrate (11.7 g). The mixture was heated at 60° C. for 4 hours. After the temperature was lowered to 20° C., methyl tert-butyl ether (88.7 g) and water (107.8 g) were added. The organic layer was separated and 6% aqueous $H_3PO_4$ solution (106.5 g) was added. The aqueous layer was separated, and then extracted with methyl tert-butyl ether (2×90 g). The resulting aqueous layer was neutralized by addition of methyl isobutyl ketone (96.7 g) and a 33% aqueous $K_3PO_4$ solution (66.8 g) at 40° C., and the organic layer was separated. To the resulting organic layer was added a 13.5% aqueous sodium hydroxide solution (18.4 g) and ethanol (72.1 g). After the hydrolysis was complete, the volatiles were distilled, and replaced with water to make the volume approximately 165 mL. The aqueous layer was extracted with methyl isobutyl ketone (2×69 g) at 40° C. The resulting aqueous layer was then mixed with sodium chloride (27.1 g) and methyl isobutyl ketone (101 g) at 40° C. After mixing thoroughly, the organic layer was separated, and then extracted with 16% aqueous sodium chloride (3×64 g) at 40° C. The organic layer was concentrated via distillation, and then filtered. The title compound was isolated by addition of the methyl isobutyl ketone solution (15.4 g methyl isobutyl ketone) to heptane (28.1 g) at −5° C. The product was filtered, washed with heptane and dried under vacuum at 70° C., to afford the title compound (2.7 g). The purity was determined to be 99.9% by HPLC Method B.

Polymorph Forms

Example 9

Polymorphic Form A

Polymorphic Form A is the freebase anhydrate form of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione.

Powder X-ray diffraction (PXRD) pattern of Polymorphic Form A is shown in FIG. 1. Characteristic PXRD peaks include those listed in Table 1:

TABLE 1

| Characteristic Peak Listing of Polymorphic Form A Peak Position (° 2θ) |
|---|
| 8.0 |
| 11.5 |
| 12.0 |
| 12.5 |
| 13.5 |

TABLE 1-continued

Characteristic Peak Listing of Polymorphic Form A
Peak Position (° 2θ)

| |
|---|
| 15.4 |
| 16.8 |
| 17.3 |
| 18.7 |
| 20.0 |

The crystal structure of Form A was solved using direct methods in Bruker's APEX2 Crystallography Software Suite, and refinement with SHELXL. Crystallographic information is shown in Table 2.

TABLE 2

Crystallographic information of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione, Form A

| | |
|---|---|
| Crystal Form | Anhydrate |
| Lattice Type | Monoclinic |
| Space Group | $P2_1$ |
| Cell Length a (Å) | 9.38 |
| Cell Length b (Å) | 13.04 |
| Cell Length c (Å) | 20.45 |
| Cell Angle α (°) | 90 |
| Cell Angle β (°) | 94.7 |
| Cell Angle γ (°) | 90 |
| Cell Volume (Å³) | 2494.2 |
| R-Factor (%) | 10.1 |

Example 10

Polymorphic Form B

Example 6 (12.9 g) was placed in methanol (85 mL), warmed to 55° C. and water (8.0 g) was added. In a separate vessel, salicylic acid (3.4 g) was dissolved in methanol (10.7 mL) and warmed to 55° C. The mixture of salicylic acid in methanol was added to the Example 6 solution maintaining temperature at 55° C. Seed crystals (0.08 g) were added (Example 6 basis compared to Example 6 in solution). The mixture was held for 1 hour at 55° C., cooled to 10° C., and held at 10° C. for 2 hours. Water (13.0 g) was added to the slurry over 2 hours to generate an overall 65/35 w/w ratio of methanol to water, and then the slurry was held overnight. The solids were filtered at 10° C., washed with 65/35 w/w ratio of methanol to water, and air-dried at ambient conditions to afford polymorphic Form B, the Solvate Hydrate Form (mono-methanol/hemi-hydrate) of the salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione.

Powder X-ray diffraction (PXRD) pattern of Polymorphic Form B is shown in FIG. 2. Characteristic PXRD peaks include those listed in Table 3.

TABLE 3

Characteristic Peak Listing of Polymorphic Form B
Peak Position (° 2θ)

| |
|---|
| 6.0 |
| 8.1 |
| 8.7 |
| 9.5 |
| 9.8 |
| 10.6 |

TABLE 3-continued

Characteristic Peak Listing of Polymorphic Form B
Peak Position (° 2θ)

| |
|---|
| 12.2 |
| 12.5 |
| 13.1 |
| 14.5 |

The crystal structure of Form B was solved using direct methods in Bruker's APEX2 Crystallography Software Suite, and refinement with SHELXL. Crystallographic information is shown in Table 4. 0.5H₂O molecules and 1.0 methanol molecules per molecule Compound (II) exist in the crystal structure.

TABLE 4

Crystallographic information of Compound (II), Form B

| | |
|---|---|
| Crystal Form | Mono-methanol/hemi-hydrate |
| Lattice Type | Triclinic |
| Space Group | P1 |
| Cell Length a (Å) | 10.25 |
| Cell Length b (Å) | 10.99 |
| Cell Length c (Å) | 14.87 |
| Cell Angle α (°) | 96.7 |
| Cell Angle β (°) | 97.1 |
| Cell Angle γ (°) | 91.8 |
| Cell Volume (Å³) | 1650.1 |
| R-Factor (%) | 6.8 |

Example 11

Polymorphic Form C

Example 6 (15.0 g) was placed in methanol (57.0 g), then warmed to 55° C. Salicylic acid (4.18 g) was added to the mixture and the temperature maintained at 55° C. Seed crystals were added at 0.5% w/w (Example 6 basis compared to Example 6 in solution). The mixture was held at 55° C., then cooled to ambient temperature. The solids were filtered, washed with methanol, and air-dried at ambient temperature to afford polymorphic Form C, the Methanol Solvate of the salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4(1H,3H)-dione.

Seed crystals of Form C can be prepared using the above procedure without the seeding step. Alternatively, Form C, including suitable seed crystals of Form C can be prepared from Form B. A slurry of Form B (100 mg) in methanol (2 mL) was stirred for at least 4 days at 40° C. or alternatively at least 5 days at 25° C. The solids were filtered, washed with methanol (2 mL), and then air-dried at 25° C. to afford polymorphic Form C.

Powder X-ray diffraction (PXRD) pattern of Polymorphic Form C is shown in FIG. 3. Characteristic PXRD peaks include those listed in Table 5. A representative thermo gravimetric analysis (TGA) scan is shown in FIG. 6. A representative differential scanning calorimetry (DSC) scan is shown in FIG. 7. Sample powders were encapsulated in an aluminum pinhole pan, and a heating rate of 10° C./minute was used to heat the sample from 25 to 300° C. The DSC scan of Form C shows an endotherm (peak) at 128.3° C. The TGA scan shows a weight loss from methanol between about 25-150° C.

TABLE 5

Characteristic Peak Listing of Polymorphic Form C
Peak Position (° 2θ)

| |
|---|
| 7.0 |
| 9.6 |
| 10.7 |
| 10.9 |
| 11.4 |
| 13.1 |
| 13.5 |
| 17.3 |
| 17.5 |
| 18.2 |

The crystal structure of Form C was solved using direct methods in Bruker's APEX2 Crystallography Software Suite, and refinement with SHELXL. Crystallographic information is shown in Table 6. 1.0 Methanol molecules per molecule Compound (II) exist in the crystal structure.

TABLE 6

Crystallographic information of Compound (II), Form C

| | |
|---|---|
| Crystal Form | Methanol solvate |
| Lattice Type | Orthorhombic |
| Space Group | $P2_12_12_1$ |
| Cell Length a (Å) | 11.13 |
| Cell Length b (Å) | 16.84 |
| Cell Length c (Å) | 18.14 |
| Cell Angle α (°) | 90 |
| Cell Angle β (°) | 90 |
| Cell Angle γ (°) | 90 |
| Cell Volume (Å$^3$) | 3399.4 |
| R-Factor (%) | 8.7 |

Example 12

Polymorphic Form D

Example 10 was placed inside a dynamic vapor sorption (DVS) instrument (DVS Advantage, Surface Measurement Systems Ltd, Alperton, United Kingdom). Approximately 5-25 mg were loaded on a pan. The percent relative humidity (% RH) was modified according to the following method: % RH was stepped from 30 to 90% RH, and then stepped from 90 to 0% RH. The % RH was then stepped again to 90% RH, and finally stepped back to 0% RH. Each % RH step was in 10% increment. The criteria for proceeding to the next RH condition was dm/dt=0.002 (%/min) where m is the mass of the sample, with a maximum time of 360 minutes. At the end of the experiment, polymorphic Form D, the desolvated/ dehydrated form of the salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4 (1H,3H)-dione was isolated.

Powder X-ray diffraction (PXRD) pattern of Polymorphic Form D is shown in FIG. 4. Characteristic PXRD peaks include those shown in Table 7.

TABLE 7

Characteristic Peak Listing of Polymorphic Form D
Peak Position (° 2θ)

| |
|---|
| 6.1 |
| 8.1 |
| 8.7 |
| 10.2 |

TABLE 7-continued

Characteristic Peak Listing of Polymorphic Form D
Peak Position (° 2θ)

| |
|---|
| 10.4 |
| 12.0 |
| 13.1 |
| 14.4 |
| 16.6 |
| 17.4 |

Example 13

Polymorphic Form E

A mixture of Example 10 (50 mg) in 50:50 (v/v) ethyl acetate/heptanes (1.0 mL) was stirred at ambient temperature for two weeks. The solids were isolated by vacuum filtration and allowed to air-dry overnight at ambient conditions to afford the polymorphic Form E, the ethyl acetate solvate form of the salicylate salt of 3-[(2R)-2-amino-2-phenylethyl]-5-(2-fluoro-3-methoxyphenyl)-1-{[2-fluoro-6-(trifluoromethyl)phenyl]methyl}-6-methylpyrimidine-2,4 (1H,3H)-dione was isolated.

Figure 8:
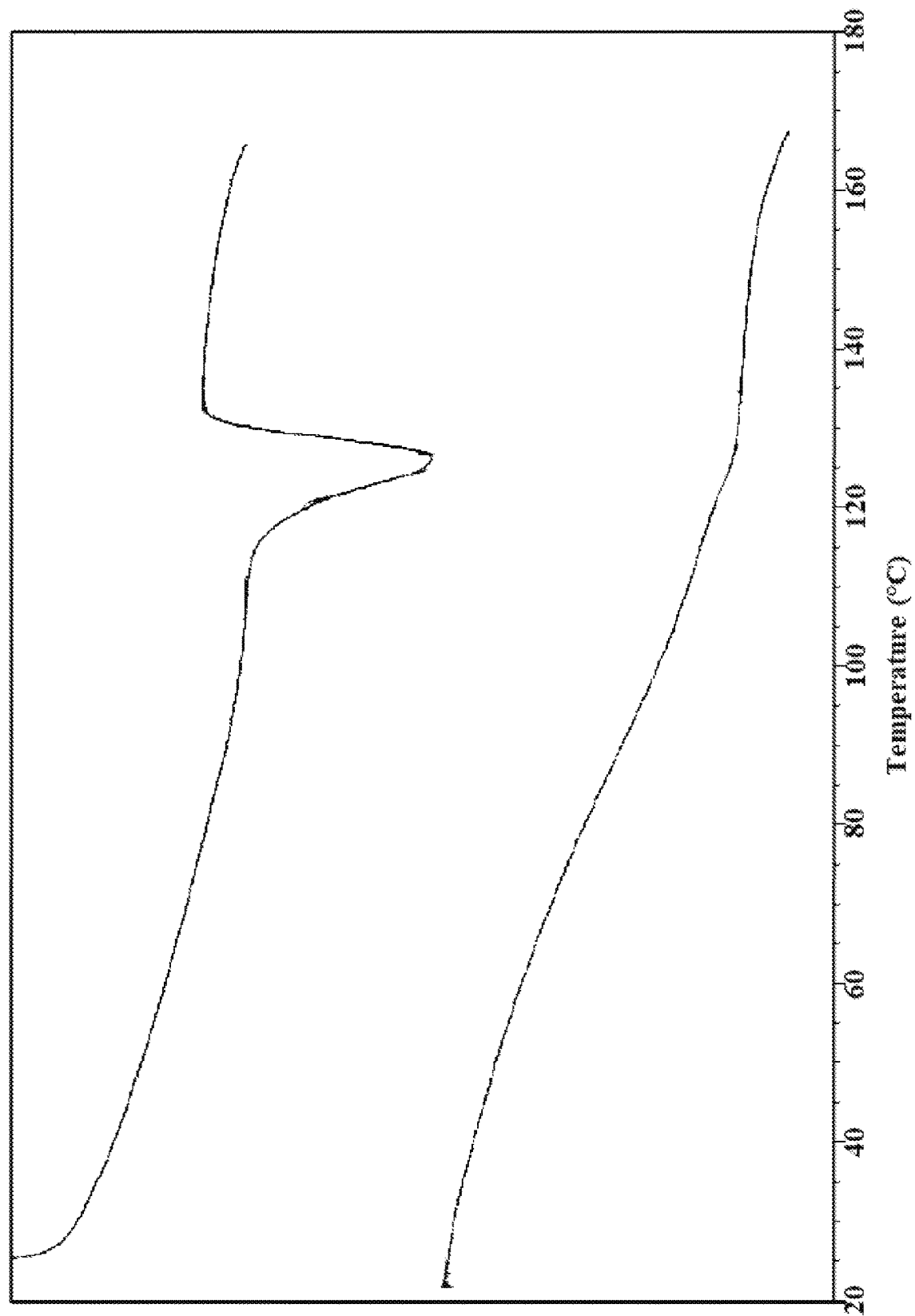
FIG. 8 is a TGA/DSC thermogram of Form E.

Powder X-ray diffraction (PXRD) pattern of Polymorphic Form E is shown in FIG. 5. Characteristic PXRD peaks include those shown in Table 8. A representative TGA/DSC scan is shown in FIG. 8. The DSC scan of Form E shows an endotherm (peak) at 126.7° C. TGA-IR confirms a 4.3% weight loss from ethyl acetate between about 25-130° C.

TABLE 8

Characteristic Peak Listing of Polymorphic Form E
Peak Position (° 2θ)

| |
|---|
| 5.9 |
| 8.0 |
| 8.5 |
| 10.1 |
| 10.6 |
| 11.9 |
| 13.1 |
| 13.6 |
| 16.0 |
| 17.2 |

Example 14 sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate The concentration of a solution comprising Compound (I) and methyl isobutyl ketone, (final concentrated organic layer from Example 8 which is prior to being added to heptane and after concentration to remove water and filtration), is adjusted to 17.2% of Compound (I) by weight. The concentration-adjusted Compound (I)/methyl isobutyl ketone solution (5.8 g) is added to a reactor containing heptane (7.8 g) at 10° C., while the reactor contents are agitated. The precipitated product is filtered and washed with heptane (8.1 g) followed by drying at 65° C. in an agitated filter dryer. The dried product is delumped and physical properties are measured. The final product has the following properties: specific surface area of 10.4 m$^2$/g, flow function coefficient (ff$_c$) of 1.8, and volume-averaged particle size Dv10 of 9 μm.

Example 15 sodium 4-({(1R)-2-[5-(2-fluoro-3-methoxyphenyl)-
3-{[2-fluoro-6-(trifluoromethyl)phenyl]methyl}-4-
methyl-2,6-dioxo-3,6-dihydropyrimidin-1(2H)-yl]-1-
phenylethyl}amino)butanoate The concentration of a solution comprising Compound (I) and methyl isobutyl ketone, (final concentrated organic layer from Example 8 which is prior to being added to heptane and after concentration to remove water and filtration), is adjusted to 17.5% of Compound (I) by weight. A stream of this concentration-adjusted Compound (I)/methyl isobutyl ketone solution (95.3 g/s) is continuously mixed with heptane (127.3 g/s) to induce precipitation of the product, and this step is executed for 1 min. The precipitated product is filtered and washed with heptane (10 L) followed by drying at 60° C. in an agitated filter dryer. The dried product is delumped and physical properties are measured. The final product has the following properties: specific surface area of 49.0 m$^2$/g, flow function coefficient (ff$_c$) of 2.8, and volume-averaged particle size Dv10 of 17 μm.

Example 16 sodium 4-({(1R)-2-[5-(2-fluoro-3-methoxyphenyl)-
3-{[2-fluoro-6-(trifluoromethyl)phenyl]methyl}-4-
methyl-2,6-dioxo-3,6-dihydropyrimidin-1(2H)-yl]-1-
phenylethyl}amino)butanoate The concentration of a solution comprising Compound (I) and methyl isobutyl ketone, (final concentrated organic layer from Example 8 which is prior to being added to heptane and after concentration to remove water and filtration), is adjusted to 17.6% of Compound (I) by weight. A stream of this concentration-adjusted Compound (I)/methyl isobutyl ketone solution (32.5 g/s) is continuously mixed with heptane (43.3 g/s) to induce precipitation of the product, and this step is executed for 3 min. The precipitated product is filtered and washed with heptane (10 L) followed by drying at 65° C. in an agitated filter dryer. The dried product is subjected to humidification (97% relative humidity) at ambient temperature for 18 hours. The humidified product is further dried at 80° C. and then delumped. The specific surface area of the final product is reduced to 0.3 m$^2$/g.

Example 17 sodium 4-({(1R)-2-[5-(2-fluoro-3-methoxyphenyl)-
3-{[2-fluoro-6-(trifluoromethyl)phenyl]methyl}-4-
methyl-2,6-dioxo-3,6-dihydropyrimidin-1(2H)-yl]-1-
phenylethyl}amino)butanoate The concentration of a solution comprising Compound (I) and methyl isobutyl ketone, (final concentrated organic layer from Example 8 which is prior to being added to heptane and after concentration to remove water and filtration), is adjusted to 18.4% of Compound (I) by weight. A stream of this concentration-adjusted Compound (I)/methyl isobutyl ketone solution (89.7 g/s) is continuously mixed with heptane (119.7 g/s) to induce precipitation of the product, and this step is executed for 1 min. The precipitated product is filtered and washed with heptane (10 L) followed by drying at 70° C. in an agitated filter dryer. The dried product is milled under aggressive conditions and physical properties are measured. The final product has the following properties: specific surface area of 35.3 m$^2$/g, bulk density of 0.17 g/mL, flow function coefficient (ff$_c$) of 1.2, and volume-averaged particle size Dv10 of 6

Example 18 sodium 4-({(1R)-2-[5-(2-fluoro-3-methoxyphenyl)-
3-{[2-fluoro-6-(trifluoromethyl)phenyl]methyl}-4-
methyl-2,6-dioxo-3,6-dihydropyrimidin-1(2H)-yl]-1-
phenylethyl}amino)butanoate The concentration of a solution comprising Compound (I) and methyl isobutyl ketone, (final concentrated organic layer from Example 8 which is prior to being added to heptane and after concentration to remove water and filtration), is adjusted to 17.5% of Compound (I) by weight. A stream of this concentration-adjusted Compound (I)/methyl isobutyl ketone solution (95.3 g/s) is continuously mixed with heptane (127.3 g/s) to induce precipitation of the product, and this step is executed for 1 min. The precipitated product is filtered, and then washed with heptane (10 L), while continuously agitating the solvent-wet product cake in an agitated filter dryer. The product is dried at 65° C., delumped and physical properties are measured. The final product has the following properties: specific surface area of 32.2 m$^2$/g, bulk density of 0.33 g/mL, flow function coefficient (ff$_c$) of 6.8, and volume-averaged particle size Dv10 of 204 μm.

Example 19 ethyl 4-{[(1R)-2-hydroxy-1-phenylethyl]
amino}butanoate

Phenylglycinol (1.0 eq.) is charged to a reactor followed by N,N,-diisopropylethylamine (1.05 eq.), and the mixture is heated to 85° C. To the solution is charged ethyl 4-bromobutanoate (1.15 eq.), and the mixture is heated at 85° C. for 45 minutes. The reaction mixture is allowed to cool to 45-55° C., and ethyl acetate (5 volumes) is added. The resulting slurry is filtered, and the filtrate washed with 30% phosphoric acid until a pH of 5.3-5.5. The layers are separated, and to the aqueous layer is charged dichloromethane (2-5 L/kg), followed by addition of 10% aqueous sodium carbonate until the pH is 9-10. The aqueous layer is extracted dichloromethane (2×2-5 L/kg). The dichloromethane layers are combined and used in Example 20. Alternatively, the combined dichloromethane layers may be concentrated and purified via chromatography (silica gel column, gradient: 1:1 to 0:1 heptanes/ethyl acetate, rf 0.2 in 4:1 ethyl acetate/heptanes) to afford the title compound in high yield. $^1$H NMR (400 MHz, CDCl$_3$) δ 7.38-7.22 (m, 5H), 4.17-4.01 (m, 2H), 3.77-3.64 (m, 2H), 3.56-3.46 (m, 1H), 2.66-2.45 (m, 3H), 2.35 (td, J=7.3, 2.8 Hz, 2H), 1.87-1.74 (m, 2H), 1.29-1.16 (m, 3H). $^{13}$C NMR (101 MHz, CDCl$_3$) δ 173.50, 140.15, 128.47, 127.49, 127.13, 66.43, 64.54, 60.22, 46.40, 32.02, 25.06, 14.05.

Example 20 ethyl 4-[(4R)-2-oxo-4-phenyl-1,2λ$^4$,3-oxathiazolidin-3-yl]butanoate

The combined dichloromethane layers from Example 19 are cooled to 25-35° C. Dichloromethane is added to reach a concentration of 8 L/kg, and the resulting mixture further cooled to −5° C. 4-(Dimethylamino)pyridine (0.2 eq.) and N,N,-diisopropylethylamine (3.0 eq.) or alternatively pyridine (3.0 eq.) is charged to the reaction mixture. A solution of thionyl chloride in dichloromethane (2 L/kg) is slowly added to the Example 19 reaction mixture over 3 hours, maintaining the temperature −5 to 0° C. A solution of 1M aqueous HCl (2-4 L/kg of Example 19) is added slowly, maintaining the temperature between 0-15° C. After addition is complete, the reaction mixture is allowed to warm to ambient temperature. The organic layer is separated and washed with a 5-10% solution of sodium bicarbonate until the pH of the aqueous layer is 8. The organic layer (approximately a 1:1 mixture of diastereomers) is used in Example 21. Alternatively, the mixture may be purified (silica gel column, isocratic 3:1 heptanes/ethyl acetate, rf: 0.3) to afford the title compound in high yield. $^1$H NMR (400 MHz, CDCl$_3$) δ 7.67-7.29 (m, 10H), 4.98 (t, J=7.8 Hz, 1H), 4.77 (dd, J=9.0, 7.2 Hz, 1H), 4.73-4.54 (m, 1H), 4.49 (dd, J=9.9, 7.1 Hz, 1H), 4.18 (t, J=8.4 Hz, 1H), 4.12-3.93 (m, 4H), 3.18-2.94 (m, 4H), 2.73 (dt, J=13.1, 8.0 Hz, 1H), 2.29 (ddt, J=20.1, 16.2, 8.0 Hz, 4H), 2.03-1.83 (m, 2H), 1.76 (dp, J=14.0, 7.1 Hz, 2H), 1.20 (td, J=7.1, 4.9 Hz, 6H). $^{13}$C NMR (101 MHz, CDCl$_3$) δ 172.72, 172.58, 135.96, 135.32, 129.12, 129.03, 128.92, 128.72, 128.14, 127.84, 78.15, 76.23, 67.23, 63.02, 60.42, 60.40, 44.29, 43.54, 31.60, 31.11, 23.94, 23.62, 14.13, 14.12.

Example 21 ethyl 4-[(4R)-2,2-dioxo-4-phenyl-1,2λ$^6$,3-oxathiazolidin-3-yl]butanoate

The solution from Example 20 is added to a solution of dichloromethane:water (1:1, 6-8 L/kg Example 20), ruthenium trichloride (0.25 mol %) and sodium hypochlorite (10% solution in water, 1.3-1.5 mole equivalents) dropwise at 23° C. with vigorous mixing of the two layers. The resulting mixture is stirred for approximately 1 hour at ambient temperature. The reaction workup is performed using option 1, 2, or 3. Option 1: The solution is filtered through a pad of diatomaceous earth and the layers are separated. Isopropyl alcohol (0.5 equivalents) is then charged to the organic layer and the solution is stirred for 1 hour, concentrated via distillation, and solvent exchanged to acetonitrile to afford a 0.5 M solution. Option 2: Isopropyl alcohol is added until two phases are visible, and the solution is stirred for 1 hour. The organic layer is separated, concentrated via distillation, and solvent exchanged to acetonitrile to afford a 0.5 M solution. Option 3: To the emulsion of the organic and aqueous layer is added a 1M HCl solution until two layers are visible, and the layers are separated. To the organic layer is added 5% aqueous sodium bicarbonate until pH 8 is reached and the layers were separated. The organic layer is concentrated via distillation, and solvent exchanged to acetonitrile to afford a 0.5 M solution. The 0.5 M solution in acetonitrile may be concentrated and purified via chromatography (silica gel column, isocratic 4:1 heptanes/ethyl acetate, rf: 0.3). The title compound is obtained in high yield. $^1$H NMR (400 MHz, CDCl$_3$) δ 7.26 (s, 5H), 4.59-4.49 (m, 1H), 4.44 (dd, J=8.7, 6.8 Hz, 1H), 4.28-4.11 (m, 1H), 3.94-3.70 (m, 2H), 3.01 (ddd, J=13.5, 7.3, 5.1 Hz, 1H), 2.77 (dt, J=13.4, 7.9 Hz, 1H), 2.27-2.02 (m, 2H), 1.93-1.56 (m, 2H), 1.05-0.97 (t, 3H). $^{13}$C NMR (101 MHz, CDCl$_3$) δ 172.49, 134.69, 129.81, 129.41, 127.60, 72.63, 64.50, 60.41, 45.56, 30.92, 22.44, 14.11.

Example 22 ethyl 4-[(4R)-2,2-dioxo-4-phenyl-1,2λ$^6$,3-oxathiazolidin-3-yl]butanoate

To a solution of Example 19 was added N,N,-diisopropylethylamine (2.5 equivalents) and dichloromethane (2-4 L/kg Example 19). The resulting mixture was cooled to −78° C., and sulfuryl chloride (1.2 eq.) was added dropwise. After reaction completion, the reaction mixture was washed with 1N HCl and warmed to ambient temperature. The organic layer was washed with 5-10% aqueous NaHCO$_3$, and the aqueous layer extracted with dichloromethane. The combined organic layers were concentrated, and purified (silica gel column, isocratic 4:1 hexanes/ethyl acetate) to yield the title compound.

Example 23

(4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid-N,N,N',N'-tetramethylguanidine (1/1)

To Example 21 (1.1 equivalents) in acetonitrile (forming a 0.5-1 M solution) was added 5-(2-fluoro-3-methoxyphenyl)-1-{[2-fluoro-6-(trifluoromethyl)phenyl]methyl}-6-methylpyrimidine-2,4(1H,3H)-dione (1.0 eq., U.S. Pat. No. 8,765,948, step 1C), followed by addition of tetramethylguanidine (1.5 eq.) dropwise. The mixture was heated at about 60° C. for 1 hour, then cooled to ambient temperature, and crystallized by solvent exchange with 2-methyltetrahydrofuran. The cake was washed with 2-methyltetrahydrofuran (1-2 L/kg of Example 21) to afford the title compound in 93% yield. $^1$H NMR (400 MHz, CDCl$_3$) δ 8.00 (s, 2H), 7.51 (ddd, J=8.2, 6.4, 2.9 Hz, 3H), 7.37 (td, J=8.1, 4.9 Hz, 1H), 7.28-7.14 (m, 4H), 7.03 (td, J=8.0, 1.2 Hz, 1H), 6.93 (ddd, J=8.2, 5.1, 1.9 Hz, 1H), 6.82 (dtd, J=7.7, 5.9, 1.6 Hz, 1H), 5.65-5.42 (m, 2H), 5.26 (d, J=17.4 Hz, 1H), 4.71 (dd, J=13.0, 8.6 Hz, 1H), 4.56 (td, J=13.1, 7.5 Hz, 1H), 3.97 (tdd, J=7.9, 6.7, 2.6 Hz, 2H), 3.87 (dd, J=2.3, 0.8 Hz, 3H), 3.20-3.05 (m, 1H), 3.05-2.90 (m, 1H), 2.87 (d, J=0.8 Hz, 11H), 2.08-1.88 (m, 3H), 1.97 (s, 3H), 1.74 (dd, J=12.7, 6.3 Hz, 1H), 1.44-1.38 (m, 1H), 1.15 (tt, J=7.1, 1.1 Hz, 3H). $^{13}$C NMR (101 MHz, CDCl$_3$) δ 173.91, 162.45, 159.96, 151.95, 149.67, 147.82, 139.09, 129.51, 128.98, 127.81, 124.85, 123.69, 121.06, 120.99, 112.91, 108.09, 107.91, 77.20, 75.15, 67.65, 59.77, 57.03, 56.73, 44.65, 42.88, 42.15, 41.92, 39.56, 33.01, 32.03, 25.83, 20.89, 17.71, 14.10.

Example 24 sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate To Example 23 in 1:1 (v/v) acetonitrile/water (3-8 L/kg Example 23) is added 4.0 equivalents of aqueous 3 M NaOH. The reaction is stirred for 2 hours at ambient temperature. 3 M HCl is added until the pH is approximately 0-2, and the resulting mixture is stirred for an additional hour or until reaction completion. To the resulting mixture is added 10% aqueous sodium bicarbonate until pH 8 is reached, and then the mixture concentrated to remove acetonitrile. The resulting aqueous layer was washed with methyl tert-butyl ether (2×3-8 L/kg Example 23) were performed. Methyl isobutyl ketone (3-8 L/kg Example 23) was added to the aqueous layer, and sodium chloride (10-20 w/w %) was added. The mixture was stirred and the layers separated. To the organic layer was added an equal volume of n-heptanes, and the resulting mixture was concentrated to afford a solid in high yield.

Example 24b sodium 4-({(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}amino)butanoate To Example 23 in 1:1 (v/v) acetonitrile/water (3-8 L/kg Example 23) is added aqueous 3 M HCl until the pH is about 0-2. The reaction is stirred for 1-16 hours at ambient temperature. Aqueous 10% sodium bicarbonate is added until the pH is approximately 8, or alternatively, aqueous 4 M NaOH (3 equivalents) is added until the pH is approximately 10 after 1-2 h from the addition of acid. The resulting mixture is stirred for an additional 1-3 hours or until reaction completion, and then the mixture concentrated to remove acetonitrile. The resulting aqueous layer was washed with methyl tert-butyl ether (2×3-8 L/kg Example 23) were performed. Methyl isobutyl ketone (3-8 L/kg Example 23) was added to the aqueous layer, and sodium chloride (10-20 w/w %) was added. The mixture stirred, and the layers separated. To the organic layer was added an equal volume of n-heptanes, and the resulting mixture was concentrated to afford a solid in high yield.

Example 25

Polymorphic Form F

The reaction mixture from Example 23 is diluted with 2-methyltetrahydrofuran in a volume equal to that of acetonitrile, and the solution concentrated in vacuo. The concentrate is reconstituted in 2-methyltetrahydrofuran in a volume equal to that used initially. The mixture is stirred at ambient temperature for not less than 6 hours. The resulting precipitate is collected, washed with 2-methyltetrahydrofuran and dried on the filter under vacuum for 5 minutes to afford Polymorphic Form F as a hydrate. A KF of 2-4% is observed.

Powder X-ray diffraction (PXRD) pattern of Polymorphic Form F is shown in FIG. 17. Characteristic PXRD peaks include those listed in Table 11. A representative TGA/DSC scan is shown in FIG. 11.

TABLE 11

| Characteristic Peak Listing of Polymorphic Form F Peak Position (° 2θ) |
| --- |
| 6.0 |
| 7.6 |
| 8.9 |
| 9.6 |
| 10.7 |
| 12.4 |
| 14.8 |
| 15.3 |
| 16.6 |
| 17.5 |
| 18.2 |

Example 26

Polymorphic Form G

Polymorphic Form G is prepared by drying Polymorphic Form F. Polymorphic Form F was dried at 60° C. for not less than 16 hours in a vacuum oven to afford a nonhydrate form of (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid—N,N,N',N'-tetramethylguanidine (1/1). As used herein, nonhydrate refers to a water-free polymorphic form.

Powder X-ray diffraction (PXRD) pattern of Polymorphic Form G is shown in FIG. 15. Characteristic PXRD peaks include those listed in Table 9: A representative TGA/DSC scan is shown in FIG. 9.

TABLE 9

| Characteristic Peak Listing of Polymorphic Form G Peak Position (° 2θ) |
| --- |
| 6.1 |
| 7.7 |
| 8.9 |
| 9.6 |
| 10.7 |
| 12.3 |
| 14.7 |
| 15.3 |
| 16.6 |
| 17.5 |
| 18.2 |

Example 27

Polymorphic Form H (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid-N,N,N',N'-tetramethylguanidine (1/1)

(4-Ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid-N,N,N',N'-tetramethylguanidine (1/1) (50 mg) was suspended in 25/75% (w/w) acetonitrile/2-methyltetrahydrofuran (200 μL) or alternatively in dichloromethane (100 μL) and subjected to thermocycling (25-50° C. linear gradient 10° C./hour, 50° C. 4 hours, 50-5° C. linear gradient −20° C./hour, 5° C. 4 hours, 5-50° C. linear gradient 10° C./hour, 50° C. 4 hours, 50-5° C. linear gradient −10° C./hour, 5° C. 4 hours, 5-50° C. linear gradient 10° C./hour, 50° C. 4 hours, 50-5° C. linear gradient −5° C./hour, 5° C. 4 hours, 5-25° C. linear gradient 10° C./hour, 25° C. 72 hours). The solids were separated and dried under vacuum (5 mbar, 50° C.) to afford Polymorphic Form H as a nonhydrate.

Figure 10:
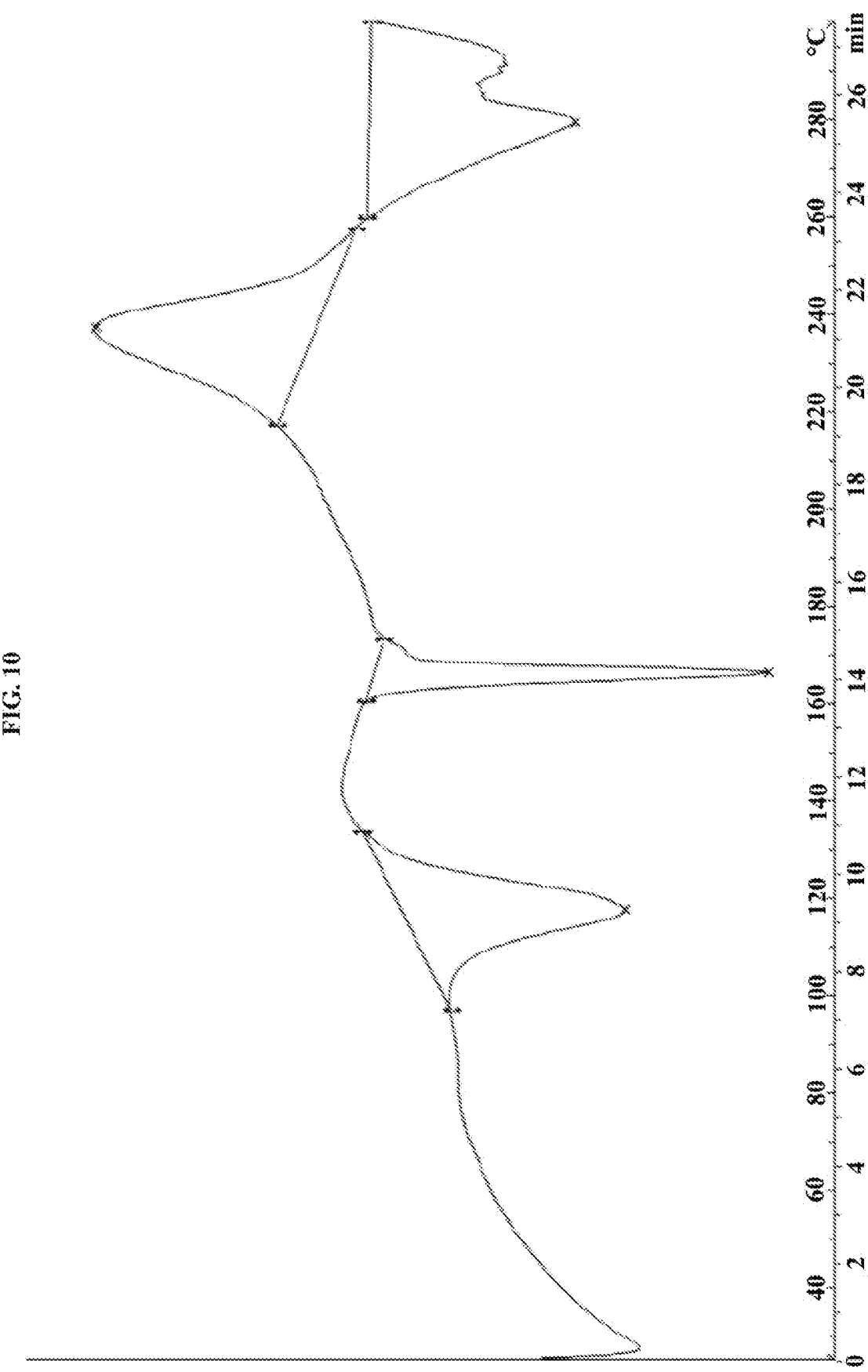
FIG. 10 is a DSC thermogram of Form H.
Figure 20:
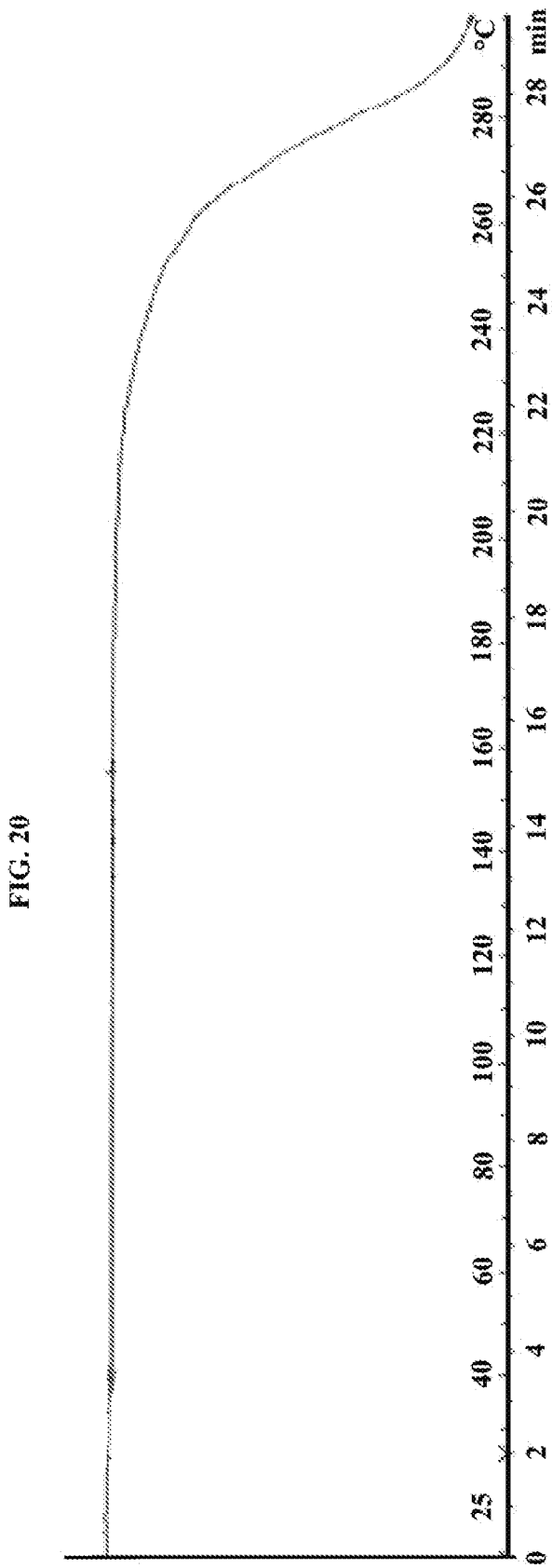
FIG. 20 is a TGA thermogram of Form H.

A representative TGA scan of Form H is shown in FIG. 20. A representative DSC scan of Form H is shown in FIG. 10.

Powder X-ray diffraction (PXRD) pattern of Polymorphic Form H is shown in FIG. 16. Characteristic PXRD peaks include those listed in Table 10.

TABLE 10

| Characteristic Peak Listing of Polymorphic Form H Peak Position (° 2θ) |
| --- |
| 5.9 |
| 6.7 |
| 8.5 |
| 9.3 |

TABLE 10-continued

Characteristic Peak Listing of Polymorphic Form H
Peak Position (° 2θ)

10.7
11.1
15.3
16.0
17.4
17.8

Example 28

Polymorphic Form I

Form I was prepared by suspending 50 mg of (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid-N,N,N',N'-tetramethylguanidine (1/1) in dimethyl sulfoxide (100 μL) and subjected to thermocycling (25-50° C. linear gradient 10° C./hour, 50° C. 4 hours, 50-5° C. linear gradient −20° C./hour, 5° C. 4 hours, 5-50° C. linear gradient 10° C./hour, 50° C. 4 hours, 50-5° C. linear gradient −10° C./hour, 5° C. 4 hours, 5-50° C. linear gradient 10° C./hour, 50° C. 4 hours, 50-5° C. linear gradient −5° C./hour, 5° C. 4 hours, 5-25° C. linear gradient 10° C./hour, 25° C. 72 hours). The solvent was allowed to evaporate at ambient temperature and then under vacuum, to afford Polymorphic Form I as a dimethyl sulfoxide monosolvate.

Figure 12:
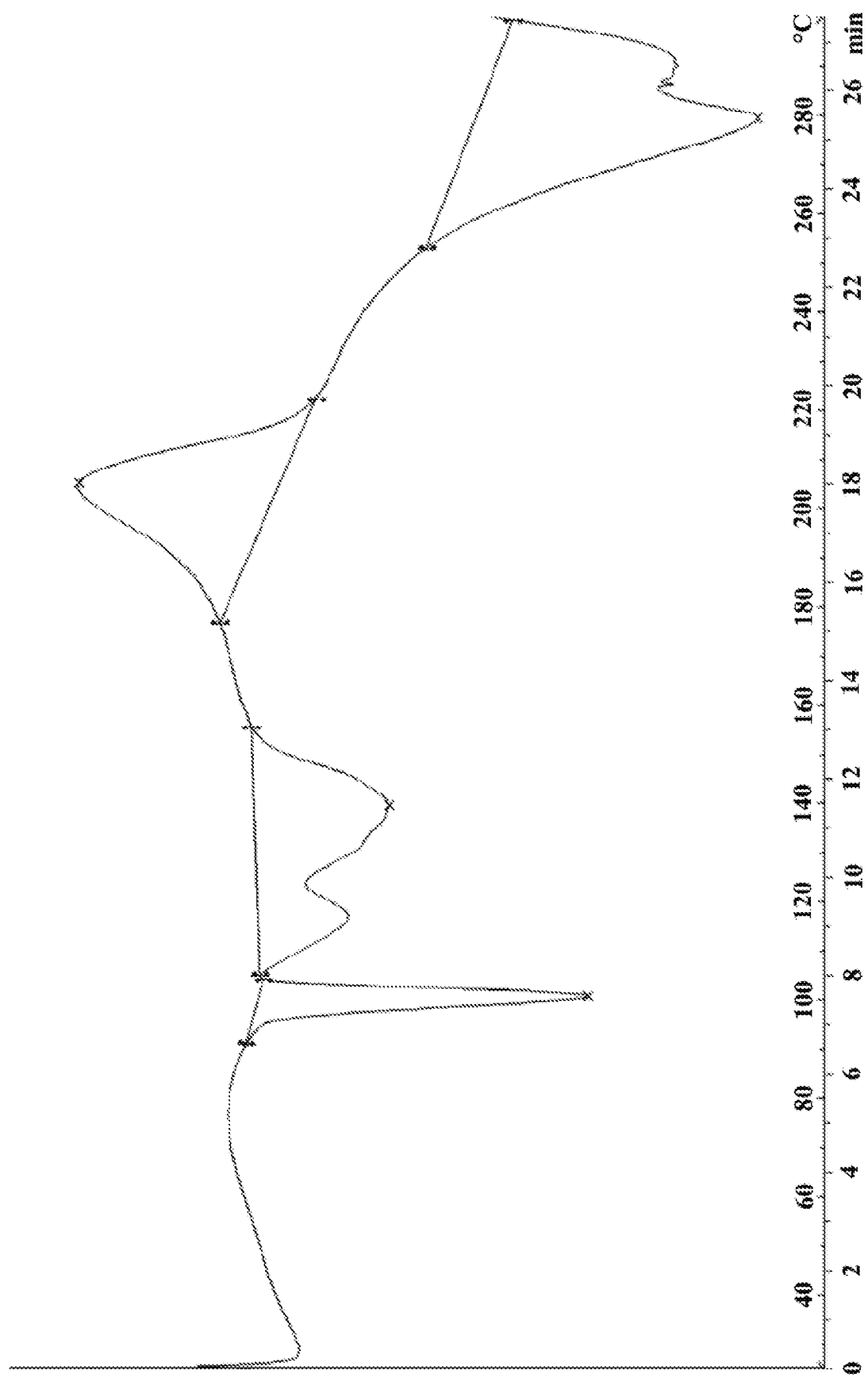
FIG. 12 is a DSC thermogram of Form I.
Figure 13:
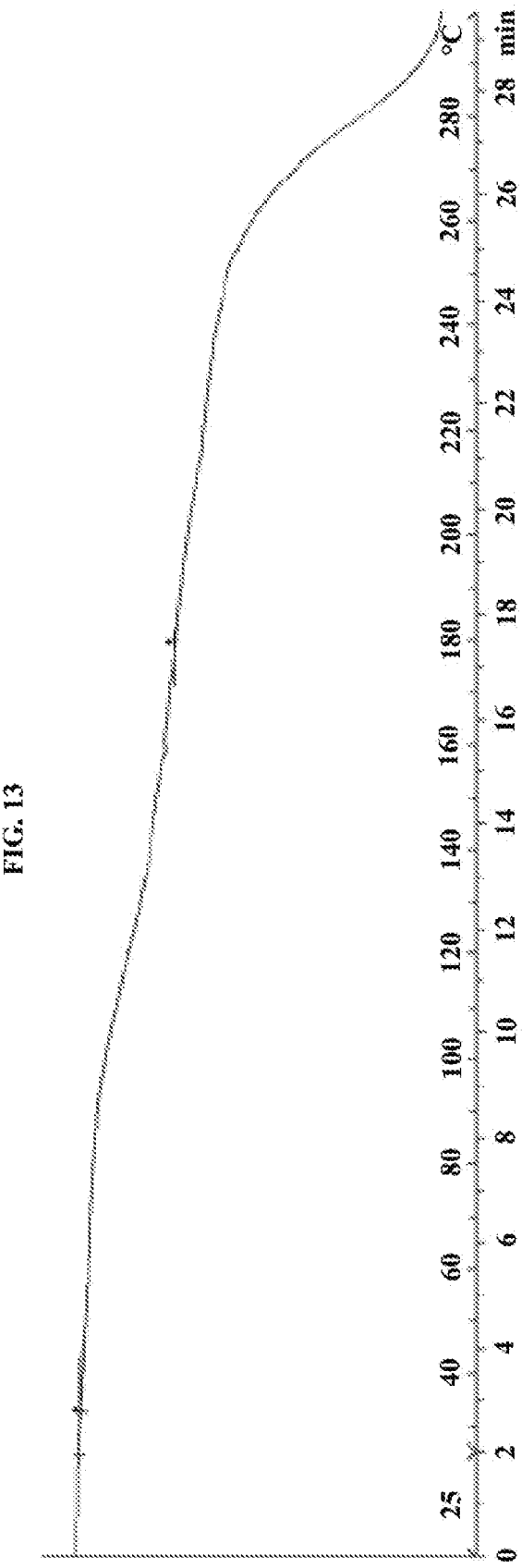
FIG. 13 is a TGA thermogram of Form I.

A representative TGA scan of Form I is shown in FIG. 13. A mass loss of 8.8% between about 40 and 180° C. is observed, which corresponds to approximately one equivalent of dimethyl sulfoxide. A representative DSC scan is shown in FIG. 12. Powder X-ray diffraction (PXRD) pattern of Polymorphic Form I is shown in FIG. 18. Characteristic PXRD peaks include those listed in Table 12.

TABLE 12

Characteristic Peak Listing of Polymorphic Form I
Peak Position (° 2θ)

5.8
7.3
10.6
12.1
14.6
15.0
17.0
17.5
18.6
22.9

Example 29

Polymorphic Form J

Dichloromethane (500 μL) was added to a 2 dram vial containing (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl}sulfamic acid-N,N,N',N'-tetramethylguanidine (1/1) (15 mg). To a scintillation vial was added hexanes (500 The 2 dram vial was placed within the scintillation vial. The scintillation vial was sealed and held at ambient temperature overnight. The resulting crystals were separated and afforded Polymorphic Form J as a dichloromethane monosolvate.

A representative TGA/DSC scan of Form J is shown in FIG. 14. A mass loss between about 40 and 170° C. is observed in the TGA which corresponds to approximately one equivalent of dichloromethane. Powder X-ray diffraction (PXRD) pattern of Polymorphic Form J is shown in FIG. 19. Characteristic PXRD peaks include those listed in Table 13.

TABLE 13

Characteristic Peak Listing of Polymorphic Form J
Peak Position (° 2θ)

5.9
6.6
8.4
10.6
11.7
12.3
14.8
15.9
17.6
18.9

The crystal structure of Form J was solved using intrinsic phasing in Bruker's APEX3 Crystallography Software Suite. Refinement was achieved with SHELXL. Crystallographic information is shown in Table 14.

TABLE 14

Crystallographic information of (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1(2H)-yl]-1-phenylethyl} sulfamic acid-N,N,N',N'-tetramethylguanidine (1/1), Form J

| | |
|---|---|
| Crystal Form | Dichloromethane monosolvate |
| Lattice Type | monoclinic |
| Space Group | $P2_1$ |
| Cell Length a (Å) | 9.9 |
| Cell Length b (Å) | 14.8 |
| Cell Length c (Å) | 29.7 |
| Cell Angle α (°) | 90.0 |
| Cell Angle β (°) | 90.3 |
| Cell Angle γ (°) | 90.0 |
| Cell Volume (Å³) | 4344.6 |
| R-Factor (%) | 5.4 |

It is understood that the foregoing detailed description and accompanying examples are merely illustrative and are not to be taken as limitations upon the scope of the present disclosure. Further benefits, changes, and modifications to the described embodiments will be apparent to those skilled in the art from reading this patent application. Such changes and modifications, including without limitation those relating to the chemical structures, substituents, derivatives, intermediates, syntheses, formulations, or methods, or any combination of such changes and modifications of use of the present disclosure, may be made without departing from the spirit and scope thereof

We claim:

1. A composition comprising: Compound (I),

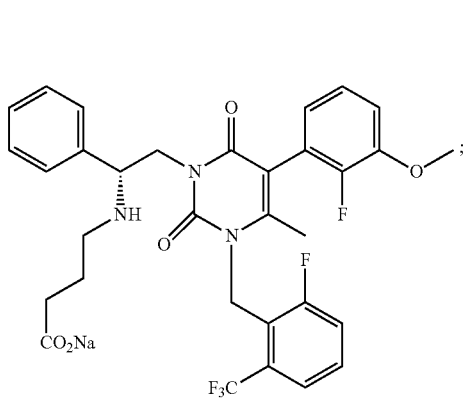
(I)

and one or more impurity selected from a group consisting of:

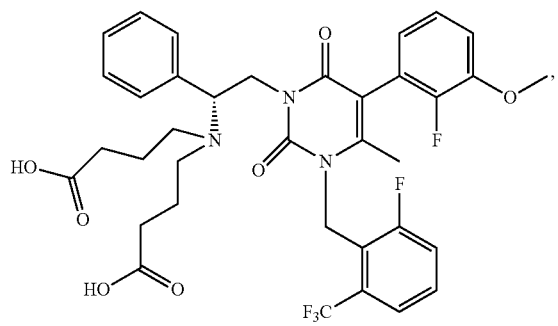
(iii)

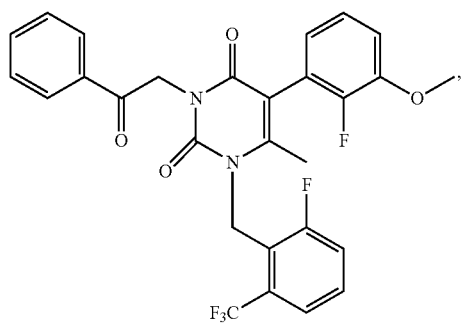
(v)

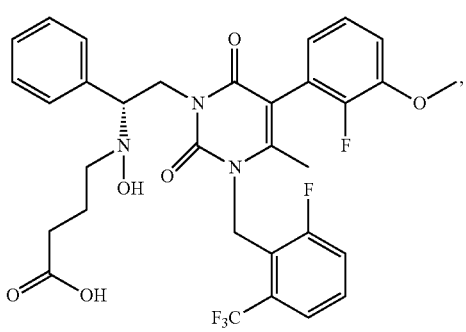
(vi)

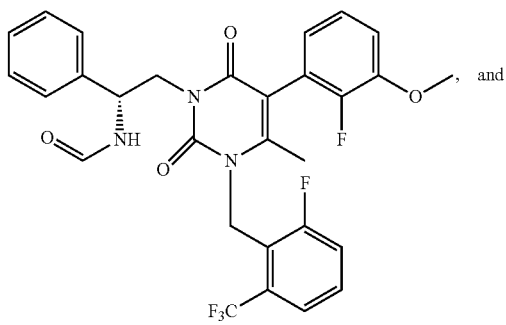
(vii)

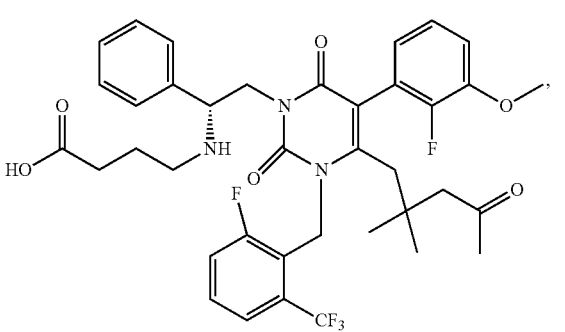
(viii)

wherein Compound (I) comprises at least 97 weight percent of the composition and wherein the one or more impurity is present in an amount that is greater than zero and equal to or less than 3 weight percent of the composition.

2. The composition of claim 1, wherein the composition further comprises one or more additional impurities, wherein the one or more additional impurities are selected from the group consisting of:

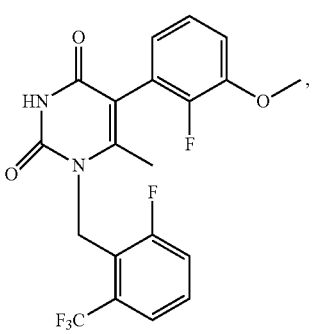
(i)

(IIa)
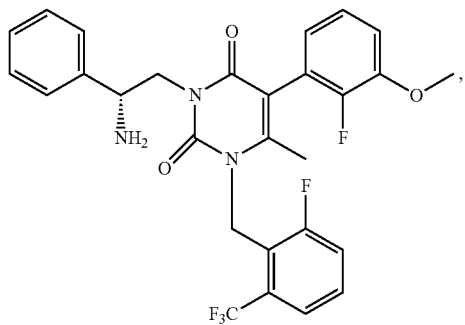

(ii)
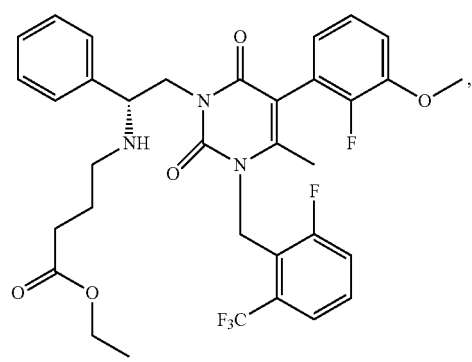

(iv)
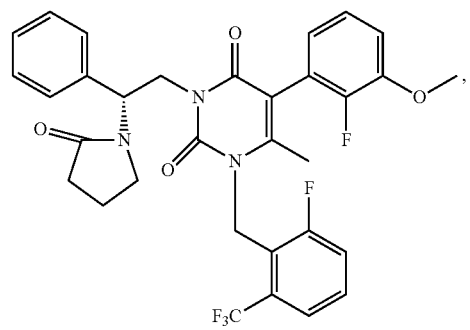

(x)
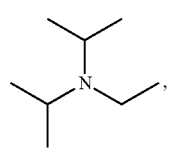

(xv)
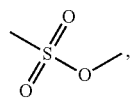

(xvi)
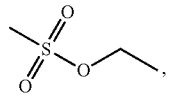

(xvii)
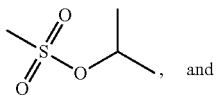, and (xviii)
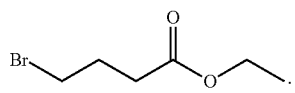

3. The composition of claim 1, wherein Compound (I) is substantially amorphous.

4. The composition of claim 1, wherein the composition comprises at least 98 weight percent Compound (I) and wherein the one or more impurity is present in an amount that is greater than zero and equal to or less than 2 weight percent of the composition.

5. A composition comprising,

Compound (I), (I)
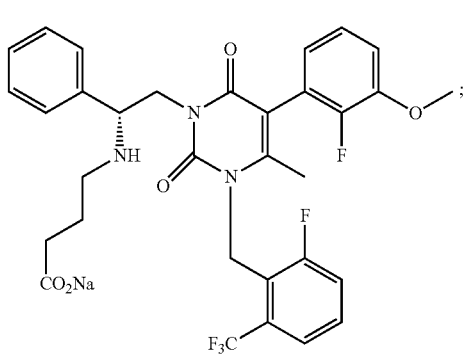

and one or more impurity selected from a group consisting of:

(iii)
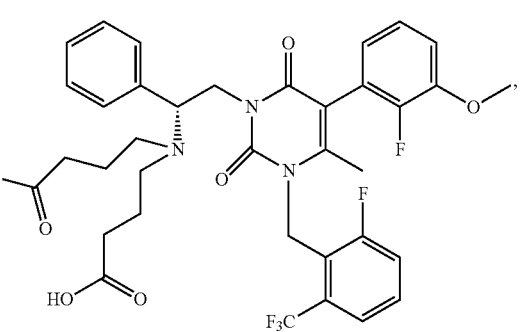

(v)
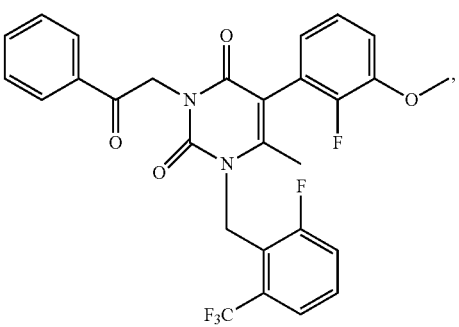

-continued (vi)
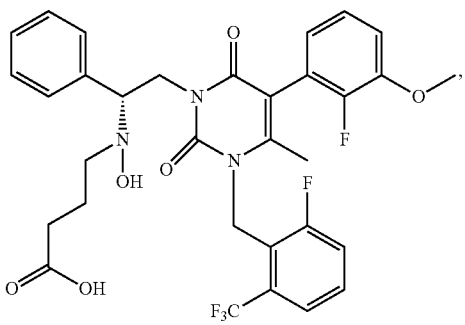

(vii)
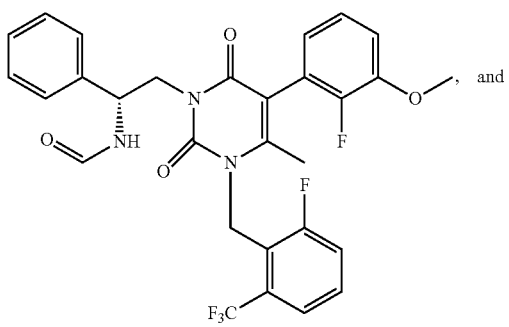
, and (viii)
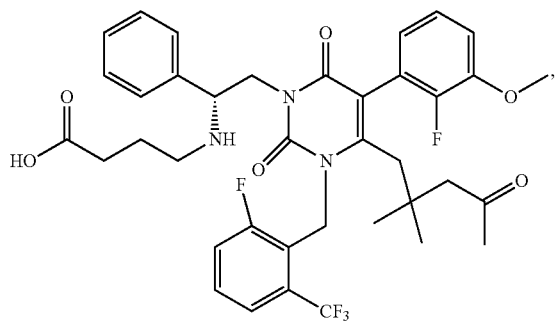

wherein the composition comprises at least about 97 weight percent of Compound (I), and wherein the one or more impurity is present in an amount that is greater than zero and equal to or less than 3 weight percent of the composition, and further wherein the composition is prepared by a process comprising, using as an intermediate, Compound (II), (II)
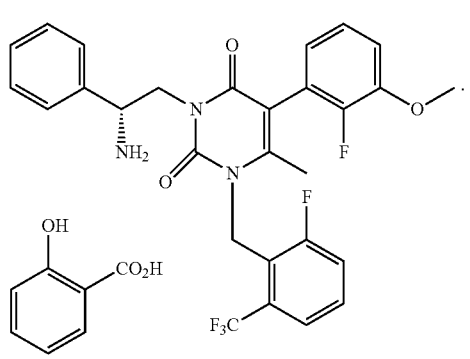

6. The composition of claim 5, wherein the process further comprises reacting Compound (IIa), (IIa)
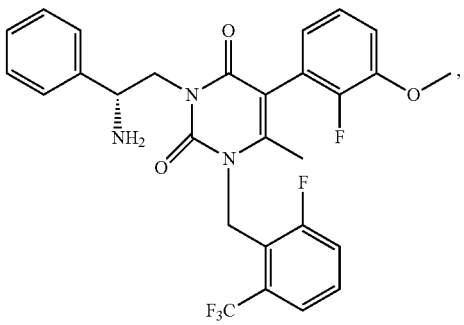

with salicylic acid to form Compound (II).

7. The composition of claim 6, wherein the process further comprises isolating Compound (II) to provide an isolated Compound (II).

8. The composition of claim 5, wherein the composition further comprises one or more additional impurities, wherein the one or more additional impurities are selected from the group consisting of:

(i)
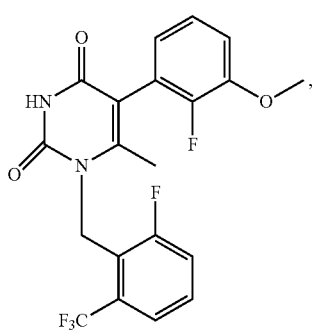

(IIa)
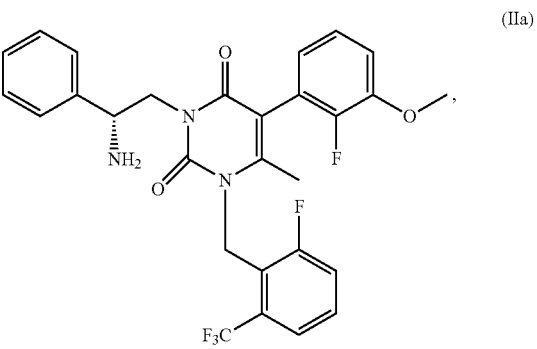

-continued (ii)
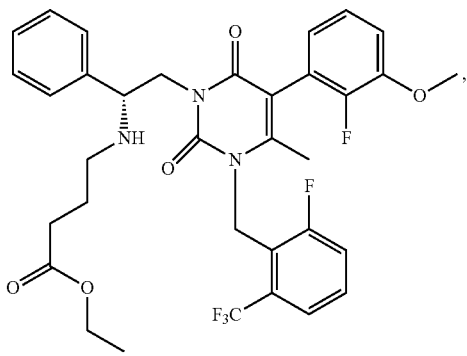

(iv)
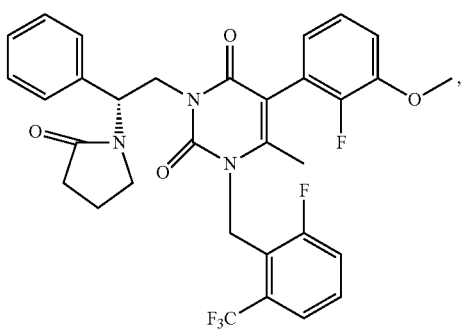

(x)
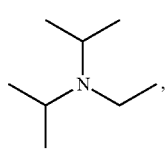

(xv)
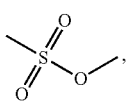

(xvi)
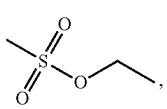

(xvii)
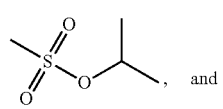, and (xviii)
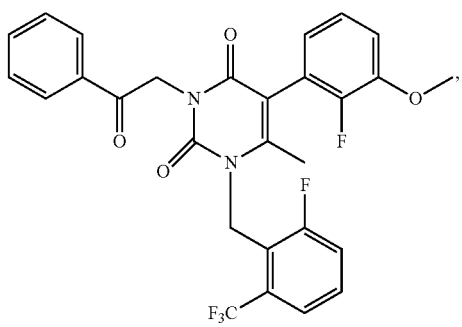

9. A composition comprising:
Compound (I)

(I)
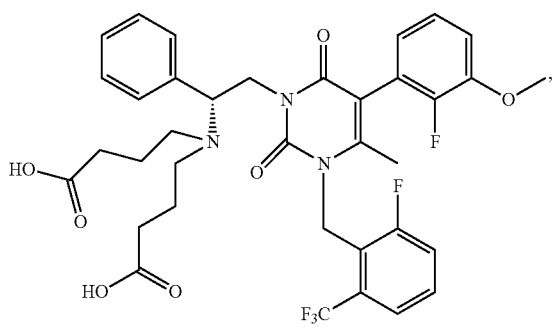

and one or more impurity selected from a group consisting of:
- ethyl 4-[(4R)-2-oxo-4-phenyl-1,2λ⁴,3-oxathiazolidin-3-yl]butanoate;
- ethyl 4-[(4R)-2,2-dioxo-4-phenyl-1,2λ⁶,3-oxathiazolidin-3-yl]butanoate; and
- (4-ethoxy-4-oxobutyl){(1R)-2-[5-(2-fluoro-3-methoxyphenyl)-3-{[2-fluoro-6-(trifluoromethyl)phenyl]methyl}-4-methyl-2,6-dioxo-3,6-dihydropyrimidin-1-(2H)-yl]-1-phenylethyl}sulfamic acid or a salt thereof, (iii)
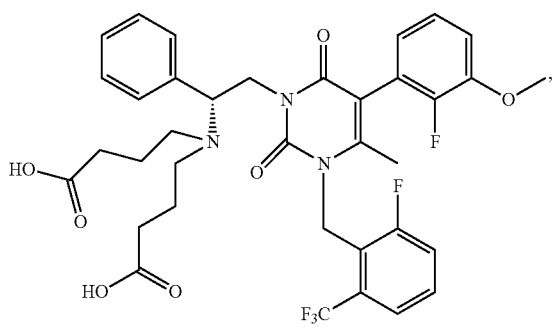

(v)

-continued (vi)

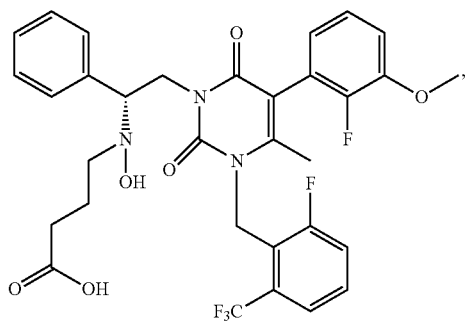

(vii)

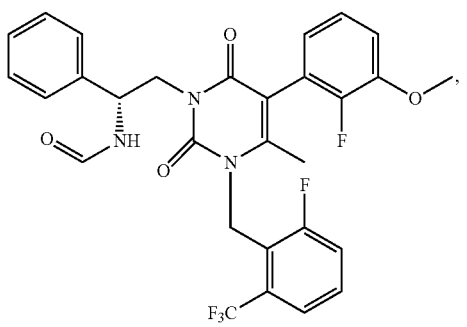

(viii)

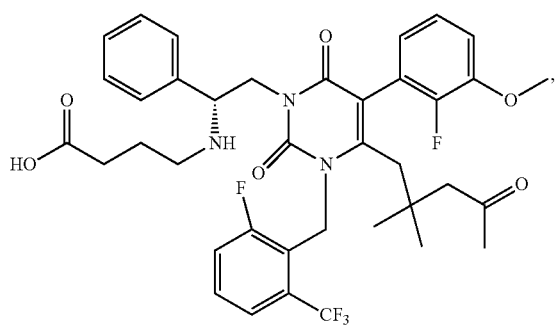

wherein the composition comprises at least about 97 weight percent of Compound (I); and wherein the one or more impurity is present in an amount that is greater than zero and equal to or less than 3 weight percent of the composition, and further wherein the composition is prepared by a process comprising, using as an intermediate, Compound (VIa), (VIa)

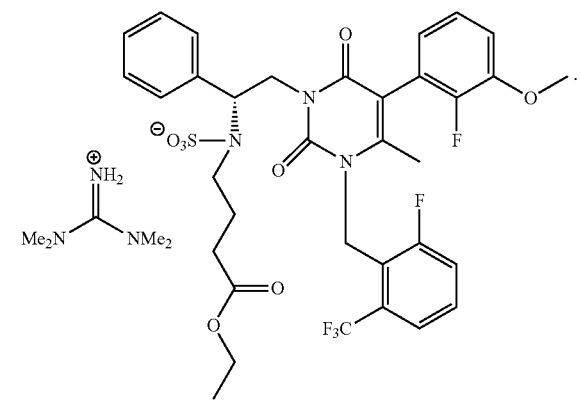

10. The composition of claim 9, wherein the composition further comprises one or more additional impurities, wherein the one or more additional impurities are selected from the group consisting of:

(i)

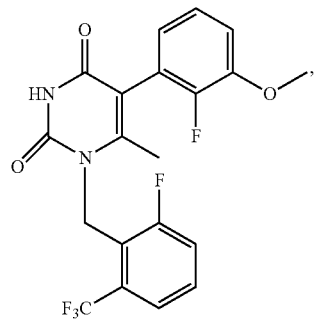

(IIa)

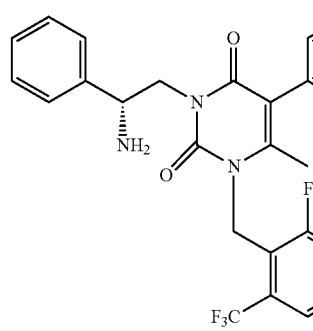

(ii)

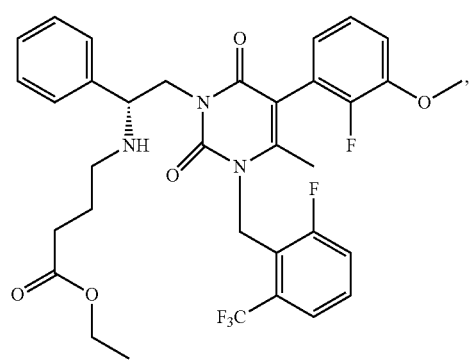

(iii)
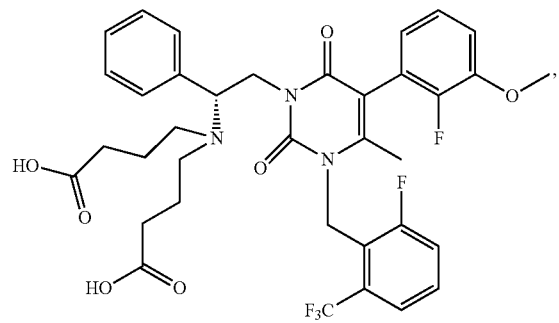
(v)
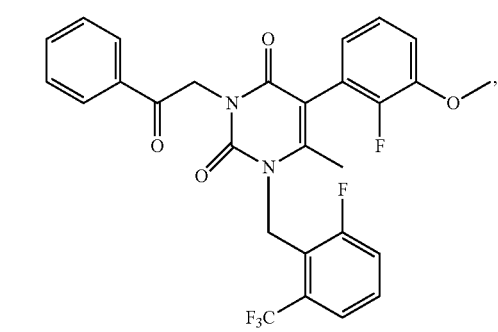
(vi)
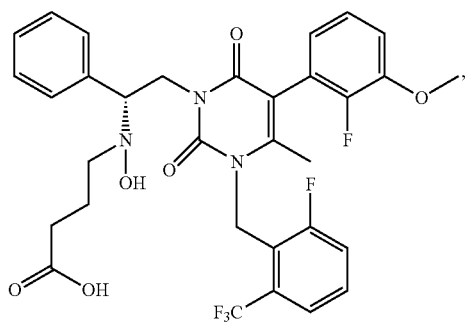
(vii)
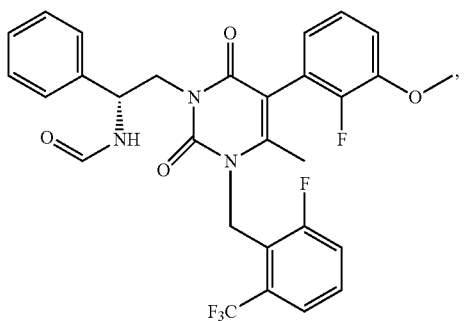
(viii)
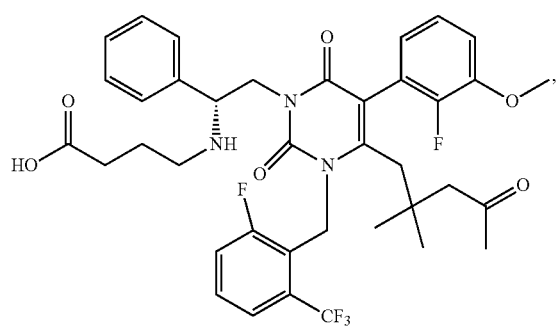
(iv)
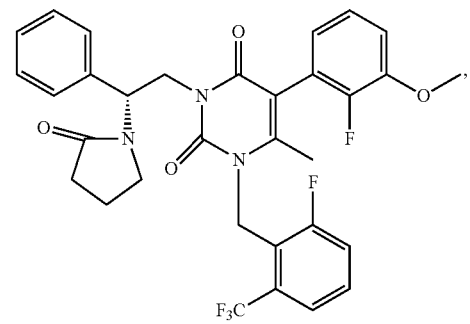
(x)
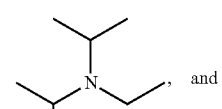, and
(xviii)
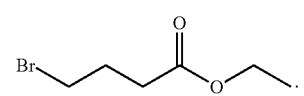.
11. A composition comprising,
Compound (I),
(I)
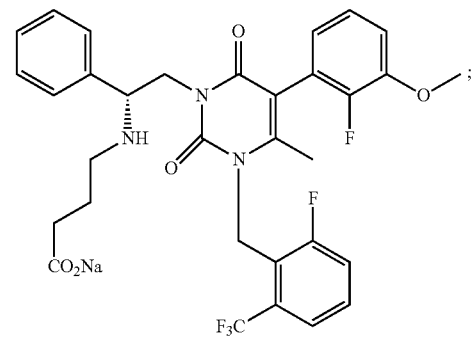
and one or more impurity a second compound selected from a group consisting of:

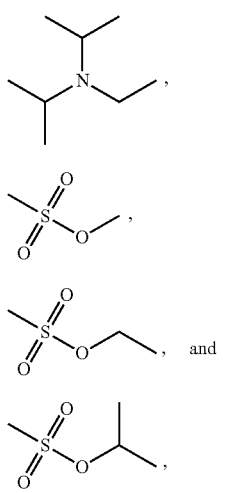

wherein the composition comprises at least about 97 weight percent of Compound (I) and wherein the one or more impurity is present in an amount that is greater than zero and equal to or less than 3 weight percent of the composition.

12. The composition of claim 1, wherein the composition further comprises one additional impurity, wherein the one additional impurity is:

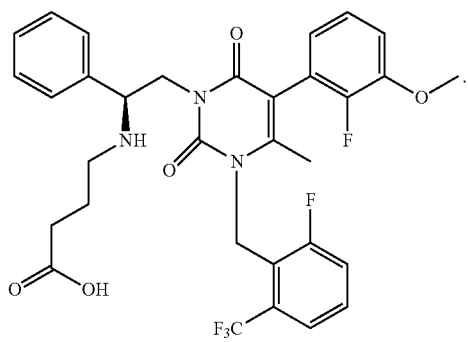

13. The composition of claim 5, wherein the composition further comprises one additional impurity, wherein the one additional impurity is:

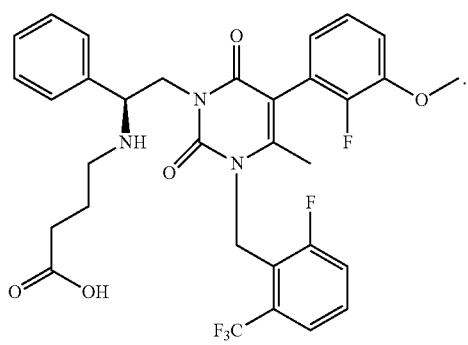

14. The composition of claim 9, wherein the composition further comprises one additional impurity, wherein the one additional impurity is:

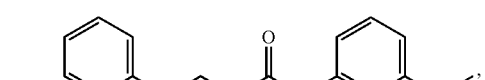

15. The composition of claim 1, wherein the one or more impurity comprises Compound (iii)

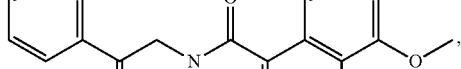

the composition comprises at least 97 weight percent of Compound (I) and not more than 0.25 weight percent Compound (iii).

16. The composition of claim 1, wherein the one or more impurity comprises Compound (v)

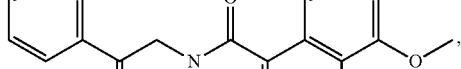

the composition comprises at least 97 weight percent of Compound (I) and not more than 0.55 weight percent Compound (v).

17. The composition of claim 1, wherein the one or more impurity comprises Compound (vi)

(vi)

[Structure of Compound (vi)]

the composition comprises at least 97 weight percent of Compound (I) and not more than 0.40 weight percent Compound (vi).

18. The composition of claim 1, wherein the one or more impurity comprises Compound (vii)

(vii)

[Structure of Compound (vii)]

the composition comprises at least 97 weight percent of Compound (I) and not more than 0.35 weight percent Compound (vii).

19. The composition of claim 11, wherein the one or more impurity comprises Compound (x)

(x)

[Structure of Compound (x)], and the composition comprises at least 97 weight percent of Compound (I) and not more than 25 parts per million (ppm) Compound (x).

20. The composition of claim 11, wherein the one or more impurity comprises Compound (xv)

(xv)

[Structure of Compound (xv)], and the composition comprises at least 97 weight percent of Compound (I) and not more than 0.6 parts per million (ppm) Compound (xv).

21. The composition of claim 11, wherein the one or more impurity comprises Compound (xvi)

(xvi)

[Structure of Compound (xvi)], and the composition comprises at least 97 weight percent of Compound (I) and not more than 0.9 parts per million (ppm) Compound (xvi).

22. The composition of claim 11, wherein the one or more impurity comprises Compound (xvii)

(xvii)

[Structure of Compound (xvii)], and the composition comprises at least 97 weight percent of Compound (I) and not more than 2.5 parts per million (ppm) Compound (xvii).

\* \* \* \* \*